United States Patent [19]
Köster

[11] Patent Number: 6,140,053
[45] Date of Patent: *Oct. 31, 2000

[54] DNA SEQUENCING BY MASS SPECTROMETRY VIA EXONUCLEASE DEGRADATION

[75] Inventor: Hubert Köster, Concord, Mass.

[73] Assignee: Sequenom, Inc., San Diego, Calif.

[ * ] Notice: This patent is subject to a terminal disclaimer.

[21] Appl. No.: 09/160,671

[22] Filed: Sep. 25, 1998

Related U.S. Application Data

[63] Continuation of application No. 08/744,590, Nov. 6, 1996, which is a continuation-in-part of application No. 08/388,171, Feb. 10, 1995, Pat. No. 5,622,824, which is a continuation of application No. 08/034,738, Mar. 19, 1993, abandoned.

[51] Int. Cl.[7] .................................................... C12Q 1/68
[52] U.S. Cl. ............................ 435/6; 536/25.3; 422/68.1
[58] Field of Search ................................. 435/6; 536/25.3; 422/68.1

[56] References Cited

U.S. PATENT DOCUMENTS

| | | | |
|---|---|---|---|
| 3,568,735 | 6/1968 | Lancsaster | 141/238 |
| 3,776,700 | 12/1973 | Gallant | 422/65 |
| 3,807,235 | 4/1974 | Lefkovitz et al. | 73/863.32 |
| 4,139,346 | 2/1979 | Rabbani | 422/56 |
| 4,214,159 | 7/1980 | Hillenkamp et al. | 250/288 |
| 4,683,194 | 7/1987 | Saiki et al. | 435/6 |
| 4,725,677 | 2/1988 | Köster et al. | 536/27 |
| 4,729,947 | 3/1989 | Middendorf et al. | 435/6 |
| 4,757,141 | 7/1988 | Fung et al. | 536/27 |
| 4,778,993 | 10/1988 | Waugh | 250/287 |
| 4,797,355 | 1/1989 | Stabinsky | 435/6 |
| 4,806,546 | 2/1989 | Carrico et al. | 536/27 |
| 4,843,003 | 6/1989 | Henikoff et al. | 435/9 |
| 4,855,225 | 8/1989 | Fung et al. | 435/6 |
| 4,882,127 | 11/1989 | Rosenthal et al. | 422/50 |
| 4,920,264 | 4/1990 | Becker | 250/282 |
| 4,948,882 | 8/1990 | Ruth | 536/27 |
| 4,994,373 | 2/1991 | Stavrianopoulos et al. | 435/6 |
| 4,997,928 | 3/1991 | Hobbs, Jr. | 536/24 |
| 5,002,868 | 3/1991 | Jacobson et al. | 536/25 |
| 5,003,059 | 3/1991 | Brennan | 536/27 |
| 5,023,187 | 6/1991 | Koebler et al. | 436/180 |
| 5,045,694 | 9/1991 | Beavis et al. | 250/287 |
| 5,064,754 | 11/1991 | Mills | 435/6 |
| 5,077,210 | 12/1991 | Eigler et al. | 435/176 |
| 5,082,935 | 1/1992 | Cruickshank | 536/27 |
| 5,118,605 | 6/1992 | Urdea | 435/6 |
| 5,118,937 | 6/1992 | Hillenkamp et al. | 250/282 |
| 5,135,870 | 8/1992 | Williams et al. | 436/173 |
| 5,143,854 | 9/1992 | Pirrung et al. | 436/518 |

(List continued on next page.)

FOREIGN PATENT DOCUMENTS

| | | |
|---|---|---|
| 0359225 | 3/1990 | European Pat. Off. . |
| 0360676 | 3/1990 | European Pat. Off. . |
| 0360677 | 3/1990 | European Pat. Off. . |

(List continued on next page.)

OTHER PUBLICATIONS

Beck et al., Chemiluminescent detection of DNA: application for DNA sequencing and hybridization, *Nucl Acids Res* 17:5115–5123 (1989).

Chu et al. "Synthesis of an amplifiable reporter RNA for bioassays" *Nucleic Acid Research* 1986, col. 14, pp. 5590–5603.

(List continued on next page.)

*Primary Examiner*—Ardin H. Marschel
*Attorney, Agent, or Firm*—Stephanie L. Seidman; Heller Ehrman White & McAuliffe

[57] ABSTRACT

The invention provides fast and highly accurate mass spectrometer based processes for directly sequencing a target nucleic acid (or fragments generated from the target nucleic acid), which by means of protection, specificity of enzymatic activity, or immobilization, are unilaterally degraded in a stepwise manner via exonuclease digestion and the nucleotides, derivatives or truncated sequences detected by mass spectrometry.

44 Claims, 29 Drawing Sheets

U.S. PATENT DOCUMENTS

| | | | |
|---|---|---|---|
| 5,149,625 | 9/1992 | Church et al. | 435/6 |
| 5,174,962 | 12/1992 | Brennan et al. | 422/78 |
| 5,202,561 | 4/1993 | Giessmann et al. | 250/281 |
| 5,210,412 | 5/1993 | Levis et al. | 250/288 |
| 5,221,518 | 6/1993 | Mills | 422/62 |
| 5,237,016 | 8/1993 | Ghosh et al. | 525/329.4 |
| 5,242,974 | 9/1993 | Holmes | 525/54.11 |
| 5,283,342 | 2/1994 | Gustavson et al. | 548/304.1 |
| 5,288,644 | 2/1994 | Beavis et al. | 436/94 |
| 5,380,833 | 1/1995 | Urdea | 536/22.1 |
| 5,410,068 | 4/1995 | Coull et al. | 548/545 |
| 5,422,253 | 6/1995 | Dahlberg et al. | 435/91.53 |
| 5,430,136 | 7/1995 | Urdea et al. | 536/243 |
| 5,436,327 | 7/1995 | Southern et al. | 536/25.34 |
| 5,474,895 | 12/1995 | Ishii et al. | 435/6 |
| 5,478,893 | 12/1995 | Ghosh et al. | 525/329.4 |
| 5,484,701 | 1/1996 | Cocuzza et al. | 435/6 |
| 5,503,980 | 4/1996 | Cantor | 435/6 |
| 5,506,348 | 4/1996 | Pieles | 536/23.1 |
| 5,512,439 | 4/1996 | Hornes et al. | 435/6 |
| 5,514,548 | 5/1996 | Krebber et al. | 436/6 |
| 5,527,675 | 6/1996 | Coull et al. | 435/6 |
| 5,541,311 | 7/1996 | Dahlberg et al. | 536/23.7 |
| 5,541,313 | 7/1996 | Ruth | 536/24.3 |
| 5,547,835 | 8/1996 | Köster | 435/6 |
| 5,571,669 | 11/1996 | Lu et al. | 435/6 |
| 5,580,733 | 12/1996 | Levis et al. | 435/6 |
| 5,601,982 | 2/1997 | Sargent et al. | 435/6 |
| 5,604,099 | 2/1997 | Erlich et al. | 435/6 |
| 5,605,662 | 2/1997 | Heller et al. | 422/68.1 |
| 5,605,798 | 2/1997 | Köster | 435/6 |
| 5,612,474 | 3/1997 | Patel | 536/27.14 |
| 5,614,402 | 3/1997 | Dahlberg et al. | 435/199 |
| 5,622,824 | 4/1997 | Koster | 435/6 |
| 5,624,711 | 4/1997 | Sundberg et al. | 427/261 |
| 5,625,184 | 4/1997 | Vestal et al. | 250/287 |
| 5,627,369 | 5/1997 | Vestal et al. | 250/287 |
| 5,631,134 | 5/1997 | Cantor | 435/6 |
| 5,643,798 | 7/1997 | Beavis et al. | 436/94 |
| 5,663,242 | 9/1997 | Ghosh et al. | 525/329.4 |
| 5,670,322 | 9/1997 | Eggers et al. | 435/6 |
| 5,670,381 | 9/1997 | Jou et al. | 436/518 |
| 5,688,642 | 11/1997 | Chrisey et al. | 435/6 |
| 5,691,141 | 11/1997 | Köster | 435/6 |
| 5,691,142 | 11/1997 | Dahlberg et al. | 435/6 |
| 5,700,642 | 12/1997 | Monforte et al. | 435/6 |
| 5,719,028 | 2/1998 | Dahlberg et al. | 435/6 |
| 5,760,393 | 6/1998 | Vestal et al. | 250/282 |
| 5,777,324 | 7/1998 | Hillenkamp | 250/288 |
| 5,777,325 | 7/1998 | Weinberger et al. | 250/287 |
| 5,795,714 | 8/1998 | Cantor et al. | 435/6 |
| 5,795,763 | 8/1998 | Dahlberg et al. | 435/194 |
| 5,821,063 | 10/1998 | Patterson et al. | 435/6 |
| 5,830,655 | 11/1998 | Monforte et al. | 435/6 |
| 5,837,450 | 11/1998 | Dahlberg et al. | 435/6 |
| 5,843,654 | 12/1998 | Heisler et al. | 435/6 |
| 5,843,669 | 12/1998 | Kaiser et al. | 435/6 |
| 5,846,710 | 12/1998 | Bajaj | 435/6 |
| 5,846,717 | 12/1998 | Brow et al. | 435/6 |
| 5,851,765 | 12/1998 | Koster | 435/6 |
| 5,869,242 | 2/1999 | Kamb | 435/6 |
| 5,871,911 | 2/1999 | Dahlberg et al. | 435/6 |
| 5,872,003 | 2/1999 | Koster | 435/283.1 |
| 5,885,775 | 3/1999 | Haff et al. | 435/6 |
| 5,888,780 | 3/1999 | Dahlberg et al. | 435/91.53 |
| 5,900,481 | 5/1999 | Lough et al. | 536/55.3 |
| 5,928,906 | 7/1999 | Koster et al. | 435/91.2 |

FOREIGN PATENT DOCUMENTS

| | | |
|---|---|---|
| 0371437 | 6/1990 | European Pat. Off. . |
| 0396116 | 11/1990 | European Pat. Off. . |
| 0412883 | 2/1991 | European Pat. Off. . |
| 0455905 | 11/1991 | European Pat. Off. . |
| 0612994 | 8/1994 | European Pat. Off. . |
| 0648280 | 4/1995 | European Pat. Off. . |
| 0785278 | 7/1997 | European Pat. Off. . |
| 3930312 | 4/1990 | Germany . |
| 4011991 | 10/1990 | Germany . |
| 2215399 | 8/1990 | Japan . |
| 6294796 | 10/1994 | Japan . |
| 2017105 | 3/1979 | United Kingdom . |
| 8903432 | 4/1989 | WIPO . |
| 8909282 | 10/1989 | WIPO . |
| 8912694 | 12/1989 | WIPO . |
| 9001564 | 2/1990 | WIPO . |
| 9003382 | 4/1990 | WIPO . |
| 9007582 | 7/1990 | WIPO . |
| 9014148 | 11/1990 | WIPO ............ B01D 59/44 |
| 9015883 | 12/1990 | WIPO . |
| 9105060 | 4/1991 | WIPO . |
| 9106678 | 5/1991 | WIPO . |
| 9111533 | 8/1991 | WIPO . |
| 9112341 | 8/1991 | WIPO . |
| 9113075 | 9/1991 | WIPO . |
| 9202635 | 2/1992 | WIPO . |
| 9203575 | 3/1992 | WIPO . |
| 9207879 | 5/1992 | WIPO . |
| 9210092 | 6/1992 | WIPO . |
| 9213629 | 8/1992 | WIPO . |
| 9215712 | 9/1992 | WIPO . |
| 9306925 | 4/1993 | WIPO . |
| 9320236 | 10/1993 | WIPO . |
| 9411530 | 5/1994 | WIPO . |
| 9416101 | 7/1994 | WIPO . |
| 9421822 | 9/1994 | WIPO . |
| 9507361 | 3/1995 | WIPO . |
| 9530773 | 11/1995 | WIPO . |
| 9531429 | 11/1995 | WIPO . |
| 9605323 | 2/1996 | WIPO . |
| 9619587 | 6/1996 | WIPO ............ C12Q 1/68 |
| 9629431 | 9/1996 | WIPO . |
| 9632504 | 10/1996 | WIPO . |
| 9636731 | 11/1996 | WIPO . |
| 9636986 | 11/1996 | WIPO . |
| 9636987 | 11/1996 | WIPO . |
| 9637630 | 11/1996 | WIPO . |
| 9708306 | 3/1997 | WIPO . |
| 9716699 | 5/1997 | WIPO . |
| 9733000 | 9/1997 | WIPO . |
| 9737041 | 10/1997 | WIPO . |
| 9742348 | 11/1997 | WIPO . |
| 9743617 | 11/1997 | WIPO . |
| 9812355 | 3/1998 | WIPO . |
| 9812734 | 3/1998 | WIPO . |
| 9820019 | 5/1998 | WIPO . |
| 9820020 | 5/1998 | WIPO . |
| 9820166 | 5/1998 | WIPO . |
| 9854751 | 12/1998 | WIPO . |

OTHER PUBLICATIONS

Connolly, B. A., "Oligonucleotides containing modified bases", *Oligonucleotides and Analogues, A Practical Approach,* Edited by F. Eckstein, Oxford University Press, Ch. 7, pp. 155–183 (1991).

Eckstein "Phosphorothiolate Analogues of Nucleotides" Accounts of chemical Research 1978, vol. 12, pp. 204–210.

Eckstein et al. "Synthesis and Properties of Diastereoisomers of Adenosine 5'–(O–1–Thiotriphosphate) and Adenosine 5'–(O–2–Thiotriphosphate)" *Biochemistry* 1976, vol. 15, No. 8, pp. 1685–1691.

Eckstein "Nucleoside Phosphorothiolates" *Ann. Rev Biochem.* 1985, vol. 54, pp. 367–402.

Eckstein (ed.), *Oligonucleotides and Analogues,* IRL Press, Oxford (1991).

Elov et al., Synthesis of RNA using T7 RNA polymerase and immobilized DNA in a stream type reactor, *Bioorganicheskala Khhimia,* 17(6) 789–794 (1991).

English Language translation of Elov et al., *Bioorganicheskala Khhimia,* 17(6) 789–794 (1991).

Greene and Wuts, *Protective Groups in Organic Synthesis,* 2nd Edition, Wiley & Sons (1991).

Haralambidis et al. "Preparation of base–modified nucleosides suitable for non–radioactive label attachment and their incorporation into synthetic oligodeoxyribonucleotides" *Nucleic Acid Research* 1987, vol. 15, No. 12, pp. 4857–4876.

Higuchi et al. "A general method of in vitro preparation and specific mutagensis of DNA fragments: study of protein and DNA interactions" *Nucleic Acid Research* 1988, vol. 16, No. 15, pp. 7351–7367.

Hobbs et al. "A General Method for the Synthesis of 2'–Azido–2'–deoxy–and 2'–Amino–2'–deoxyribofuranosyl Purines" *Journal Organic Chemistry* 1977, vol. 42, No. 4, pp. 714–719.

Ikehara et al. "Studies of Nucleosides and Nucleotides LXXIX. Purine Cyclonucleosides. (37). The Total synthesis of an Antibiotic 2'–Amino–2'–deoxyguanosine" *Chem. Phar. Bull.* 1978, vol. 26, No. 1, pp. 240–244.

Imazawa et al. "Facile Synthesis of 2'–Amino–2'–deoxyribofuranosyl Purines" *Journal Organic Chemistry* 1979, vol. 44, No. 12, pp. 2039–2041.

Li, et al., "Boron–containing oligodeoxyribonucleotide 14mer duplexes: ezymatic synthesis and melting studies" *Nucl. Acids Res.* 23:4495–4501 (1995).

McCray and Trentham, "Properties and uses of photoreactive caged compounds", *Annu. Rev. Biophys. Biophys. Chem.* 18:239–270 (1989).

Perrouault et al. "Sequence–specific artificial photo–induced endonucleases based on triple helix–forming oligonucleotides" *Nature (Letters for Nature)* 1990, vol. 344, pp. 358–360.

Pitulle et al. "Initiator oligonucleotides for the combination of chemical and enzymatic RNA synthesis" *Gene* 1992, vol. 112, pp. 101–105.

Porter, K.W., et al., "N7–cyanoborane–2'–deoxyguanosine 5'–triphosphate is a good substrate for DNA polymerase", *Biochemistry,* 34:11963–11969 (1995).

*Reactive Molecules,* The neutral reactive intermediates in organic chemistry, by C. Wentrup, John Wiley & Sons (1984).

Ruth, "Oligodeoxynucleotides with Reporter Groups Attached to the Base," *Practical Approach Series: Oligonucleotides and Analogues,* 255–282, 1991.

Sambrook et al., Molecular Cloning: A Laboratory Manual, Cold Spring Harbor Laboratory Press (1989).

Seela et al. "98. 1,7–Dideaza–2',3'–dideozyadenosine: Synthesis of Pyrrolol[2,3–b]pyridine 2',3'–Deoxyribofuranosides and Participation of Purine N(1) during HIV–1 Reverse Transcriptase Inhibition" *Helvetica Chimica Acta* 1991, vol. 74, pp. 1048–1058.

Singh et al. "Oligonucleotides, part 5+: synthesis and fluorescence studies of DNA oligomers d(AT)5 containing adenines covalently linked at C–8 with dansyl flurophore" *Nucleic acid Research* 1990, vol. 18, No. 11, pp. 3339–3345.

Sinha et al., Polymer support oligonucleotide synthesis XVIII: Use of B–cyanoethyl–N, N–dialkylamino–/N–morpholino phosphoramidite of deoxynucleosides for the synthesis of DNA fragments simplifying deprotection and isolation of final product, *Nucleic Acids Res.* 12:4539 (1984).

Sinha et al., β–cyanoethyl N, N–dialkylamino/N–morpholinomonochloro phosphoamidites, new phosphitylating agents facilitating ease of deprotection and work–up of synthesized oligonucleotides, *Tetrahedron Lett.* 24:5843–5846 (1983).

Slim et al. "Configurationally defined phosphorothiolate––containing oligoribonucleotides in the study of the mechanism of cleavage of hammerhead ribozymes" *Nucleic Acid Research* 1991, vol. 19, No. 6, pp. 1183–1188.

Sowa et al. "The facile synthesis of 5'–nucleotides by the selective phosphorylation of a primary hydroxyl group of nucleosides with phosphoryl chloride" *Bulletin of the Chemical Society of Japan* 1975, col. 48, No. 7, pp. 2084–2090.

Sproat et al., The synthesis of protected 5'–amino–2', 5'–dideoxyribonucleoside–3'–O–phosphoramidities; applications of 5'–amino–oligodeoxyribonucleotides, *Nucleic Acids Res.* 15:6181–6196 (1987).

Sproat et al., The synthesis of protected 5'–mercapto–2', 5'–dideoxyribonucleoside–3'–O–phosphoramidities; uses of 5'–mercapto–oligodeoxyribonucleotides, *Nucleic Acids Res.* 15:4837–4848 (1987).

Sproat and Lamond, "2'–O–Methyloligoribonucleotides-:systhesis and applications," *Practical Approach Series: Oligonucleotides and Analogues,* 49–86, 1991.

Verheyden et al. "Synthesis of some Pyrimidine 2'–Amino–2'–deoxynucleosides" *Journal Organic Chemistry* 1971, vol. 36, No. 2, pp. 250–254.

Zhang et al., "Single–base mutational analysis of cancer and genetic diseases using membrane bound modified oligonucleotides", *Nucl. Acids Res.* 19:3929–3933 (1991).

Andersen, et al., Electrospray ionization and matrix assisted laser desorption/ionization mass spectrometry: Powerful analytical tools in recombinant protein chemistry, *Nature Biotech.* 14:449–457 (1996).

Ardrey, "Electrospray mass spectrometry", *Spectroscopy Europe* 4(4):11–18 (1992).

Arlinghaus et al., "Applications of resonance ionization spectroscopy for semiconductor, environmental and biomedical analysis, and for DNA sequencing", *SPIE,* vol. 1435, *Opt. Methods Ultrasensitive Detect. Anal. Tech. Appl.* pp. 26–35 (1991).

Bains, "DNA Sequencing by Mass Spectrometry. Outline of a Potential Future Application", *Chimica Oggi Review* 1991, vol. Oct.

Berkenkamp et al., Infrared MALDI mass spectrometry of large nucleic acids, *Science* 281:260–2 (1998).

Braun et al., Improved Analysis of Microsatellites Using Mass Spectrometry, *Genomics* 46:18–23 (1997).

Braun et al., Detecting CFTR gene mutations by using primer oligo base extension and mass spectrometry, *Clinical Chemistry* 43:1151–1158 (1997).

Brennan et al., "New Methods to Sequence DNA by Mass Spectrometry" *SPIE/New Technologies in Cytometry and Molecular Biology* 1990, vol. 1206, pp. 60–67.

Chen et al., "Laser mass spectrometry for DNA fingerprinting for forensic applications", Annual Meeting of the Society of Photo Optical Instrumentation Engineers, Jul. 24–29, 1994.

Covey, et al., The determination of protein, oligonucleotide and peptide molecular weights by ion–spray mass spectrometry, *Rapid Comm. Mass Spectrom.* 2:249–256 (1988).

Crain, "Mass spectrometric techniques in nucleic acid research", *Mass Spectr. Rev.* 9:505–554 (1990).

Doktycz et al., "Analysis of Polymerase Chain Reaction––Amplified DNA Products by Mass Spectrometry Using Matrix Assisted Laser Desorption and Ekectrospray: Current Status" *Anal. Biochem.* 230:205–214 (1995).

Edmonds et al., Thermospray liquid chromatography–mass spectrometry of nucleosides and of enzymatic hydrolysates of nucleic acids, *Nucleic Acids Research* 13:8197–8206 (1985).

Edmonds, et al., "electrospray Ionization Mass Spectrometry" *Methods in Enzymology* 1990, vol. 193, pp. 412–431.

Eggers et al., "A microchip for quantitative detection of molecules utilizing luminescent and radioisotope reporter groups", *Bio Techniques* 17:516–524 (1994).

Fu et al., Efficient preparation of short DNA sequence ladders potentially suitable for MALDI–TOF DNA sequencing, *Genetic Analysis* 12:137–142 (1996).

Fu et al., Sequencing exons 5 to 8 of the p53 gene by MALDI–TOF mass spectrometry, *Nat Biotechnol* 16:381–4 (1998).

Ganem, "Detection of oligonucleotide duplex forms by ion–spray mass spectrometry", *Tetrahedron Letters* 34(9):1445–1448 (1993).

Green et al., "Variable–wavelength On–column Fluorescence Detector for Open–tubular Zone Electrophoresis" *Journal of Chromatography* 1986, vol. 352, pp. 337–343.

Hillenkamp et al., Laser desorption mass spectrometry Part 1: Basic mechanisms and techniques, *Mass Spectrometry in the Biological Sciences: A tutorial,* pp. 165–179 (1992).

Hillenkamp et al., Matrix assisted UV–laser desorption/ionization: a new approach to mass spectrometry of large biomolecules, *Biological Mass Spectrometry* (Burlingame and McCloskey, eds.) Elsevier Science Publishers, Amsterdam, pp. 49–61 (1987).

Huth–Fehre et al., Matrix–assisted laser desorption mass spectrometry of oligodeoxythymidylic acids, *Rapid Comm in Mass Spect* 6:209–213 (1992).

Jacobson, et al., "Applications of mass spectrometry to DNA sequencing", *GATA* 8(8):223–229 (1991).

Jacobson et al., "Applications of mass spectrometry to DNA fingerprinting and DNA sequencing", *International Symposium on the Forensic Aspects of DNA Analysis,* pp. 1–18, Mar. 29–Apr. 2, 1993.

Ji et al., Two–dimensional electrophoretic analysis of proteins expressed by normal and cancerous human crypts: Application of mass spectrometry to peptide–mass fingerprinting, *Electrophoresis* 15:391–405 (1994).

Juhasz et al., Applications of delayed extraction matrix–assisted laser desorption ionization time–of–flight mass spectrometry to oligonucleotide analysis, *Analy Chem* 68:941–946 (1996).

Jurinke et al., Application of nested PCR and mass spectrometry for DNA–based virus detection: HBV–DNA detected in the majority of isolated anti–HBc positive sera, *Genetic Analysis* 14:97–102 (1998).

Jurinke et al., Analysis of ligase chain reaction products via matrix–assisted laser desorption/ionization time–of–fight––mass spectrometry, *Analy Biochem* 237:174–181 (1996).

Jurinke et al., Recovery of nucleic acids from immobilized biotin–streptavidin complexes using ammonium hydroxide and applications in MALDI–TOF mass spectrometry, *Anal. Chem.* 69:904–910 (1997).

Jurinke et al., Detection of hepatitis B virus DNA in serum samples via nested PCR and MALDI–TOF mass spectrometry, *Genetic Analysis* 13:67–71 (1996).

Kirpekar et al., DNA sequence analysis by MALDI mass spectrometry, *Nucleic Acids Res.* 26:2554–9 (1998).

Landegren et al., "DNA Diagnostics—Molecular techniques and automation", *Science* 242:229–237 (1988).

Li et al., "High–Resolution MALDI Fourier Transform Mass Spectrometry of Oligonucleotides", *Anal Chem* 68(13):2090–2096 (1996).

Little et al., Verification of 50– to 100–mer DNA and RNA sequences with high–resolution mass spectrometry, *Proc. Natl. Acad. Sci. USA* 92:2318–2322 (1995).

Little et al., "Mass spectrometry from miniaturized arrays for full comparative DNA analysis", *Nature Med* 3(12):1413–1416 (1997).

Little et al., Detection of RET proto–oncogene codon 634 mutations using mass spectrometry, *J. Mol Med* 75:745–750 (1997).

Little et al., "MALDI on a Chip: Analysis of Arrays of Low–Femtomole to Subfemtomole Quantities of Synthetic Oligonucleotides and DNA Diagnostic Products Dispensed by a Piezoelectric Pipet", *Anal chem* 69:4540–4546 (1997).

Little et al., "Direct detection of synthetic and biologically generated double–stranded DNA by MALDI–TOF MS", *J. Mass Spec* 17:1–8 (1997).

Liu et al., "Use of a Nitrocellulose Film Substrate in Matrix–Assisted Laser Desorption/Ionization Mass Spectrometry for DNA Mapping and Screening", *Anal. Chem.* 67: 3482–3490 (1995).

Liu et al., Rapid screening of genetic polymorphisms using buccal cell DNA with detection by matrix–assisted laser desorption/ionization mass spectrometry, *Rapid Comm in Mass Spect* 9:735–743 (1995).

*Methods in Enzymology* vol. 193: Mass Spectrometry (McCloskey, editor), p. 425 Academic Press, New York (1990).

Moini, M. and Abramson, F.P., "A moving belt device to couple high–performance liquid chromatography and chemical reaction interface mass spectrometry" *Biological Mass Spectrometry,* 20:308–312 (1991).

Monforte and Becker, High–throughout DNA analysis of time–of–flight mass spectrometry, *Nature Medicine* 3:360–362 (1997).

Nelson et al., Volatilization of High Molecular Weight DNA by pulsed Laser Ablation and ionization from a frozen aqueous matrix, *Rapid Communications in Mass Spectrometry* 4:348–351 (1990).

Nelson et al., Time–of–flight mass spectrometry of nucleic acids by laser ablation and ionization from a frozen aqueous matrix, *Rapid Communications in Mass Spectrometry* 4:348–351 (1990).

Nordoff et al., "Matrix–assisted laser desorption/ionization mass spectrometry of nucleic acids with wavelength in the ultraviolet and infrared", *Rapid Comm. Mass Spectrom.* 6:771–776 (1992).

O'Donnell et al., "MassArray as an Enabling Technology for the Industrial–Scale Analysis of DNA", *Genetic Engineering News* 17(21) (1997).

Overberg et al., Laser Desorption Mass Spectrometry. Part II Performance and Applications of Matrix–Assisted Laser Desorption/Ionization of Large Biomolecules, *Mass Spectrometry in the Biological Sciences: A Tutorial*. Editor: M. L. Gross, Kluwer Publications, The Netherlands, pp. 181–197 (1992).

Pieles et al., Matrix–assisted laser desorption ionization time–of–flight mass spectrometry: a powerful tool for the mass and sequence analysis of natural and modified oligonucleotides, *Nucleic Acids Res.* 21(14):3191–3196 (1993).

Pomerantz et al., Determination of oligonucleotide composition from mass spectrometrically measured molecular weight, *Am. Soc. Mass Spectrom.* 4:204–09 (1993).

Schneider and Chait, Increased stability of nucleic acids containing 7–deaza–guanosine and 7–deaza–adenosine may enable rapid DNA sequencing by matrix–assisted laser desorption mass spectrometry, *Nucleic Acids Res.* 23(9):1570–1575 (1995).

Schram, Mass spectrometry of nucleic acid componenents, *Biomed. App. Mass Spectrom.* 34:203–287 (1990).

Shaler et al., Effect of Impurities on the matrix–assisted laser desorption mass spectra of single–stranded oligodeoxynucleotides, *Anal. Chem.* 68:576–579 (1996).

Siegert et al., Matrix–assisted laser desorption/ionization time–of–flight mass spectrometry for the detection of polymerase hain reaction products containing 7–deasapurine moieties, *Anal. Biochem.* 243:55–65 (1996).

Siuzdak, The emergence of mass spectrometry in biochemical research, *Proc. Natl. Acad. Sci. USA* 91:11290–11297 (1994).

Smith et al., Capillary zone electrophoresis–mass spectrometry using an electrospray ionization interface, *Anal. Chem.* 60:436–441 (1988).

Smith, R. D., "New Developments in Biochemical Mass Spectrometry: Electrospray Ionization", *Anal. Chem.* 62:882–899 (1990).

Still et al. "Rapid Chromatographic Technique for Preparative Separations with Moderate Resolution" *Journal Organic Chemistry* 1978, vol. 43, No. 14, pp. 2923–2925.

Swerdlow et al. "Capillary gel elctrophoresis for rapid, high resolution DNA sequencing" *Nucleic acid Research* 1990, vol. 18, No. 6, pp. 1415–1419.

Tang et al., Detection of 500–nucleotide DNA by laser desorption mass spectrometry, *Rapid Commun. Mass Spectrom.* 8:727–730 (1994).

Tang et al., Matrix–assisted laser desorption/ionization mass spectrometry of immobilized duplex DNA probes, *Nucleic Acid Res.* 23(16):3126–3131 (1995).

Tang et al., Matrix–assisted laser desorption/ionization of restriction enzyme–digested DNA, *Rapid Commun. Mass Spectrom.* 8:183–186 (1994).

Time of Flight Mass Spectrometry of DNA for Rapid Sequence Determination. Technical Progress Report, Jul. 31, 1991–Jul. 31, 1992, Arizona State University., Tempe.

Williams, Time of flight mass spectrometry of DNA laser–ablated from frozen aqueous solutions: applications to the Human Genome Project, *Intl. J. Mass Spectrom. and Ion Processes* 131:335–344 (1994).

Wolter et al., Negative ion FAB mass spectrometric analysis of non–charged key intermediated in oligonucleotide synthesis: rapid identification of partially protected dinucleoside monophosphates, *Biomedical Environmental Mass Spectrometry* 14:111–116 (1987).

Wu et al., "Time–of–Flight Mass Spectrometry of Underivatized Single–Stranded DNA Oligomers by Matrix–Assisted Laser Desorption", *Anal. Chem.* 66:1637–1645 (1994).

Yamashita et al. "Electrospray Ion Source. Another Variation on the Free–Jet Theme" *J. Phys. Chem.* 1984, vol. 88, pp. 4451–4459.

Arshady, Reza, Beaded polymer supports and gels: II. Physico–chemical criteria and functionalization, *Journal of Chromatography*, 586:199–219 (1991).

Batista–Viera et al., A new method for reversible immobilization of thiol biomolecules bsed on solid–phase bound thiolsulfonate groups, *App. Biochem and Biotech*, 31:175–195 (1991).

Chrisey et al., Fabrication of patterned DNA surfaces, *Nucl. Acids. Res.* 24:3040–3047 (1996).

Chrisey et al., Covalent attachment of synthetic DNA to self–assembled monlayer films, *Nucl. Acids Res.* 24:3031–3039 (1996).

Damha, Masad J. et al.; An improved procedure for derivatization of controlled–pore glass beads for solid–phase oligonucleotide synthesis; *Nucleic Acids Research* 18(13):3813–3821 (1990).

Ghosh, et al., "Covalent attachment of oligonunucleotides to solid supports", *Nuc. Acids. Res.* 15(13):5353–5372 (1987).

Gildea et al., A versatile acid–labile linker for modification of synthetic biomolecules, *Tetrahedron Letters* 31:7095–7098 (1990).

Hayashi, et al., "Immobilization of Thiol Proteases onto porous poly(vinyl alcohol) beads", *Polymer Journal*, 25(5):489–497 (1993).

Heermann, et al., "Liquid–phase hybridization and capture of hepatitis B virus DNA with magnetic beads and fluorescence detection of PCR product", *J. of Virol. Methods* 50:43–58 (1994).

Hermanson, *Bioconjugate Techniques*, Academic Press (1996).

Lamture et al., "Direct detection of nucleic and hybridization on the surface of a charge coupled device", *Nucl. Acids Res.* 22:2121–2125 (1994).

Lund, Vera et al., "Assessment of methods for covalent binding of nucleic acids to magnetic beads, dynabeads, and the characteistics of the bound nucleic acids in hybridization reactions", *Nucleic Acids Res.* 16(22) (1988).

Manoharan et al., A 2'–O–thiol tether in the ribose moiety of nucleic acids for conjugation chemistry, *Gene*, 149:147–156 (1994).

Nikiforov and Rogers, "The use of 96–well polystyrene plates for DNA hybridization–based assays: An evaluatin of different approaches to oligonucleotide immobilization", *Anal. Biochm.* 227:201–209 (1995).

O'Donnell et al., High–density, covalent attachment of DNA to silicon wafers for analysis by MALDI–TOF mass spectrometry, *Analytical Chemistry* 69:2438–2443 (1997).

O'Donnell–Maloney et al., "Microfabrication and array technologies for DNA sequencing and diagnostics", *Genetic Analysis: Biomolecular Engineering* 13:151–157 (1996).

Olejnik et al., "Photocleavable biotin phosphoramidite for 5'–end–labeling, affinity purification and phosphorylation of synthetic oligonucleotides", *Nucleic Acids Res.* 24:351–366 (1996).

Pon, et al., Derivation of controlled pore glass beads for solid phase oligonucleotide synthesis, *BioTechniques*, 6:8, 770–775 (1988).

Rasmussen et al., "Covalent immobilization of DNA onto polystyrene microwells: The molecules ar eonly bound at the 5' end", *Anal. Biochem.* 198:138–142 (1991).

Running and Urdea, "A procedure for productive coupling of synthetic oligonucleotides to polystyrene microtiter wells for hybridization capture", *Biotechniques* 8:276–277 (1990).

Stahl, et al., "Solid phase DNA sequencing using the biotin–avidin system", *Nucleic Acids Res.* 16(7):3025–3039 (1988).

Zuckerman et al., Efficient methods for attachment of thiol specific probes to the 3'-ends of synthetic oligodeoxyribonucleotides, *Nucleic Acids Research,* 15:13, 5305–5321 (1987).

Axelrod et al., "Transcription from Bacteriophage T7 and SP6 RNA Polymerase Promoters in the Presence of 3'-Deoxyribonucleodside 5'-Triphosphate Chain Terminators", *Biochemistry* 1985, vol. 24, pp. 5716–5723.

Bains, "Setting a Sequence to Sequence a Sequence" *BIO/Technology* 1992, vol. 10, pp. 757–758.

Barrell B., "DNA sequencing: present limitations and prospects for the future", *FASEB Journal* 5:40–45 (1991).

Beck et al., Applications of dioxetane chemiluminescent probes to molecular biology, *Anal. Chem.* 62:2258–2270 (1990).

Broude et al., Enhanced DNA sequencing by hybridization, *Proc. Natl. Acad. Sci. USA* 91:3072–3076 (1994).

Brumbaugh et al., "Continuous, on–line DNA sequenceing using oligodeoxynucleotide primers with multiple fluorophores" *PNAS* 1988, vol. 85, pp. 5610–5614.

Church et al., "Multiplex DNA Sequencing", *Science* 240:185–188 (1988).

Drmanac, et al., "Sequencing of megabase plus DNA by hybridization: theory of the method", *Genomics* 4:114–128 (1989).

Frank and Köster, DNA chain length and the influence of base composition on electrophoretic mobility of oligodeoxyribonucleotides in polyacrylamide–gels, *Nucl. Acids Res.* 6:2069–2087 (1979).

Fu, et al., "A DNA sequencing strategy that requires only five bases of known terminal sequence for priming (primer extention/stacking interaction/fluorescein/solid state/duplex probe)", *Proc. Natl. Acad. Sci. USA* 92:10162–10166 (1995).

Fu et al., Sequencing double–stranded DNA by strand displacement, *Nucl Acids Res* 25:677–679 (1997).

Henikoff, S., "Unidirectional digestion with exonuclease III creates targeted breakpoints for DNA sequencing", *Gene,* 28:351–359 (1984).

Hyman "A New Method of Sequencing DNA" *Analytical Biochemistry* 1988, vol. 174, pp. 423–436.

Jett et al., "High–Speed DNA Sequencing: An Approach Based Upon fluorescence Detection of Single Molecules", *J. Bio Strut & Dynam.* 7(2):301–09 (1989).

Khrapko et al., "A method for DNA sequencing by hybridization with oligonucleotide matrix", *J. DNA Seq. and Mapping* 1:375–388 (1991).

Khrapko et al. "An Oligonucleotide hybridization approach to DNA sequencing" *FEBS Letters* 1989, vol. 256, No. 1,2, pp. 118–122.

Kuppuswamy, et al., "Single nucleotide primer extension to detect gentic diseases: experimental application to hemophilia B (factor IX) and cystic fibrosis genes", *Proc. Natl. Acad. Sci. USA* 88:1143–1147 (1991).

Lim et al. "Optimal Conditions for Supercoli DNA Sequencing with the *Eschirichia coli* DNA Polymerase I Large Fragment" *Gene Anal. Techn.* 1988, vol. 5, pp. 32–39.

Liss, Alan R. "Macromolecular sequencing and synthesis selected methods and applications", Edited by David H. Schlesinger, Department of Experimental Medicine and Cell Biology, New York University Medical Center, New York, New York 127–149 (1988).

Little et al., Identification of apolipoprotein E polymorphisms using temperature cycled primer oligo base extension and mass spectrometry, *Short Communiation.* Eur. J. Clin Chem Clin Biochem 35(7) pp. 545–548 (1993).

Lopez–Galindez, et al., "Characterization of genetic variation and 3'–azido–3'–deoxythymidine–resistance mutations of human immunodeficiency virus by the RNase A mismatch cleavage method", *Proc. Natl. Acad. Sci. USA* 88:4280–4284 (1991).

Martin, "New technologies for large–genome sequencing", *Genome* 31:1073–1080 (1989).

Milligan, J.F., et al., "Oligoribonucleotide synthesis using T7 RNA polymerase and synthetic DNA templates", *Nucl. acids Res.,* 15:8783–8798 (1987).

Nakamaye et al. "Direct sequencing of polymerase chain reaction amplified DNA fragments through the incorporation of deoxynucleodside o–thiotriphosphates" *Nucleic Acid Research* 1988 vol. 16, No. 21, pp. 9947–9959.

Nielsen et al., "Sequence–selective recognition of DNA by strand displacement with a thymine–substituted polyamide" *Science* 254:1497–1500 (1991).

Nikiforov et al., Genetic bit analysis: a solid phase method for typing single nucleotide polymorphisms, *Nucleic Acids Res* 22(20):4167–4175 (1994).

Prober et al. "A system for Rapid DNA Sequencing with Fluorescent Chain–Terminating Dideoxynucleotides" *Science Research Articles* 1987, vol. 238, pp. 336–341.

Saiki, et al., "Genetic analysis of amplified DNA with immobilized sequence–specific oligonucleotide probes", *Proc. Natl. Acad. Sci. USA* 86:6230–6234 (1989).

Sanger, F., et al., DNA Sequencing With Chain–Terminating Inhibitors, *PNAS* USA, 74:5463 (1977).

Smith et al. "Fluorescence detection in automated DNA sequence analysis" *Nature* 1986, col. 321, pp. 674–679.

Trainor, DNA Sequencing, Automation and the Human Genome, *Anal. Chem.,* vol. 62, pp. 418–426 (1990).

Köster, et al., "Oligonucleotide synthesis and multiplex DNA sequencing using chemiluminescent detection", *Nucleic Acids Research,* Symposium Series No. 24, 318–321 (1991).

Köster et al., "A strategy for rapid and efficient DNA sequencing by mass spectrometry", *Nature Bio* 14:1123–1128 (1996).

Köster et al., Polymer support oligonucleotide synthesis—XV$^{1,2}$, *Tetrahedron* 40:102–112 (1984).

Köster et al., Well–defined insoluble primers for the enzymatic synthesis of oligo– and polynucleotides, *Hoppe Seylers Z. Physiol. Chem.* 359(11):1579–1589 (1978).

Köster et al., N–acyl protecting groups for deoxynucleotides: A quantitative and comparative study, *Tetrahedron* 37:363–369 (1981).

Köster et al., Some improvements in the synthesis of DNA of biological interest, *Nucl Acids Res* 7:39–59 (1980).

Certified English translation of European patent 041288A1, Fast screening and/or identification of a single base on a nucleic acid sequence, including applications (1991).

Certified English translation of Japanese patent 6–294796, Nucleic acid analysis method (1989).

Database WPI, Derwent Publication #199433, citing European Patent No. 0612994, Matrix materials for matrix–supported laser desorption mass spectroscopy (1999).

Database WPI, Derwent Publication #199015, citing European Patent No. 0360677, Identification of sub–units in complex moles.—by mass spectrometry, especially in nucleic acid sequencing (1998).

Database WPI, Derwent Publication #199018, citing German Patent No. 3930312, Nucleic acid sequencing—involving amplification–denaturation cycles in presence of deoxy–nucleoside alpha–thio–triphosphate (1998).

Database WPI, Derwent Publication #199043, citing German Patent No. 4011991, Simultaneous sequencing of several DNA samples—by cloning into separate vectors, complementary strand synthesis from specific fluorescent labelled primers, electrphoretic sepn. etc. (1999).

Database WPI, Derwent Publication, AN90–302767, Japanese Patent, JP2215399 A, Method detect DNA single strand combination DNA prime correspond base sequence forming replica (1990).

Database WPI, Derwent Publication, 199516, for World Patent, PCT 9507361, Detecting presence and position of mutation(s) in double stranded DNA (1999).

Sequenom Reports DNA MassArray™Technology More Sensitive Than Electrophoretic Methods in Detecting Gene Mutations: Automated DNA Analysis System Can Speed Up Microsatellite Analyses, Press Release: Dec. 15, 1997, http://www.sequenom.com/pressrelease.htm.

Sequenom Advances the Industrial Genomics Revolution with the Launch of Its DNA MassArray™Automated Process Line, Press Release: Sep. 28, 1998, http://www.sequenom.com/pressrelease.htm.

Sequenom Reports On Use of Its DNA MassArray™Technology to Analyze Genes Associated with Alzheimer's Disease and Arteriosclerosis: Technology Has Applications in Drug Development, Press Release: Sep. 22, 1997, http://www.sequenom.com/pressrelease.htm.

Sequenom Signs Agreement With Bruker–Franzen Analytik to Develop Mass Spectrometer for DNA Massarray Analysis, Press Release: Jan. 12, 1998, http://www.sequenom.com/pressrelease.htm.

Sequenom Uses DNA MassArray™to Sequence Section of Human Cancer–Related p53 Gene, Press Release: Mar. 27, 1998, http://www.sequenom.com/pressrelease.htm.

$M^1, M^2$ or $M^3 =$ H, OH, XR, R, Halogen, $N_3$
$M^4 =$ OH, SH, $BH_2$
M = O, S, NH, BH

MASS MODIFYING FUNCTIONALITY R (X SIMILAR TO FIG. 8):

H

Alkyl: $-(CH_2)_r-CH_3$ e.g. $-CH_3$, $-C_2H_5$, and branched e.g. $-CH_3CH_2$)

$ICH_2(CH_2)_r-O-H$ 2,3-Epoxy-1-propanol $-(CH_2)_m-CH_2-O-H$ $-(CH_2)_m-CH_2-O-Alkyl$ $-(CH_2CH_2NH)_m-CH_2CH_2-NH_2$ $-[NH-(CH_2)_r-NH-\underset{\underset{O}{\|}}{C}-(CH_2)_r-\underset{\underset{O}{\|}}{C}-]_m-NH-(CH_2)_r-NH-\underset{\underset{O}{\|}}{C}-(CH_2)_r-\underset{\underset{O}{\|}}{C}-OH$ $-[NH(CH_2)_r-\underset{\underset{O}{\|}}{C}-]_m-NH-(CH_2)_r-\underset{\underset{O}{\|}}{C}-OH$ $-[NH-CHY-\underset{\underset{O}{\|}}{C}-]_m-NH-CHY-\underset{\underset{O}{\|}}{C}-OH$ $-[O-(CH_2)_r-\underset{\underset{O}{\|}}{C}-]_m-O-(CH_2)_r-\underset{\underset{O}{\|}}{C}-OH$ $-S-$ $-Si(Alkyl)_3$ $-Halogen$ $-N_3$ $-CH_2F$, $-CHF_2$, $-CF_3$

```
5'-dTAACGGTCATTACGGCCATTGACTGTAGGACCTGCATTACATGACTAGCT
   dTAACGGTCATTACGGCCATTGACTGTAGGACCTGCATTACATGACTAGC        pdT
   dTAACGGTCATTACGGCCATTGACTGTAGGACCTGCATTACATGACTAG         pdC
   dTAACGGTCATTACGGCCATTGACTGTAGGACCTGCATTACATGACTA          pdG
   dTAACGGTCATTACGGCCATTGACTGTAGGACCTGCATTACATGACT           pdA
   dTAACGGTCATTACGGCCATTGACTGTAGGACCTGCATTACATGAC            pdT
   dTAACGGTCATTACGGCCATTGACTGTAGGACCTGCATTACATGA             pdC
   dTAACGGTCATTACGGCCATTGACTGTAGGACCTGCATTACATG              pdA
   dTAACGGTCATTACGGCCATTGACTGTAGGACCTGCATTACAT               pdG
   dTAACGGTCATTACGGCCATTGACTGTAGGACCTGCATTACA                pdT
   dTAACGGTCATTACGGCCATTGACTGTAGGACCTGCATTAC                 pdA
   dTAACGGTCATTACGGCCATTGACTGTAGGACCTGCATTA                  pdC
   dTAACGGTCATTACGGCCATTGACTGTAGGACCTGCATT                   pdA
   dTAACGGTCATTACGGCCATTGACTGTAGGACCTGCAT                    pdT
   dTAACGGTCATTACGGCCATTGACTGTAGGACCTGCA                     pdT
   dTAACGGTCATTACGGCCATTGACTGTAGGACCTGC                      pdA
   dTAACGGTCATTACGGCCATTGACTGTAGGACCTG                       pdC
   dTAACGGTCATTACGGCCATTGACTGTAGGACCT                        pdG
   dTAACGGTCATTACGGCCATTGACTGTAGGACC                         pdT
   dTAACGGTCATTACGGCCATTGACTGTAGGAC                          pdC
   dTAACGGTCATTACGGCCATTGACTGTAGGA                           pdC
   dTAACGGTCATTACGGCCATTGACTGTAGG                            pdA
   dTAACGGTCATTACGGCCATTGACTGTAG                             pdG
   dTAACGGTCATTACGGCCATTGACTGTA                              pdG
   dTAACGGTCATTACGGCCATTGACTGT                               pdA
   dTAACGGTCATTACGGCCATTGACTG                                pdT
   dTAACGGTCATTACGGCCATTGACT                                 pdG
   dTAACGGTCATTACGGCCATTGAC                                  pdT
   dTAACGGTCATTACGGCCATTGA                                   pdC
   dTAACGGTCATTACGGCCATTG                                    pdA
   dTAACGGTCATTACGGCCATT                                     pdG
   dTAACGGTCATTACGGCCAT                                      pdT
   dTAACGGTCATTACGGCCA                                       pdT
   dTAACGGTCATTACGGCC                                        pdA
   dTAACGGTCATTACGGA                                         pdC
   dTAACGGTCATTACGG                                          pdA
   dTAACGGTCATTACG                                           pdG
   dTAACCGTCATTAC                                            pdG
   dTAACGGTCATTA                                             pdC
   dTAACGGTCATT                                              pdA
   dTAACGGTCAT                                               pdT
   dTAACGGTCA                                                pdT
   dTAACGGTC                                                 pdA
   dTAACGGT                                                  pdC
   dTAACGG                                                   pdT
   dTAACG                                                    pdG
   dTAAC                                                     pdG
   dTAA                                                      pdC
   dTA                                                       pdA
   dT                                                        pdA
                                                             pdT
```

FIG. 15

```
5'-dTAACGGTCATTACGGCCATTGACTGTAGGACCTGCATTACATGACTAGCT
   dTAACGGTCATTACGGCCATTGACTGTAGGACCTGCATTACATGACTAGC
   dTAACGGTCATTACGGCCATTGACTGTAGGACCTGCATTACATGACTAG
   dTAACGGTCATTACGGCCATTGACTGTAGGACCTGCATTACATGACTA
   dTAACGGTCATTACGGCCATTGACTGTAGGACCTGCATTACATGACT
   dTAACGGTCATTACGGCCATTGACTGTAGGACCTGCATTACATGAC
   dTAACGGTCATTACGGCCATTGACTGTAGGACCTGCATTACATGA
   dTAACGGTCATTACGGCCATTGACTGTAGGACCTGCATTACATG
   dTAACGGTCATTACGGCCATTGACTGTAGGACCTGCATTACAT
   dTAACGGTCATTACGGCCATTGACTGTAGGACCTGCATTACA
   dTAACGGTCATTACGGCCATTGACTGTAGGACCTGCATTAC
   dTAACGGTCATTACGGCCATTGACTGTAGGACCTGCATTA
   dTAACGGTCATTACGGCCATTGACTGTAGGACCTGCATT
   dTAACGGTCATTACGGCCATTGACTGTAGGACCTGCAT
   dTAACGGTCATTACGGCCATTGACTGTAGGACCTGCA
   dTAACGGTCATTACGGCCATTGACTGTAGGACCTGC
   dTAACGGTCATTACGGCCATTGACTGTAGGACCTG
   dTAACGGTCATTACGGCCATTGACTGTAGGACCT
   dTAACGGTCATTACGGCCATTGACTGTAGGACC
   dTAACGGTCATTACGGCCATTGACTGTAGGAC
   dTAACGGTCATTACGGCCATTGACTGTAGGA
   dTAACGGTCATTACGGCCATTGACTGTAGG
   dTAACGGTCATTACGGCCATTGACTGTAG
   dTAACGGTCATTACGGCCATTGACTGTA
   dTAACGGTCATTACGGCCATTGACTGT
   dTAACGGTCATTACGGCCATTGACTG
   dTAACGGTCATTACGGCCATTGACT
   dTAACGGTCATTACGGCCATTGAC
   dTAACGGTCATTACGGCCATTGA
   dTAACGGTCATTACGGCCATTG
   dTAACGGTCATTACGGCCATT
   dTAACGGTCATTACGGCCAT
   dTAACGGTCATTACGGCCA
   dTAACGGTCATTACGGCC
   dTAACGGTCATTACGGA
   dTAACGGTCATTACGG
   dTAACGGTCATTACG
   dTAACCGTCATTAC
   dTAACGGTCATTA
   dTAACGGTCATT
   dTAACGGTCAT
   dTAACGGTCA
   dTAACGGTC
   dTAACGGT
   dTAACGG
   dTAACG
   dTAAC
   dTAA
   dTA
   dT
```

*FIG. 16*

| Sequence | [M+H]+ | Peak Val. |
|---:|---:|---:|
| AGTC-3' | 1174.8 | 1174.7 |
| AAGTC-3' | 1488.0 | 1487.9 |
| GAAGTC-3' | 1817.2 | 1817.5 |
| TGAAGTC-3' | 2121.4 | 2121.3 |
| CTGAAGTC-3' | 2410.6 | 2410.2 |
| CCTGAAGTC-3' | 2699.8 | 2669.7 |
| TCCTGAAGTC-3' | 3004.0 | 3004.4 |
| GTCCTGAAGTC-3' | 3333.2 | 3333.0 |
| AGTCCTGAAGTC-3' | 3646.4 | 3647.0 |
| AAGTCCTGAAGTC-3' | 3959.6 | 3960.0 |
| GAAGTCCTGAAGTC-3' | 4288.8 | 4289.9 |
| TGAAGTCCTGAAGTC-3' | 4593.0 | 4592.9 |
| CTGAAGTCCTGAAGTC-3' | 4882.2 | 4882.0 |
| CCTGAAGTCCTGAAGTC-3' | 5171.4 | 5170.7 |
| TCCTGAAGTCCTGAAGTC-3' | 5475.6 | 5475.7 |
| GTCCTGAAGTCCTGAAGTC-3' | 5804.8 | 5805.4 |
| AGTCCTGAAGTCCTGAAGTC-3' | 6118.0 | 6117.5 |
| CAGTCCTGAAGTCCTGAAGTC-3' | 6407.2 | 6408.0 |
| TCAGTCCTGAAGTCCTGAAGTC-3' | 6711.4 | 6712.6 |
| GTCAGTCCTGAAGTCCTGAAGTC-3' | 7040.6 | 7041.3 |
| AGTCAGTCCTGAAGTCCTGAAGTC-3' | 7353.8 | 7353.9 |
| AAGTCAGTCCTGAAGTCCTGAAGTC-3' | 7667.0 | 7669.6 |
| GAAGTCAGTCCTGAAGTCCTGAAGTC-3' | 7996.2 | 7995.0 |
| TGAAGTCAGTCCTGAAGTCCTGAAGTC-3' | 8300.4 | 8302.8 |
| CTGAAGTCAGTCCTGAAGTCCTGAAGTC-3' | 8589.6 | 8589.0 |
| CCTGAAGTCAGTCCTGAAGTCCTGAAGTC-3' | 8878.8 | 8878.2 |
| TCCTGAAGTCAGTCCTGAAGTCCTGAAGTC-3' | 9183.0 | 9184.3 |
| GTCCTGAAGTCAGTCCTGAAGTCCTGAAGTC-3' | 9512.2 | 9512.0 |

*FIG. 17D-1*

| Sequence | [M+H]+ | Peak Val. |
|---|---|---|
| AGTCCTGAAGTCAGTCCTGAAGTCCTGAAGTCCTGAAGTC-3' | 9825.4 | 9825.5 |
| AAGTCCTGAAGTCAGTCCTGAAGTCCTGAAGTCCTGAAGTC-3' | 10138.6 | 10139.6 |
| GAAGTCCTGAAGTCAGTCCTGAAGTCCTGAAGTCCTGAAGTC-3' | 10467.8 | 10468.5 |
| TGAAGTCCTGAAGTCAGTCCTGAAGTCCTGAAGTCCTGAAGTC-3' | 10772.0 | 10772.1 |
| CTGAAGTCCTGAAGTCAGTCCTGAAGTCCTGAAGTCCTGAAGTC-3' | 11061.2 | 11061.9 |
| CCTGAAGTCCTGAAGTCAGTCCTGAAGTCCTGAAGTCCTGAAGTC-3' | 11350.4 | 11349.4 |
| TCCTGAAGTCCTGAAGTCAGTCCTGAAGTCCTGAAGTCCTGAAGTC-3' | 11654.6 | 11653.6 |
| GTCCTGAAGTCCTGAAGTCAGTCCTGAAGTCCTGAAGTCCTGAAGTC-3' | 11983.8 | 11984.2 |
| AGTCCTGAAGTCCTGAAGTCAGTCCTGAAGTCCTGAAGTCCTGAAGTC-3' | 12297.0 | 12296.4 |
| CAGTCCTGAAGTCCTGAAGTCAGTCCTGAAGTCCTGAAGTCCTGAAGTC-3' | 12586.2 | 12586.1 |
| TCAGTCCTGAAGTCCTGAAGTCAGTCCTGAAGTCCTGAAGTCCTGAAGTC-3' | 12890.4 | 12889.3 |
| GTCAGTCCTGAAGTCCTGAAGTCAGTCCTGAAGTCCTGAAGTCCTGAAGTC-3' | 13219.6 | 13221.2 |
| AGTCAGTCCTGAAGTCCTGAAGTCAGTCCTGAAGTCCTGAAGTCCTGAAGTC-3' | 13532.8 | 13532.8 |
| AAGTCAGTCCTGAAGTCCTGAAGTCAGTCCTGAAGTCCTGAAGTCCTGAAGTC-3' | 13846.0 | 13843.8 |
| GAAGTCAGTCCTGAAGTCCTGAAGTCAGTCCTGAAGTCCTGAAGTCCTGAAGTC-3' | 14175.2 | 14176.2 |
| TGAAGTCAGTCCTGAAGTCCTGAAGTCAGTCCTGAAGTCCTGAAGTCCTGAAGTC-3' | 14479.4 | 14481.5 |
| CTGAAGTCAGTCCTGAAGTCCTGAAGTCAGTCCTGAAGTCCTGAAGTCCTGAAGTC-3' | 14768.6 | 14768.0 |
| CCTGAAGTCAGTCCTGAAGTCCTGAAGTCAGTCCTGAAGTCCTGAAGTCCTGAAGTC-3' | 15057.6 | 15054.4* |
| TCCTGAAGTCAGTCCTGAAGTCCTGAAGTCAGTCCTGAAGTCCTGAAGTCCTGAAGTC-3' | 15362.0 | 15369.5* |
| GTCCTGAAGTCAGTCCTGAAGTCCTGAAGTCAGTCCTGAAGTCCTGAAGTCCTGAAGTC-3' | 15691.2 | 15699.0* |
| AGTCCTGAAGTCAGTCCTGAAGTCCTGAAGTCAGTCCTGAAGTCCTGAAGTCCTGAAGTC-3' | 16004.4 | 16009.9* |
| AAGTCCTGAAGTCAGTCCTGAAGTCCTGAAGTCAGTCCTGAAGTCCTGAAGTCCTGAAGTC-3' | 16317.6 | 16316.8* |
| GAAGTCCTGAAGTCAGTCCTGAAGTCCTGAAGTCAGTCCTGAAGTCCTGAAGTCCTGAAGTC-3' | 16646.8 | 16641.0* |
| TGAAGTCCTGAAGTCAGTCCTGAAGTCCTGAAGTCAGTCCTGAAGTCCTGAAGTCCTGAAGTC-3' | 16951.0 | 16957.1* |
| CTGAAGTCCTGAAGTCAGTCCTGAAGTCCTGAAGTCAGTCCTGAAGTCCTGAAGTCCTGAAGTC-3' | 17240.2 | 17239.0* |
| CCTGAAGTCCTGAAGTCAGTCCTGAAGTCCTGAAGTCAGTCCTGAAGTCCTGAAGTCCTGAAGTC-3' | 17529.4 | N/D |
| TCCTGAAGTCCTGAAGTCAGTCCTGAAGTCCTGAAGTCAGTCCTGAAGTCCTGAAGTCCTGAAGTC-3' | 17833.6 | 17832.6* |
| GTCCTGAAGTCCTGAAGTCAGTCCTGAAGTCCTGAAGTCAGTCCTGAAGTCCTGAAGTCCTGAAGTC-3' | 18162.8 | 18166.3* |
| AGTCCTGAAGTCCTGAAGTCAGTCCTGAAGTCCTGAAGTCAGTCCTGAAGTCCTGAAGTCCTGAAGTC-3' | 18476.0 | 18476.5 |

*FIG. 17D-2*

```
5'-dTAACGGTCATTACGGCCATTGACTGTAGGACCTGCATTACATGACTAGCT
   dTAACGGTCATTACGGCCATTGACTGTAGGACCTGCATTACATGACT
   dTAACGGTCATTACGGCCATTGACTGTAGGACCTGCATTACAT
   dTAACGGTCATTACGGCCATTGACTGTAGGACCTGCATT
   dTAACGGTCATTACGGCCATTGACTGTAGGACCTGCAT
   dTAACGGTCATTACGGCCATTGACTGTAGGACCT
   dTAACGGTCATTACGGCCATTGACTGT
   dTAACGGTCATTACGGCCATTGACT
   dTAACGGTCATTACGGCCATT
   dTAACGGTCATTACGGCCAT
   dTAACGGTCATT
   dTAACGGTCAT
   dTAACGGT
   dT
5'-dTAACGGTCATTACGGCCATTGACTGTAGGACCTGCATTACATGACTAGC
   dTAACGGTCATTACGGCCATTGACTGTAGGACCTGCATTACATGAC
   dTAACGGTCATTACGGCCATTGACTGTAGGACCTGCATTAC
   dTAACGGTCATTACGGCCATTGACTGTAGGACCTGC
   dTAACGGTCATTACGGCCATTGACTGTAGGACC
   dTAACGGTCATTACGGCCATTGACTGTAGGAC
   dTAACGGTCATTACGGCCATTGAC
   dTAACGGTCATTACGGCC
   dTAACGGTCATTACGGC
   dTAACGGTCATTAC
   dTAACGGTC
   dTAAC
5'-dTAACGGTCATTACGGCCATTGACTGTAGGACCTGCATTACATGACTA
   dTAACGGTCATTACGGCCATTGACTGTAGGACCTGCATTACATGA
   dTAACGGTCATTACGGCCATTGACTGTAGGACCTGCATTACA
   dTAACGGTCATTACGGCCATTGACTGTAGGACCTGCATTA
   dTAACGGTCATTACGGCCATTGACTGTAGGACCTGCA
   dTAACGGTCATTACGGCCATTGACTGTAGGA
   dTAACGGTCATTACGGCCATTGACTGTA
   dTAACGGTCATTACGGCCATTGA
   dTAACGGTCATTACGGCCA
   dTAACGGTCATTA
   dTAACGGTCA
   dTAA
   dTA
5'-dTAACGGTCATTACGGCCATTGACTGTAGGACCTGCATTACATGACTAG
   dTAACGGTCATTACGGCCATTGACTGTAGGACCTGCATTACATG
   dTAACGGTCATTACGGCCATTGACTGTAGGACCTG
   dTAACGGTCATTACGGCCATTGACTGTAGG
   dTAACGGTCATTACGGCCATTGACTGTAG
   dTAACGGTCATTACGGCCATTGACTG
   dTAACGGTCATTACGGCCATTG
   dTAACGGTCATTACGG
   dTAACGGTCATTACG
   dTAACGG
   dTAACG
```

*FIG. 18*

DNA SEQUENCING BY MASS SPECTROMETRY VIA EXONUCLEASE DEGRADATION

RELATED APPLICATIONS

This application is a continuation of U.S. application Ser. No. 08/744,590, filed Nov. 6, 1996, now allowed, which is a continuation-in-part of U.S. application Ser. No. 08/388,171, filed Feb. 10, 1995, now U.S. Pat. No. 5,622,824, which is a file wrapper continuation (FWC) of U.S. application Ser. No. 08/034,738, filed Mar. 19, 1993, now abandoned. This application is a continuation-in-part of U.S. application Ser. No. 08/388,171, filed Feb. 10, 1995, now U.S. Pat. No. 5,622,824, and also U.S. application Ser. No. 08/034,738. The subject matter of each of U.S. application Ser. No. 08/388,171, U.S. application Ser. No. 08/744,590, and U.S. application Ser. No. 08/034,738 is incorporated by reference.

BACKGROUND OF THE INVENTION

The fundamental role that determining DNA sequences has for the life sciences is evident. Its importance in the human genome project has been discussed and published widely [e.g. J. E. Bishop and M. Waldholz, 1991, Genome. The Story of the Most Astonishing Scientific Adventure of Our Time—The Attempt to Map All Genes in the Human Body, Simon & Schuster, New York].

The current state-of-the-art in DNA sequencing is summarized in recent review articles [e.g. B. Barrell, *The FASEB Journal*, 5, 40 (1991); G. L. Trainor, *Anal. Chem.* 62, 418 (1990), and references cited therein]. The most widely used DNA sequencing chemistry is the enzymatic chain termination method [F. Sanger et al., *Proc. Natl. Acad. Sci. USA*, 74, 5463 (1977)] which has been adopted for several different sequencing strategies. The sequencing reactions are either performed in solution with the use of different DNA polymerases, such as the thermophilic Taq DNA polymerase [M. A. Innes, *Proc. Natl. Acad. Sci. USA*, 85: 9436 (1988)] or specially modified T7 DNA polymerase ("SEQUENASE") [S. Tabor and C.C. Richardson, *Proc. Natl. Acad. Sci. USA*, 84, 4767 (1987)], or in conjunction with the use of polymer supports. See for example S. Stahl et al., *Nucleic Acids Res.*, 16, 3025 (1988); M. Uhlen, PCT Application WO 89/09282; Cocuzza et al., PCT Application WO 91/11533; and Jones et al., PCT Application WO 92/03575, incorporated by reference herein.

A central, but at the same time limiting part of almost all sequencing strategies used today is the separation of the base-specifically terminated nested fragment families by polyacrylamide gel electrophoresis (PAGE). This method is time-consuming and error-prone and can result in ambiguous sequence determinations. As a consequence of the use of PAGE, highly experienced personnel are often required for the interpretation of the sequence ladders obtained by PAGE in order to get reliable results. Automatic sequence readers very often are unable to handle artefacts such as "smiling", compressions, faint ghost bands, etc. This is true for the standard detection methods employing radioactive labeling such as $32_P$, $33_P$ or $35_S$, as well as for the so-called Automatic DNA Sequencers (e.g. Applied Biosystems, Millipore, DuPont, Pharmacia) using fluorescent dyes for the detection of the sequencing bands.

Apart from the time factor, the biggest limitations of all methods involving PAGE as an integral part, however, is the generation of reliable sequence information, and the transformation of this information into a computer format to facilitate sophisticated analysis of the sequence data utilizing existing software and DNA sequence and protein sequence data banks.

With standard Sanger sequencing, 200 to 500 bases of unconfirmed sequence information can be obtained in about 24 hours; with automatic DNA sequencers this number can be multiplied by approximately a factor of 10 to 20 due to processing several samples simultaneously. A further increase in throughput can be achieved by employing multiplex DNA sequencing [G. Church et al., *Science*, 240, 185–188 (1988); Köster et al., *Nucleic Acids Res. Symposium Ser.* No. 24, 318–21 (1991)] in which, by using a unique tag sequence, several sequencing ladders can be detected, one after the other, from the same PAGE after blotting, UV-crosslinking to a membrane, and hybridizations with specific complementary tag probes. However, this approach is still very laborious, often requires highly skilled personnel and can be hampered by the use of PAGE as a key element of the whole process.

A large scale sequencing project often starts with either a cDNA or genomic library of large DNA fragments inserted in suitable cloning vectors such as cosmid, plasmid (e.g. pUC), phagemid (e.g. pEMBL, pGEM) or single-stranded phage (e.g. M13) vectors [T. Maniatis, E. F. Fritsch and J. Sambrook (1982) Molecular Cloning. A Laboratory Manual. Cold Spring Harbor Laboratory, Cold Spring Harbor, N.Y.; Methods in Enzymology, Vol. 101 (1983), Recombinant DNA, Part C; Vol. 153 (1987), Recombinant DNA, Part D; Vol. 154 (1987), Recombinant DNA, Part E; Vol. 155 (1987), Recombinant DNA, Part F and Vol. 152 (1987), Guide to Molecular Cloning Techniques, Academic Press, New York]. Since large DNA fragments currently cannot be sequenced directly in one run because the Sanger sequencing chemistry allows only about 200 to 500 bases to be read at a time, the long DNA fragments have to be cut into shorter pieces which are separately sequenced. In one approach this is done in a fully random manner by using, for example, nonspecific DNAse I digestion, frequently cutting restriction enzymes, or sonification, and sorting by electrophoresis on agarose gels [*Methods in Enzymology*, supra]. However, this method is time-consuming and often not economical as several sequences are sequenced many times until a contiguous DNA sequence is obtained. Very often the expenditure of work to close the gaps of the total sequence is enormous. Consequently, it is desirable to have a method which allows sequencing of a long DNA fragment in a non-random, i.e. direct, way from one end through to the other. Several strategies have been proposed to achieve this [*Methods of Enzymology*, supra; S. Henikoff, *Gene*, 28, 351–59 (1984); S. Henikoff, et al. U.S. Pat. No. 4,843,003; and PCT Application WO 91/12341]. However, none of the currently available sequencing methods provide an acceptable method of sequencing megabase DNA sequences in either a timely or economical manner. The main reason for this stems from the use of PAGE as a central and key element of the overall process.

In PAGE, under denaturing conditions, the nested families of terminated DNA fragments are separated by the different mobilities of DNA chains of different length. A closer inspection, however, reveals that it is not the chain length alone which governs the mobility of DNA chains by PAGE, but there is a significant influence of base composition on the mobility [R. Frank and H. Köster, *Nucleic Acids Res.*, 6, 2069 (1979)]. PAGE, therefore, is not only a very slow, but also an unreliable method for the determination of molecular weights, as DNA fragments of the same length but different sequence/base composition could have different mobilities.

Likewise, DNA sequences which have the same mobility could have different sequence/base compositions.

The most reliable way for the determination of the sequence/base composition of a given DNA fragment would, therefore, be to correlate the sequence with its molecular weight. Mass spectrometry is capable of doing this. The enormous advantage of mass spectrometry compared to the above mentioned methods is the speed, which is in the range of seconds per analysis, and the accuracy of mass determination, as well as the possibility to directly read the collected mass data into a computer. The application of mass spectrometry for DNA sequencing has been investigated by several groups [e.g. *Methods in Enzymology*, Vol. 193: Mass Spectrometry, (J. A. McCloskey, editor), 1990, Academic Press, New York; K. H. Schramm *Biomedical Applications of Mass Spectrometry*, 34, 203–287 (1990); P. F. Crain *Mass Spectrometry Reviews*, 9, 505 (1990)].

Most of the attempts to use mass spectrometry to sequence DNA have used stable isotopes for base-specific labeling, as for instance the four sulfur isotopes $^{32}S$, $^{33}S$, $^{34}S$ and $^{36}S$. See, for example, Brennan et al., PCT Application WO 89/12694, R. L. Mills U.S. Pat. No. 5,064,754, U.S. Pat. No. 5,002,868, Jacobson et al.; Haan European Patent Application No. A1 0360676. Most of these methods employed the Sanger sequencing chemistry and polyacrylamide gel electrophoresis with some variations, such as capillary zone electrophoresis (CZE), to separate the nested, terminated DNA fragments prior to mass spectrometric analysis, which, jeopardizes, to some extent, the advantages of mass spectrometry.

One advantage of PAGE is that it is a parallel method, i.e. several samples can be analyzed simultaneously (though this is not true for CZE which is a serial method), whereas mass spectrometry allows, in general, only a serial handling of the samples. In U.S. Pat. No. 5,547,835, mass spectrometric DNA sequencing is proposed without the use of PAGE, employing desorption/ionization techniques applicable to larger biopolymers, such as electrospray (ES) [J. B. Fenn et al., *J. Phys. Chem.*, 88, 4451–59 (1984); Fenn et al., PCT Application No. WO 90/14148; and B. Ardrey, *Spectroscopy Europe*, 4, 10–18 (1992)] and matrix-assisted laser desorption/ionization (MALDI) mass spectrometry [F. Hillenkamp et al., Laser Desorption Mass Spectrometry, Part I: Mechanisms and Techniques and Part II: Performance and Application of MALDI of Large Biomolecules, in *Mass Spectrometry in the Biological Sciences: A Tutorial*(M. L. Gross, editor), 165–197 (1992), Kluwer Academic Publishers, The Netherlands] which can facilitate determination of DNA sequences by direct measurement of the molecular masses in the mixture of base-specifically terminated nested DNA fragments. By integrating the concept of multiplexing through the use of mass-modified nucleoside triphosphate derivatives, the serial mode of analysis typical for current mass spectrometric methods can be changed to a parallel mode [H. Köster, U.S. Pat. No. 5,547,835, supra].

MALDI and ES mass spectrometry are in some aspects complementary techniques. While ES, using an atmospheric pressure ionization interface (API), can accommodate continuous flow streams from high-performance liquid chromatoghraphs (HPLC) [K. B. Tomer, et al. *Biological Mass Spectrometry*, 20, 783–88 (1991)] and capillary zone electrophoresis (CZE) [R. D. Smith et al., *Anal. Chem.*, 60, 436–41 (1988)] this is currently not available for MALDI mass spectrometry. On the other hand, MALDI mass spectrometry is less sensitive to buffer salts and other low molecular weight components in the analysis of larger molecules with a TOF mass analyzer [Hillenkamp et al. (1992), supra]; in contrast, ES is very sensitive to by-products of low volatility. While the high mass range in ES mass spectrometry is accessible through the formation of multiply charged molecular ions, this is achieved in MALDI mass spectrometry by applying a time-of-flight (TOF) mass analyzer and the assistance of an appropriate matrix to volatilize the biomolecules. Similar to ES, a thermospray interface has been used to couple HPLC on-line with a mass analyzer. Nucleosides originating from enzymatic hydrolysates have been analyzed using such a configuration [C. G. Edmonds et al. *Nucleic Acids Res.*, 13, 8197–8206 (1985)]. However, Edmonds et al. does not disclose a method for nucleic acid sequencing.

A complementary and completely different approach to determine the DNA sequence of a long DNA fragment would be to progressively degrade the DNA strand using exonucleases from one side,—nucleotide by nucleotide. This method has been proposed by Jett et al. See J. H. Jett et al. *J Biomolecular Structure & Dynamics*, 7, 301–309 (1989); and J. H. Jett et al. PCT Application No. WO 89/03432. A single molecule of a DNA or RNA fragment is suspended in a moving flow stream and contacted with an exonuclease which cleaves off one nucleotide after the other. Detection of the released nucleotides is accomplished by specifically labeling the four nucleotides with four different fluorescent dyes and involving laser-induced flow cytometric techniques.

However, strategies which use a stepwise enzymatic degradation process can suffer from problems relating to synchronization, i.e. the enzymatic reaction soon comes out of phase. Jett et al., supra, have attempted to address this problem by degrading just one single DNA or RNA molecule by an exonuclease. However, this approach is very hard, as handling a single molecule, keeping it in a moving flow stream, and achieving a sensitivity of detection which clearly identifies one single nucleotide are only some of the very difficult technical problems to be solved. In addition, in using fluorescent tags, the physical detection process for a fluorescent signal involves a time factor difficult to control and the necessity to employ excitation by lasers can cause photo-bleaching of the fluorescent signal. Another problem, which still needs to be resolved, is that DNA/RNA polymerases, which are able to use the four fluorescently labeled NTPs instead of the unmodified counterparts, have not been identified.

The invention described herein addresses most of the problems described above, which are inherent to currently existing DNA sequencing processes, and provides chemistries and systems suitable for high-speed DNA sequencing, a prerequisite for tackling the human genome and other genome sequencing projects.

SUMMARY OF THE INVENTION

In contrast to most sequencing strategies, the process of this invention does not use the Sanger sequencing chemistry, polyacrylamide gel electrophoresis or radioactive, fluorescent or chemiluminescent detection. Instead, the process of the invention adopts a direct sequencing approach, beginning with large DNA fragments cloned into conventional cloning vectors, and based on mass spectrometric detection. To achieve this, the target nucleic acid (or fragments of the target nucleic acid) is, by means of protection, specificity of enzymatic activity, or immobilization, unilaterally degraded in a stepwise manner via exonuclease digestion and the nucleotides, derivatives or truncated sequences detected are by mass spectrometry.

In one embodiment, prior to enzymatic degradation, sets of ordered deletions are made, which span the whole sequence of the cloned DNA fragment. In this manner, mass-modified nucleotides are incorporated using a combination of exonuclease and DNA/RNA polymerase. This enables either multiplex mass spectrometric detection, or modulation of the activity of the exonuclease so as to synchronize the degradative process.

In another embodiment of the invention, the phasing problem is resolved by continuously applying small quantities of the enzymatic reaction mixture onto a moving belt with adjustable speed for mass spectrometric detection.

In yet another embodiment of the invention, the throughput is further increased by applying reaction mixtures from different reactors simultaneously onto the moving belt. In this case, the different sets of sequencing reactions are identified by specific mass-modifying labels attached to the four nucleotides. Two-dimensional multiplexing can further increase the throughput of exonuclease-mediated mass spectrometric sequencing as described herein.

In further aspects, the invention features kits and devices for sequencing nucleic acids, based on the novel process described herein.

The enormous advantage of exonuclease-mediated mass spectrometric DNA sequencing is that small molecules are analyzed and identified by mass spectrometry. In this mass range, the accuracy of mass spectrometers is routinely very high; i.e. 0.1 mass units are easily detected. This increases the potential for multiplexing as small differences in mass can be detected and resolved. An additional advantage of mass spectrometric sequencing is that the identified masses can be registered automatically by a computer and, by adding the time coordinate, automatically aligned to sequences. Since the sequences so determined are memorized (i.e. saved to disk or resident in the computer memory), appropriate existing computer programs operating in a multitasking environment can be searching in the "background" (i.e. during continuous generation of new sequence data by the exonuclease mass spectrometric sequencer) for overlaps and generate contiguous sequence information which, via a link to a sequence data bank, can be used in homology searches, etc.

Other features and advantages of the invention will be further described with reference to the following Detailed Description and claims.

BRIEF DESCRIPTION OF THE DRAWINGS

FIG. 7 shows some possible functional groups (R) useful for either mass-modification of nucleotides in discrete increments for differentiation by mass spectrometry and/or to modulate the enzymatic activity of an exonuclease.

FIG. 15 is a schematic representation of one format of the invention in which a nucleic acid sequence is revealed through mass spectrometer determination of the molecular weights of sequentially and unilaterally (e.g. from the 5' or 3' end) released nucleotides (or nucleosides, e.g. generated by phosphatase treatment of nucleotides).

FIG. 16 is a schematic representation of another format of the invention in which the molecular weight of fragments remaining after exonuclease digestion are determined. Based on the incremental difference in molecular weight between neighboring fragments, the nucleic acid sequence of the complete molecule is deduced.

FIGS. 17D-1 and 17D-2 compares the theoretical mass values with the values found for each of the fragments in the mixture.

FIG. 18 is a schematic of another format of the invention, wherein four sets of base-specifically terminated fragments obtained via exonuclease treatment are superimposed to reveal the sequence of the nucleic acid molecule (i.e. reverse Sanger sequencing).

DETAILED DESCRIPTION OF THE INVENTION

The starting point for the process of the invention can be, for example, DNA cloned from either a genomic or cDNA library, or a piece of DNA isolated and amplified by polymerase chain reaction (PCR) which contains a DNA fragment of unknown sequence. Libraries can be obtained, for instance, by following standard procedures and cloning vectors [Maniatis, Fritsch and Sambrook (1982), supra; *Methods in Enzymology*, Vol. 101 (1983) and Vol. 152–155 (1987), supra]. Appropriate cloning vectors are also commercially available. As will be apparent, the invention is not limited to the use of any specific vector constructs or cloning procedures, but can be applied to any given DNA fragment whether obtained, for instance, by cloning in any vector or by the Polymerase Chain Reaction (PCR) or any DNA/RNA amplification method. The unknown DNA sequence can be obtained in either double-stranded form (e.g. using standard PCR) or in a single-stranded form (e.g. employing asymmetric PCR, *PCR Technology*: Principles and Applications for DNA Amplification (Erlich, editor), M. Stockton Press, New York (1989)).

For those skilled in the art it is clear that both DNA and RNA can be exonucleolytically degraded from either the 5' or 3' end depending upon the choice of exonuclease. Similarly the sequence of an unknown DNA molecule can be determined directly by exonuclease digestion, or alternatively, the DNA fragment of unknown sequence can be transcribed first into a complementary RNA copy which is subsequently exonucleolytically degraded to provide the RNA sequence. Appropriate vectors, such as the pGEM (Promega) vectors, are useful in the present invention as they have specific promoters for either the SP6 or T7 DNA-dependent RNA polymerases flanking the multiple cloning site. This feature allows transcription of both unknown DNA strands into complementary RNA for subsequent exonuclease sequencing. Furthermore, these vectors, belonging to the class of phagemid vectors, provide means to generate single-stranded DNA from the unknown, double stranded DNA. Thus, by using two vectors which differ only in the orientation of the f1 origin of replication, both strands of the unknown DNA sequence can be obtained in a single-stranded form and utilized for subsequent exonuclease sequencing. The scope of the invention is also not limited by the choice of restriction sites. There is, however, a preference for rare cutting restriction sites to keep the unknown DNA fragment unfragmented during the manipulations in preparation for exonuclease sequencing.

Figure 17A:
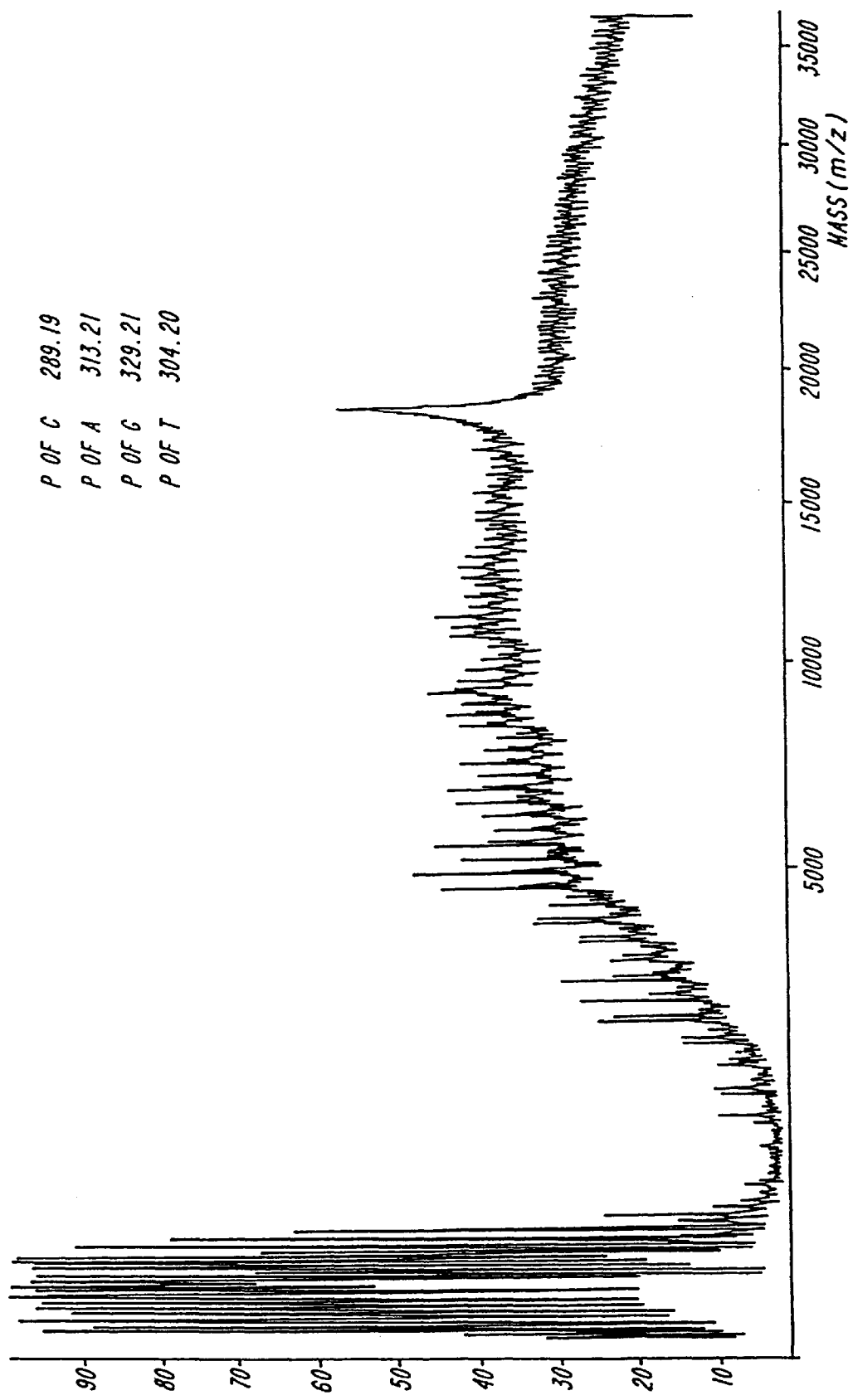
FIG. 17A shows the mass spectrum obtained from a 60-mer by MALDI-TOF mass spectrometry. The theoretical molecular weights for the four nucleotides are provided.
Figure 17B:
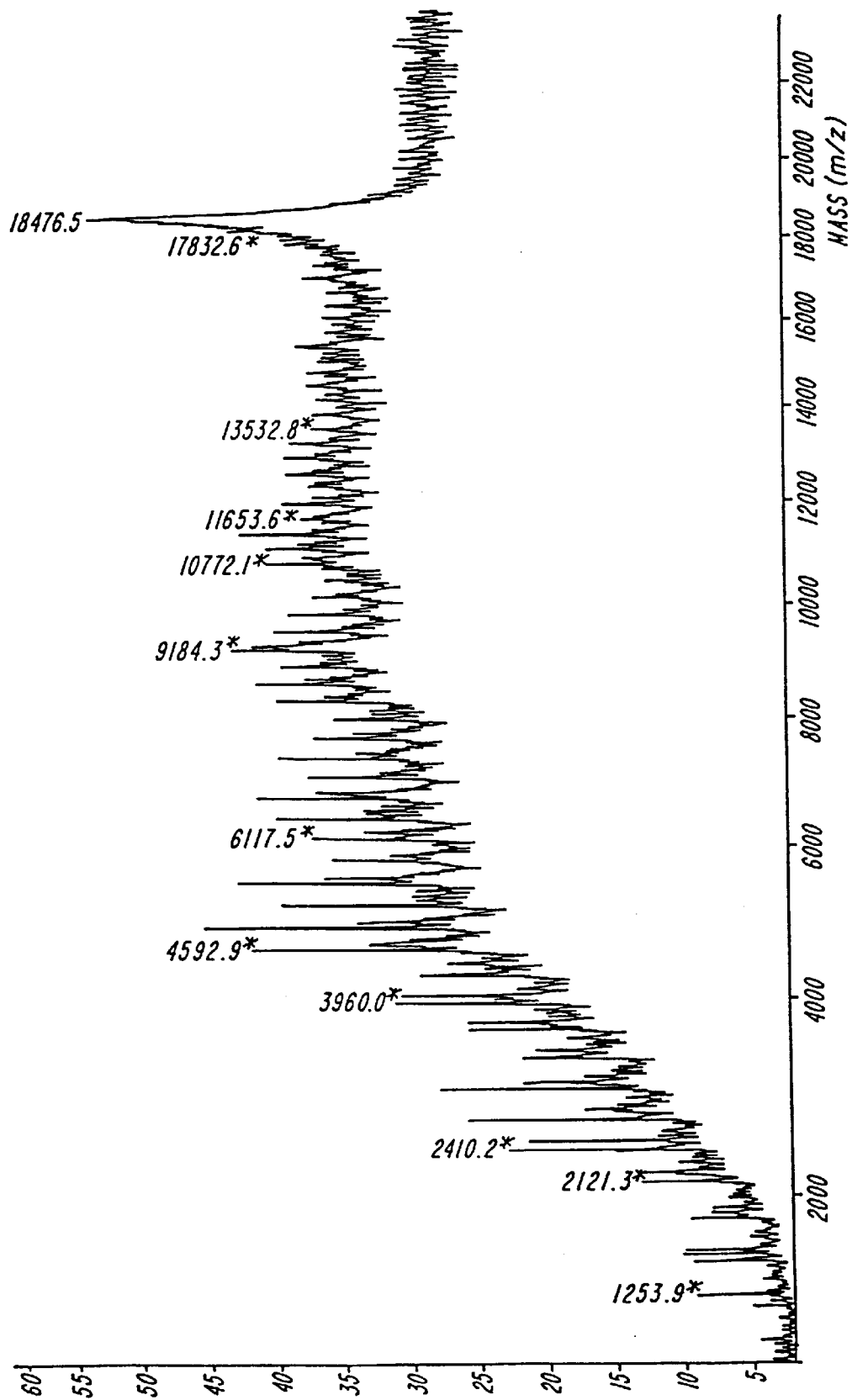
FIG. 17B provides an expanded version of FIG. 17A.
Figure 17C:
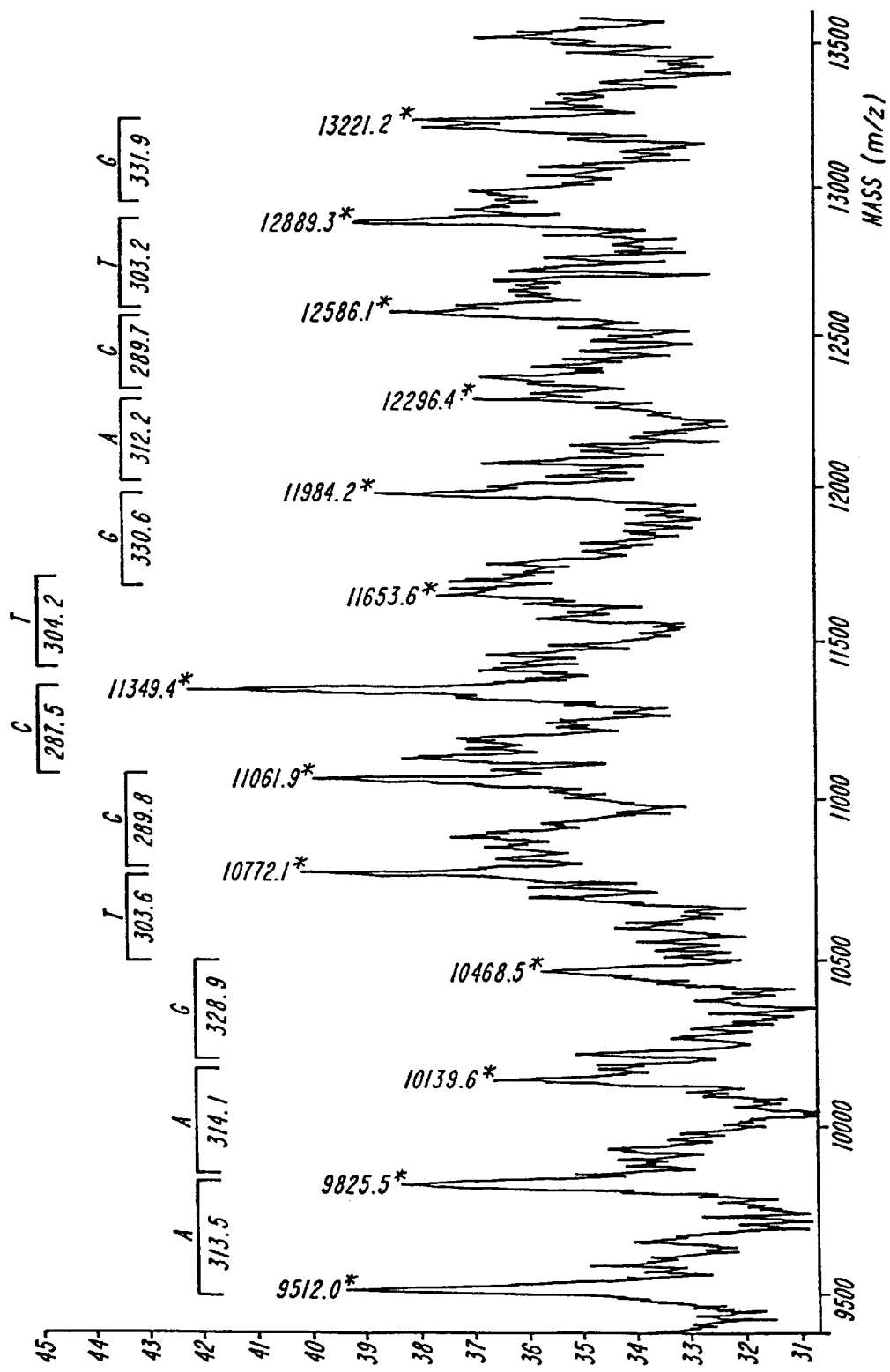
FIG. 17C provides a further expanded version of a sequence range between a 31-mer and a 43-mer.

In one aspect of the invention, the target nucleic acid (or fragments of the target nucleic acid) is, by means of protection, specificity of enzymatic activity, or immobilization, unilaterally degraded in a stepwise manner via exonuclease digestion, and the nucleotides, derivatives (FIG. 15) or truncated sequences (FIG. 16) detected by mass spectrometry. FIG. 17 demonstrates how molecular weights of the truncated fragments of the sequences of a 60-mer can be derived. FIGS. 20 and 21 demonstrate the power of mass spectrometric detection of nucleosides by either FAB (fast atomic bombardment) or ESI (electrospray ionization) mass spectrometry, respectively. Whereas UV or fluorescent measurements will not discriminate mixtures of the nucleoside/nucleotide which are generated when the enzyme gets out of phase, this is no problem with MS since the resolving power in differentiating between the molecular mass of dA, dT, dG and dC is more than significant. FIGS. 20 and 21 also showing that peak intensities are correlated with the amount of the nucleoside in the mixture. Thus, if the enzyme is getting out of phase, samples measured at consecutive time intervals will reveal the sequence of the nucleosides/nucleotides sequentially cleaved off by the exonuclease.

Figure 19:
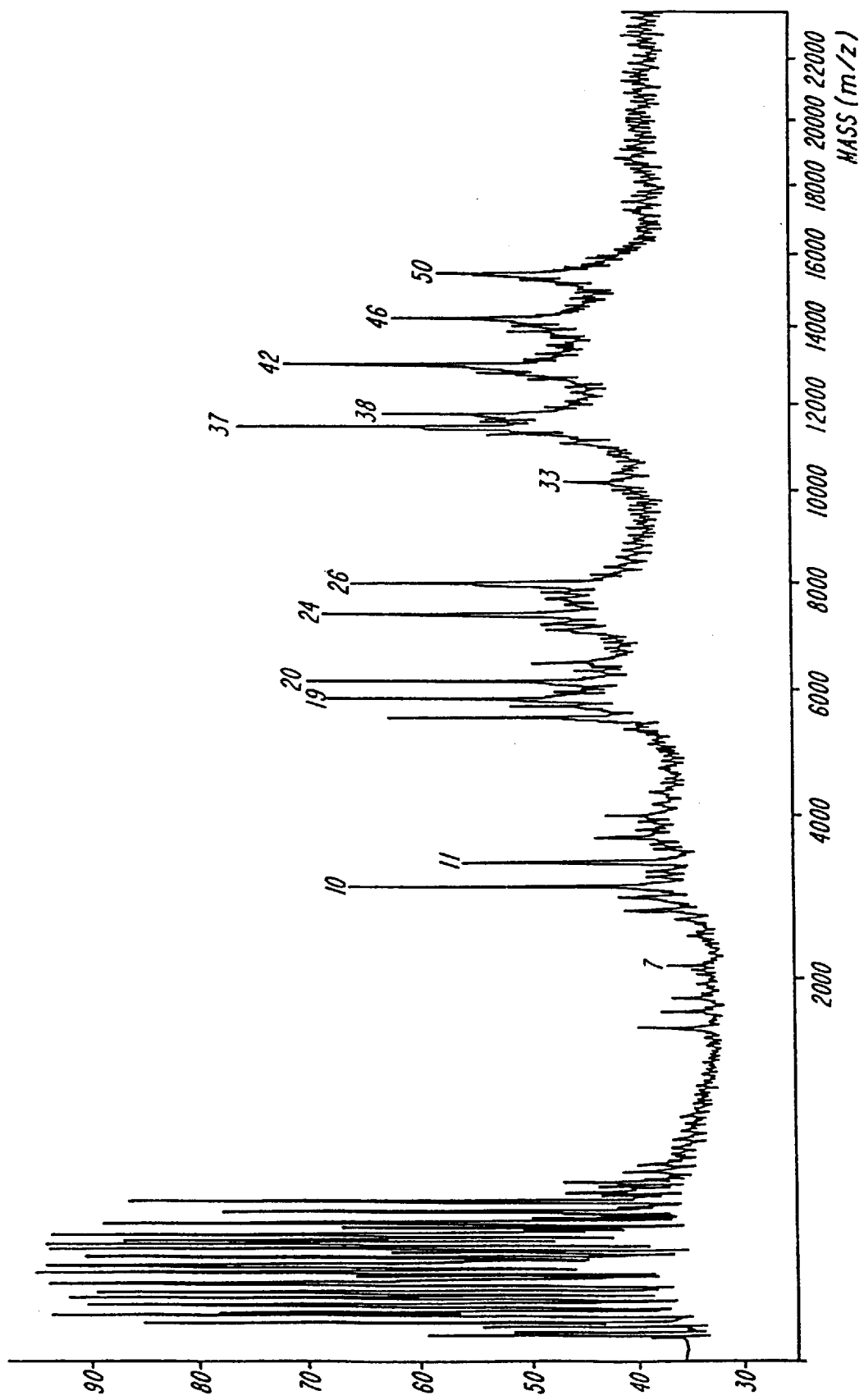
FIG. 19 provides a MALDI-TOF spectrum of the 14 fragments simulating the dT-terminated nested set of FIG. 18.
Figure 20A:
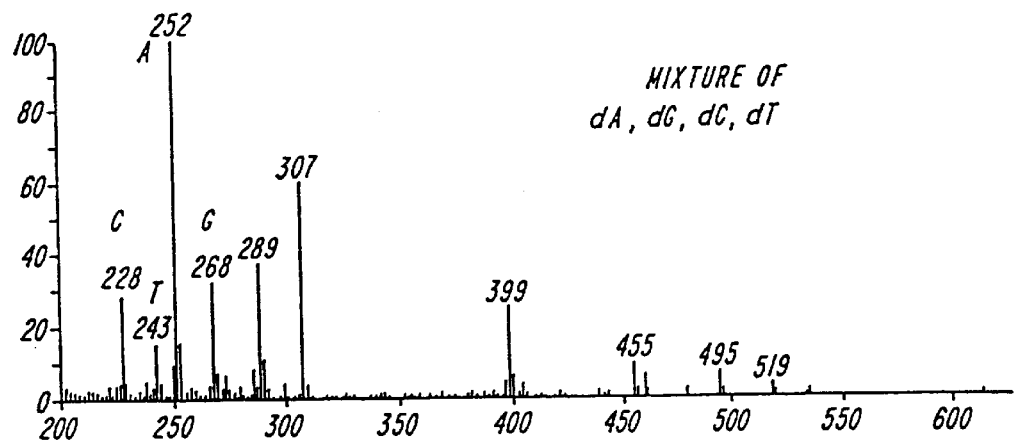
FIG. 20 provides Fast Atom Bombardment (FAB) spectra of three mixtures: (A) a 1:1:1:1 mixture of A:C:G:T; (B) a 1:1:1:0.5 mixture of A:C:G:T; (C) a 1:1:1:0.2 mixture of A:C:G:T;. and (D) matrix alone.
Figure 20B:
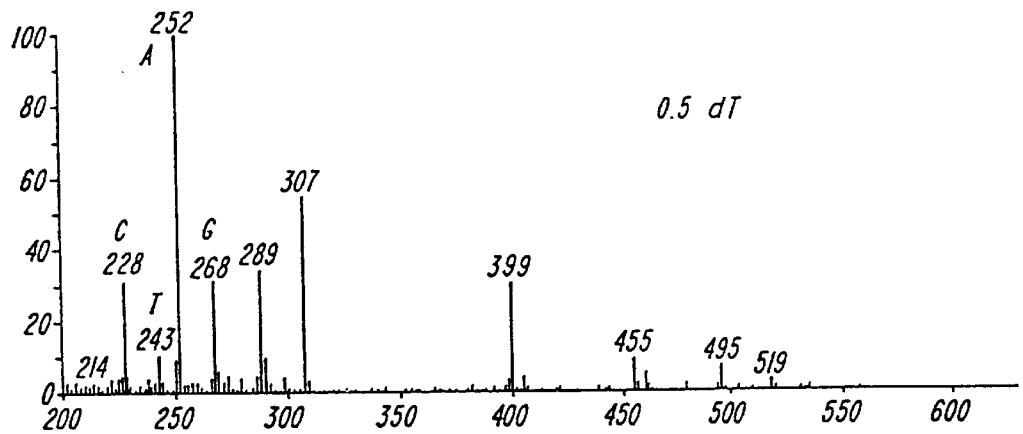
Figure 20C:
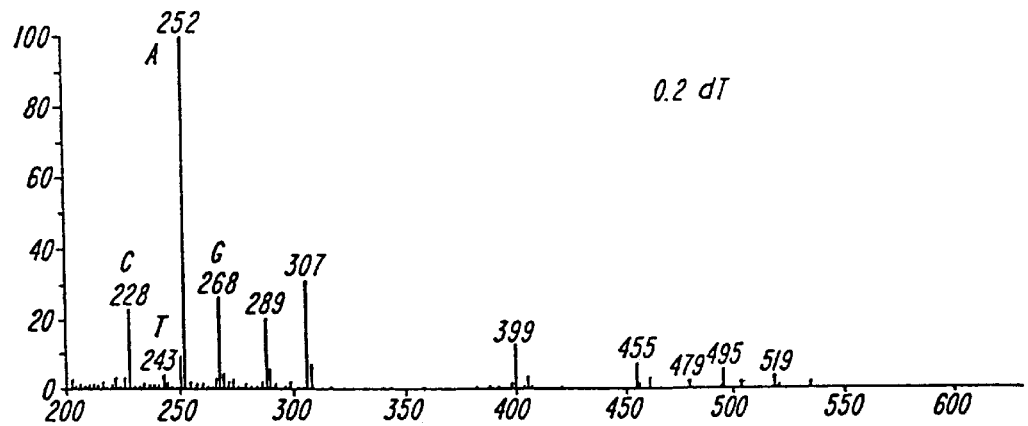
Figure 20D:
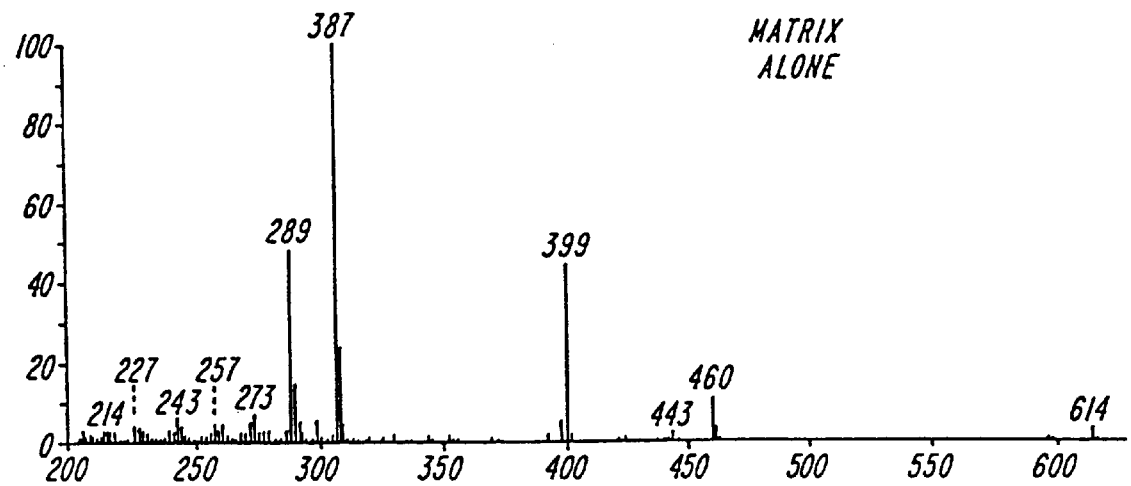

Another aspect of this invention concerns a "reverse-Sanger" type sequencing method using exonuclease digestion of nucleic acids to produce base-specific terminated ladders of nested digestion fragments which are detectable by mass spectrometry. For instance, as above, the target nucleic acid can be immobilized onto a solid support to provide unilateral degradation of the chain by exonuclease action; measuring the molecular weights of the fragments rather than nucleotides, reveals the sequence (FIG. 18). The nested exonuclease fragments are generated by incorporating into the target nucleic acid a limited number of mass-modified nucleotides which inhibit the exonuclease activity (i.e. protect an individual nucleic acid chain from further degradation). See Labeit et al. (1986) DNA 5:173; Eckstein et al. (1988) *Nucleic Acid Res*. 16:9947; and PCT Application No. GB86/00349. The nested exonuclease fragments can then be released from the solid support (i.e. via a cleavable linkage) and the molecular weight values for each species of the nested fragments determined by mass spectrometry, as described in U.S. Pat. No. 5,547,835 to Köster. FIG. 19 displays the spectrum of a mixture of 14 dT-terminated fragments. From the molecular weight values determined, the sequence of nucleic acid can be generated by superposition of the four sets of fragments. It is clear that many variations of this reaction are possible and that it is amenable to multiplexing. For example, the target nucleic acid need not be bound to a solid support, rather, any protecting group or the specificity of the enzyme can be used to ensure unilateral exonuclease degradation. Where mass-modified nucleotides are used which have large enough molecular weight differences to be differentiated by mass spectrometry (i.e. the termination of a chain with a particular mass-modified nucleotide is discernible from all other terminations), the exonuclease sequencing can be carried out by unilaterally sequencing more than one set of nested fragments. Alternatively, individual types of exonuclease-inhibiting nucleotides can be incorporated in separate reactions to create sets of nested fragments. For instance, four sets of nested fragments can be separately generated wherein one set terminates with mass-modified A's, one set terminates in mass-modified G's, etc. and the total sequence is determined by aligning the collection of nested exonuclease fragments.

Amenable mass spectrometric formats for use in the invention include the ionization (I) techniques such as matrix-assisted laser desorption (MALDI), continuous or pulsed electrospray (ESI) and related methods (e. g. Ionspray, Thermospray), or massive cluster impact (MCI); these ion sources can be matched with detection formats including linear or reflector time-of-flight (TOF), single or multiple quadrupole, single or multiple magnetic sector, Fourier transform ion cyclotron resonance (FTICR), ion trap, or combinations of these to give a hybrid detector (e. g. ion trap-time-of-flight). For ionization, numerous matrix/ wavelength combinations (MALDI) or solvent combinations (ESI) can be employed.

Figure 1:
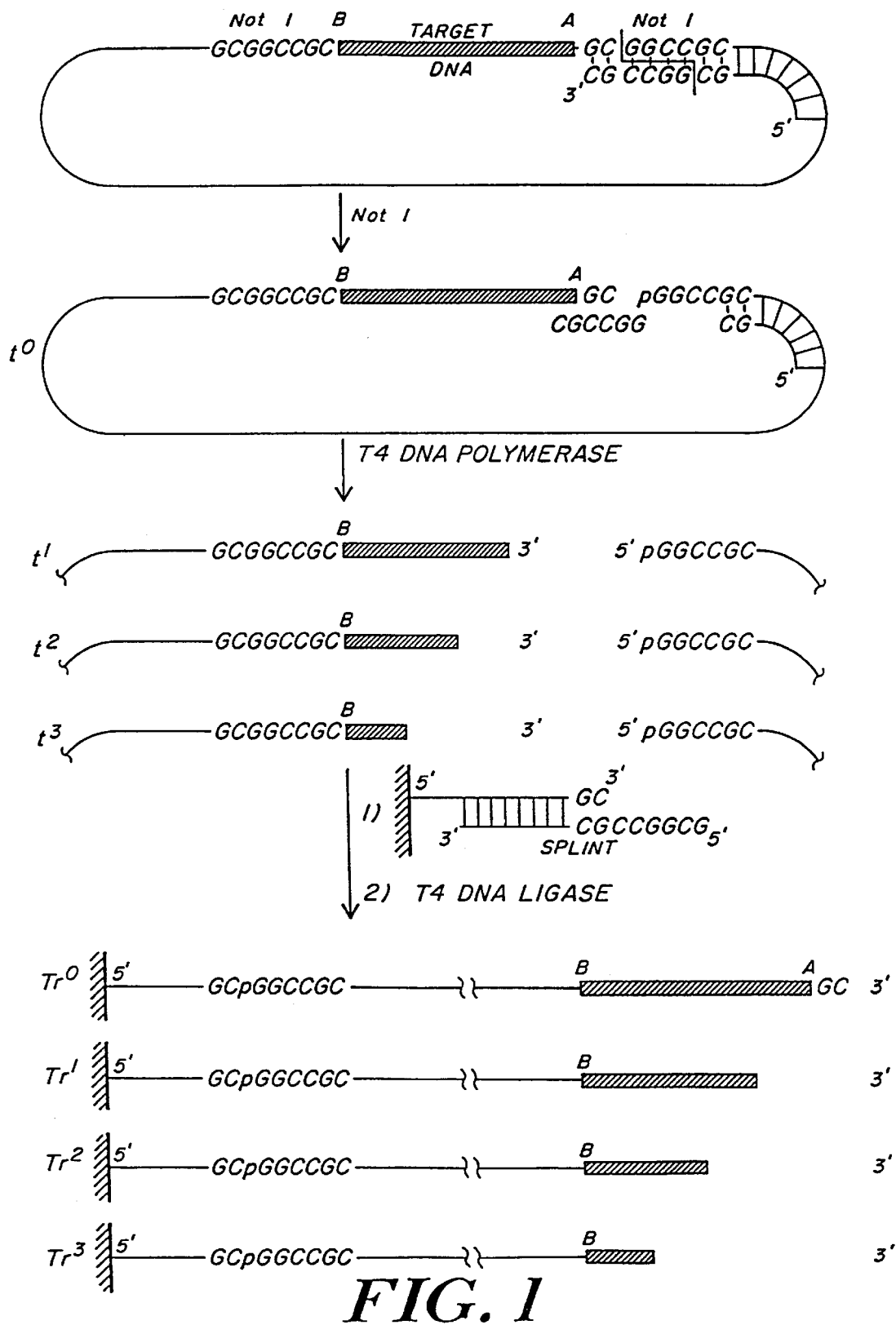
FIG. 1 illustrates a process of exonuclease sequencing beginning with a single-stranded nucleic acid.

(i) Preparation of Unknown Nucleic Acid Sequence for Exonuclease Sequencing:

FIG. 1 schematically depicts the instant claimed process for a single-stranded DNA insert ("Target DNA") of a single-stranded circular cloning vector. The boundaries of the target DNA are designated A and B. The target DNA, as illustrated in FIG. 1, has been cloned into the Not I site of a vector. A synthetic oligodeoxynucleotide [N. D. Sinha, J. Biernat, J. McManus and H. Köster, *Nucleic Acids Res.*, 12, 4539 (1984)] which will restore the Not I site to double-strandedness and which is complementary to the vector sequence flanking the A boundary of the insert DNA is hybridized to that site and cleaved by Not I restriction endonuclease. The two pieces of the synthetic oligodeoxynucleotide can then be removed by molecular sieving, membrane filtration, precipitation, or other standard procedures.

FIG. 1 also illustrates a set of ordered deletions ($t^0$, $t^1$, $t^2$, $t^3$) which can be obtained by the time-limited action of an exonuclease, e.g. T4 DNA polymerase, in the absence of dNTPs. The set of deletions can be immobilized on a solid support Tr ($Tr^0$, $Tr^1$, $Tr^2$, $Tr^3$), or alternatively, the set of ordered deletions can be obtained in a heterogeneous reaction by treating the solid support, $Tr^0$, containing the complete target DNA sequence, with an exonuclease in a time-limited manner. In the instance where the 3' termini of each time point are too heterogeneous (i.e. "fuzzy") to be analyzed directly by exonuclease-mediated mass spectrometric sequencing, circularization of the template and a cloning step can be performed prior to this sequencing process with single, transformed colonies selected.

Figure 9:
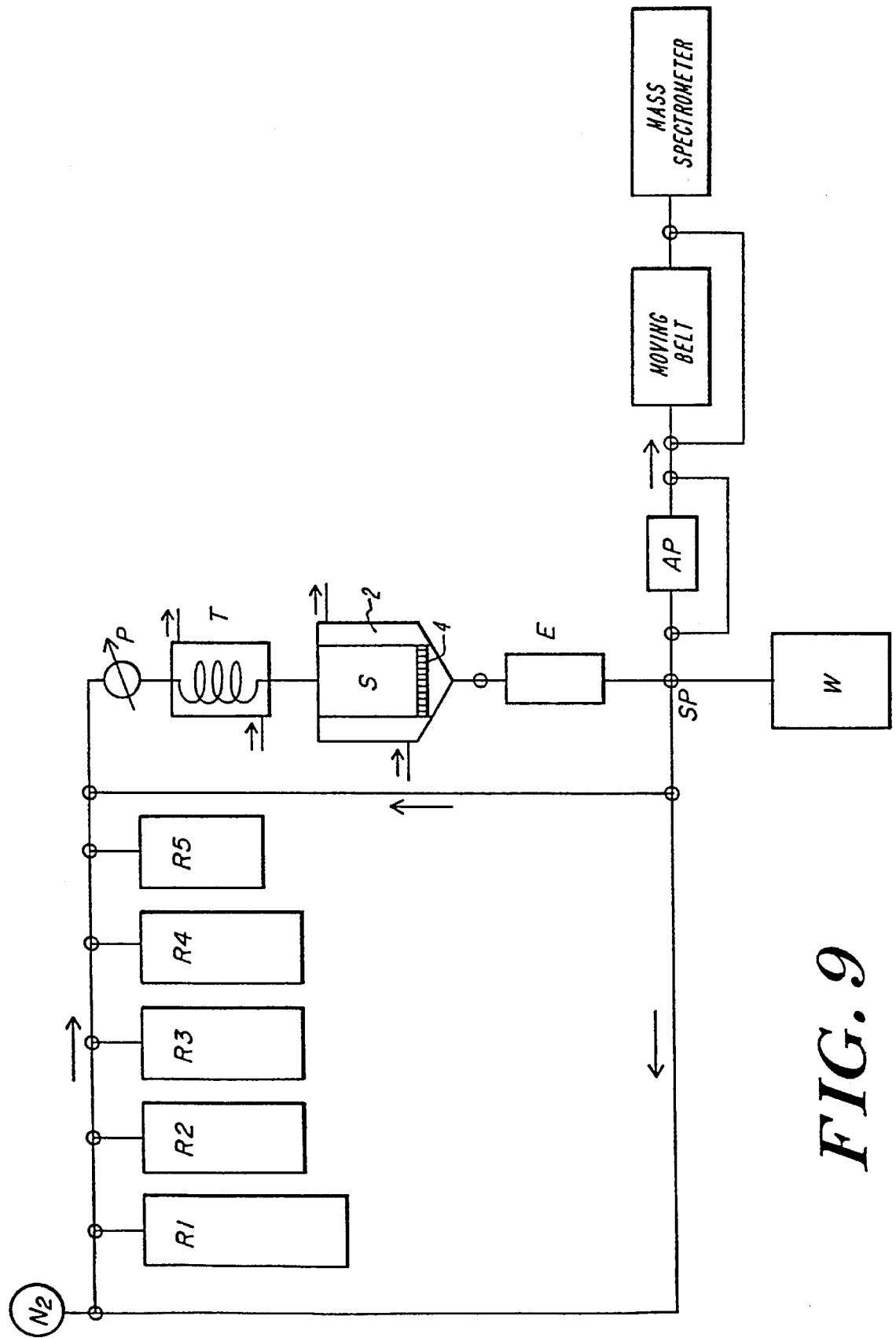
FIG. 9 is a schematic drawing of a sequencing reactor system.

A single-stranded linear DNA fragment carrying the unknown sequence with its A boundary at the 3' end can be directly sequenced by a 3' exonuclease in an apparatus described below and schematically depicted in FIG. 9, provided that the exonuclease is immobilized within the reactor, for example, on beads, on a frit, on a membrane located on top of the frit or on the glass walls of a capillary or entrapped in a gel matrix or simply by a semipermeable membrane which keeps the exonuclease in the reactor while the linear DNA fragment is circulating through a loop.

At time intervals, or alternatively as a continuous stream, the reaction mixture containing the buffer and the released nucleotides is fed to the mass spectrometer for mass determination and nucleotide identification. In another embodiment, the stream containing the nucleotides released by exonuclease action can be passed through a second reactor or series of reactors which cause the released nucleotide to be modified. For example, the second reactor can contain an immobilized alkaline phosphatase and the nucleotides passing therethrough are transformed to nucleosides prior to feeding into the mass spectrometer. Other mass-modifications are described below.

In general, when it is the released nucleotide (or ribonucleotide) which is mass-modified, the modification should take as few steps as possible and be relatively efficient. For example, reactions used in adding base protecting groups for oligonucleotide synthesis can also be used to modify the released nucleotide just prior to mass spectrometric analysis. For instance, the amino function of adenine, guanine or cytosine can be modified by acylation.

The amino acyl function can be, by way of illustration, an acetyl, benzoyl, isobutyryl or anisoyl group. Benzoylchloride, in the presence of pyridine, can acylate the adenine amino group, as well as the deoxyribose (or ribose) hydroxyl groups. As the glycosidic linkage is more susceptible to hydrolysis, the sugar moiety can be selectively deacylated if the acyl reaction was not efficient at those sites (i.e. heterogeneity in molecular weight arising from incomplete acylation of the sugar). The sugar moiety itself can be the target of the mass-modifying chemistry. For example, the sugar moieties can be acylated, tritylated, monomethoxytritylated, etc. Other chemistries for mass-modifying the released nucleotides (or ribonucleotides) will be apparent to those skilled in the art.

Figure 23:
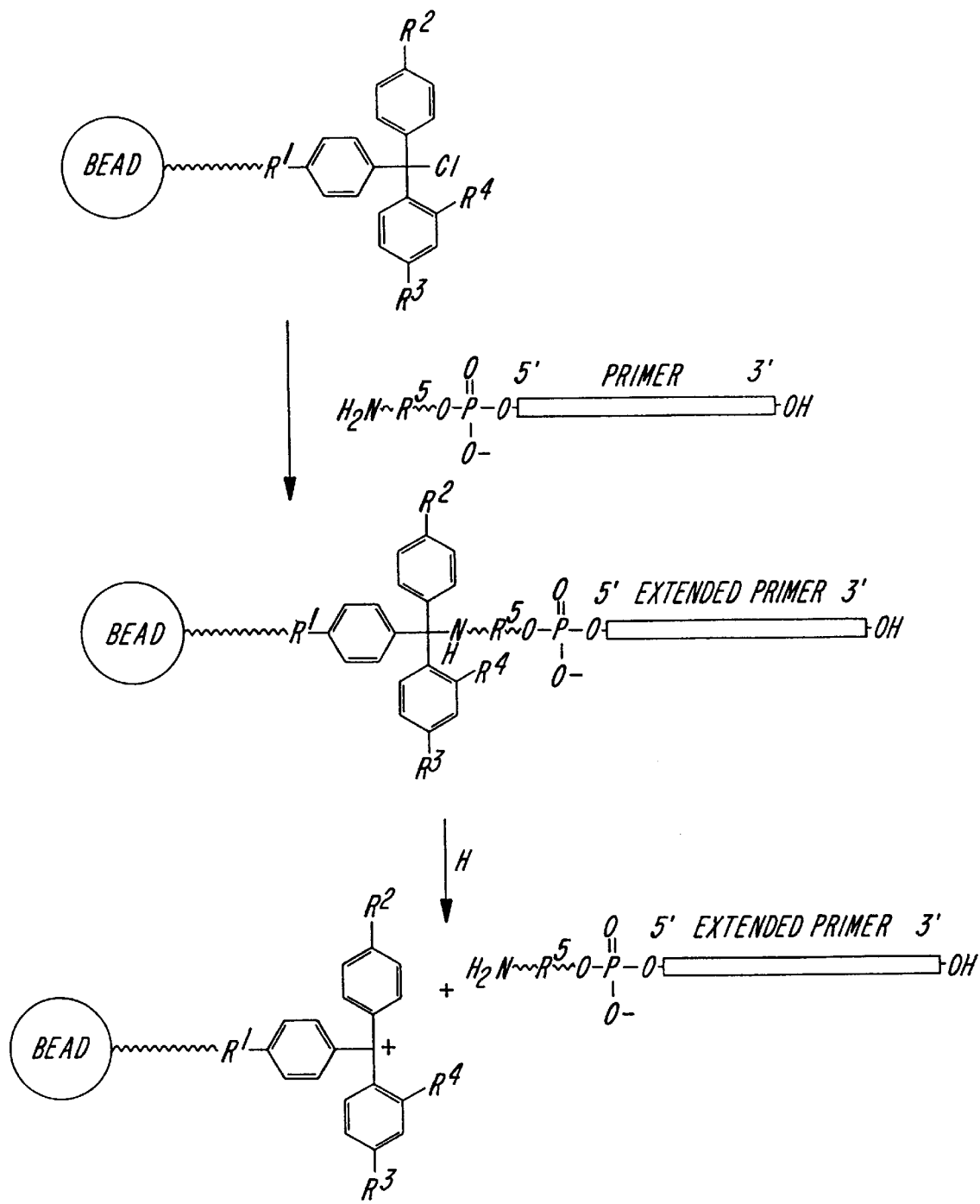
FIG. 23 is a schematic representation of nucleic acid immobilization via covalent bifunctional trityl linkers.
Figure 24:
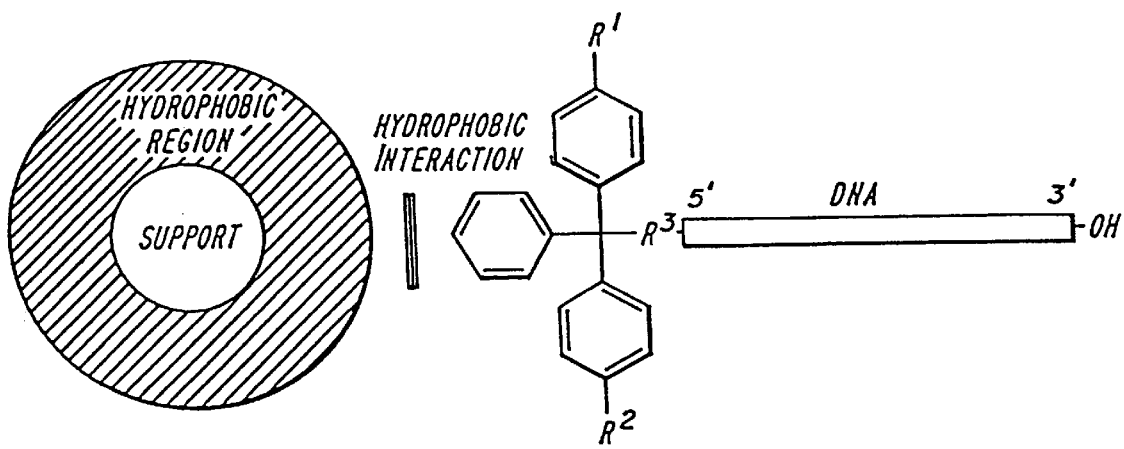
FIG. 24 is a schematic representation of nucleic acid immobilization via hydrophobic trityl linkers.

In another embodiment, the linear, single-stranded DNA fragment can be anchored to a solid support. This can be achieved, for example, by covalent attachment to a functional group on the solid support, such as through a specific oligonucleotide sequence which involves a spacer of sufficient length for the ligase to react and which is covalently attached via its 5' end to the support (FIG. 1). A splint oligonucleotide with a sequence complementary in part to the solid support-bound oligonucleotide and to the 5' end of the linearized single stranded vector DNA allows covalent attachment of the DNA to be sequenced to the solid support. After annealing, ligation (i.e. with T4 DNA ligase) covalently links the solid-support-bound oligonucleotide and the DNA to be sequenced. The splint oligonucleotide can be subsequently removed by a temperature jump and/or NaOH treatment, or washed off the support using other standard procedures. The solid support with the linear DNA is transferred to the reactor (FIG. 9) and contacted with an exonuclease in solution. As illustrated, where the 3' end of the unknown DNA fragment is exposed (i.e. unprotected), a 3' exonuclease is employed. The released nucleotides, or modified nucleotides, if intermediately contacted with a modifying agent such as alkaline phosphatase, are identified by mass spectrometry as described above. Other linking groups are described herein, and still others will be apparent to those skilled in the art based on the embodiments described herein. For example, the immobilization can occur through a covalent bond, such as a disulfide linkage, leuvolinyl linkage, a peptide/oligo peptide bond, a pyrophosphate, a tritylether or tritylamino linkage, which can be cleaved in accordance with standard procedures (see e.g. Example 14 and FIG. 23). Immobilization can also be obtained by non-covalent bonds such as between biotin and streptavidin or hydrophobic interactions (see e.g. Example 15 and FIG. 24).

A solid (i.e. insoluble) support as used herein refers to a support which is solid or can be separated from a reaction mixture by filtration, precipitation, magnetic separation, or the like. Exemplary solid supports include beads (such as agarose (e.g., SEPHAROSE$^R$), dextran cross-linked with epichlorohydrin (e.g., SEPHADEX$^R$),; polystyrene, polyacrylamide, cellulose, Teflon, glass, (including controlled pore glass), gold, or platinum); flat supports such as membranes (e.g., of cellulose, nitrocellulose, polystyrene, polyester, polycarbonate, polyamide, nylon, glass fiber, polydivinylidene difluoride, and Teflon); glass plates, metal plates (including gold, platinum, silver, copper, and stainless steel); silicon wafers, mictrotiter plates, and the like. Flat solid supports can be provided with pits, combs, pins, channels, filter bottoms, and the like, as is known in the art. The solid supports can also be capillaries, as well as frits from glass or polymers.

Various 3' and or 5' exonucleases can be used in the process of the invention, including: phosphodiesterase from snake venom, spleen phosphodiesterase, Exonuclease I or VII from *E. coli*, Bal 31 exonuclease, Mung Bean Nuclease, S1 Nuclease, *E. coli* DNA polymerase I, Klenow fragment of DNA polymerase I, T4 DNA polymerase, T7 DNA polymerase, Taq DNA polymerase, *Pyrococcus species* GB-D DNA polymerase, such as DEEP VENT$^R$ DNA Polymerase, *E. coli* exonuclease III, λ exonuclease and *Thermococcus litoralis* DNA polymerase, such as VENT$_R^R$ DNA Polymerase.

In another embodiment using a phagemid vector with an inverted f1 origin of replication, the B boundary is located at the 3' end of the immobilized linear single-stranded DNA and exposed to exonuclease sequencing using the same restriction endonuclease, hybridizing oligodeoxynucleotide and splint oligonucleotide. As another embodiment of this invention, the hybridizing oligonucleotide can also be designed to bind a promoter site upstream of the A boundary and by doing so restore the double-stranded promoter DNA. Directly, or with a short initiator oligonucleotide carrying an attachment functionality at the 5' end, transcription can be initiated with the appropriate specific DNA-dependent RNA polymerase [*Methods in Enzymology*, Vol. 185, Gene Expression Technology (1990); J. F. Milligan, D. R. Groebe, G. W. Witherell and O. C. Uhlenbeck, *Nucleic Acids Res.*, 15, 8783–98 (1987); C. Pitulle, R. G. Kleineidam, B. Sproat and G. Krupp, *Gene*, 112, 101–105 (1992) and H. Köster U.S. Pat. No. 5,547,835, supra]. The RNA transcript can be transferred to the reactor (FIG. 9) and contacted with an immobilized or otherwise contained exonuclease, or immobilized via the 5' functionality of the initiator oligonucleotide incorporated in the RNA transcript to a solid support and then contacted with an exonuclease in solution.

Depending on the length of the DNA insert (i.e. number of nucleotides between boundary A and B in FIG. 1) the mass spectrometric exonuclease sequencing process can allow the complete sequence from A to B to be determined in one run. Alternatively, prior to exonuclease sequencing, a set of ordered deletions can be prepared according to standard procedures [e.g. *Methods in Enzymology*, Vol. 101 (1983) and Vol. 152–155 (1987); R. M. K. Dale et al., *Plasmid*, 13, 31–40 (1985)], such that, in FIG. 1 the steps Tr$^0$ to Tr$^3$ can represent either different time values of the mass spectrometric exonuclease sequencing reaction from immobilized DNA fragments or different starting points for the exonuclease DNA/RNA mass spectrometric sequencing process. In either case, the principle of the invention described provides a process by which the total sequence of the insert can be determined.

Figure 2:
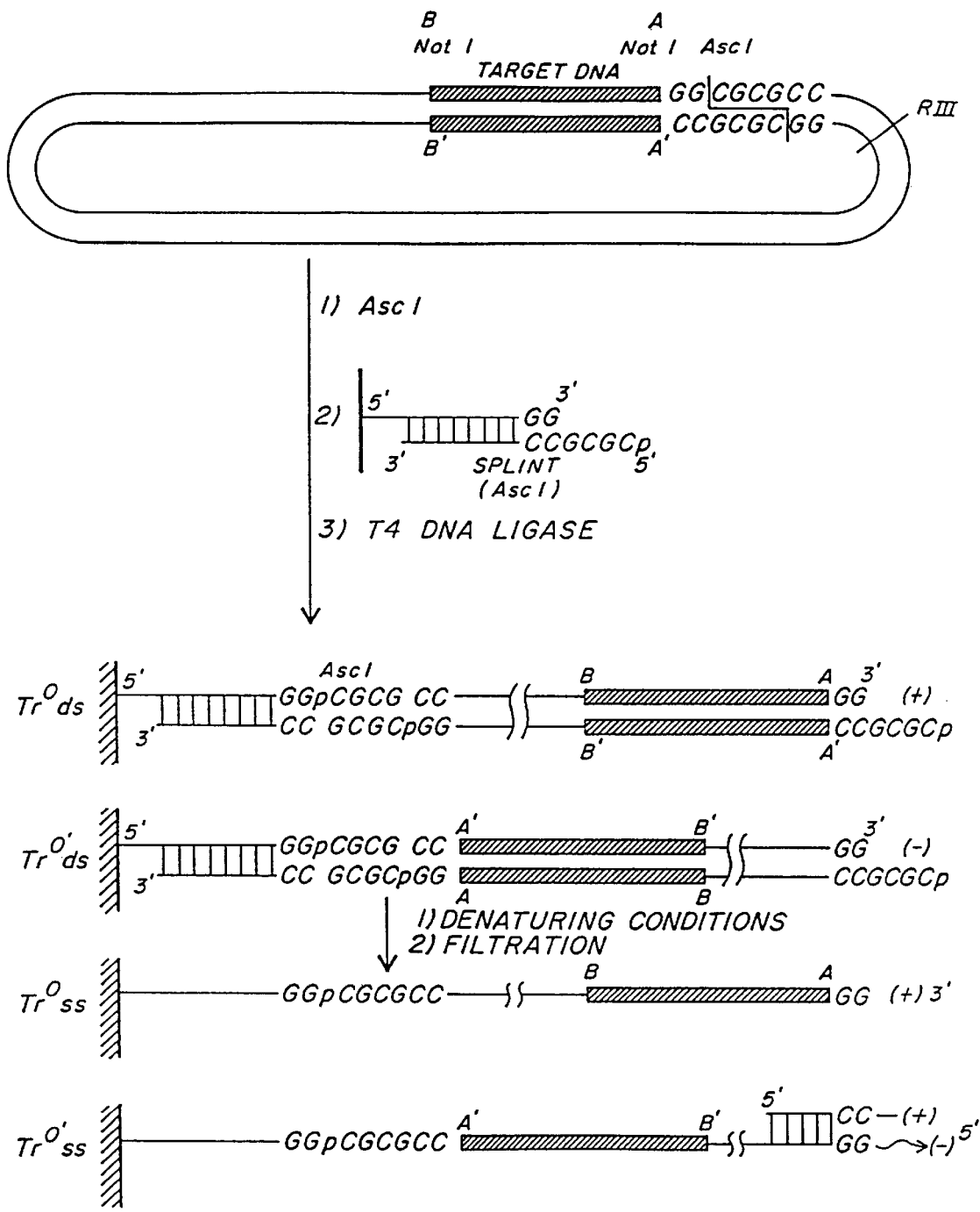
FIG. 2 illustrates a process similar to FIG. 1, however, starting with a target nucleic acid inserted into a double-stranded vector.

In another embodiment of the invention, the unknown DNA sequence (target DNA) is inserted into a double-stranded cloning vector (FIG. 2) or obtained in double-stranded form, as for example by a PCR (polymerase chain reaction) process [*PCR Technology*, (1989) supra]. The DNA to be sequenced is inserted into a cloning vector, such as ligated into the Not I site as illustrated in FIG. 2. Adjacent to the A boundary there can be located another cutting restriction endonuclease site, e.g. an Asc I endonuclease cleavage site. The double-stranded circular molecule can be linearized by treatment with Asc I endonuclease and ligated to a solid support using a splint oligodeoxynucleotide (and ligase) as described above, which restores the Asc I restriction site (Tr$^0$ds and Tr$^{0'}$ds). The strand which is not immobilized can be removed by subjecting the double-stranded DNA to standard denaturing conditions and washing, thereby generating single-stranded DNAs immobilized to the solid support (Tr$^0$ss and Tr$^{0'}$ss). Since the unknown double-stranded DNA sequence can be ligated in either orientation to the support, there can exist two non-identical 3' termini (+and − strand) immobilized, which can result in ambiguous sequencing data. The immobilized fragment which carries the vector DNA sequence at the 3' end (Tr$^{0'}$ss) can be protected from 3' exonuclease degradation during the sequencing process by, for example, annealing with an oligodeoxynucleotide complementary to the 3' end of the strand to be protected. As there can only be hybridization at one 3' terminus, i.e. to the wrong single-stranded DNA with (−) strand information (Tr$^{0'}$ss), some alpha-thio dNTP's can be incorporated into the immobilized (−) strand via treatment with a DNA polymerase to completely protect that strand from exonucleolytic degradation [P. M. J. Burgers and F. Eckstein, *Biochemistry*, 18, 592 (1979); S. Labeit, H. Lehrach and R. S. Goody, DNA, 5, 173 (1986); S. Labeit, H. Lehrach and R. S. Goody in *Methods in Enzymology*, Vol. 155, page 166 (1987), supra]. If desired, after incorporation of exonuclease-resistant nucleotides, the oligonucleotide primer may be removed by a washing step under standard denaturing conditions. The immobilized single-stranded DNAs are transferred to the sequencing reactor (FIG. 9) and the sample with the unknown sequence at the 3' end is degraded by an exonuclease in a stepwise manner. The liberated nucleotides, or optionally, modified nucleotides, are continuously fed into the mass spectrometer to elucidate the sequence.

As above, where the inserted DNA is too long for determining the complete sequence information between the boundaries A and B (FIG. 2) in one run of exonuclease mass spectrometric sequencing, a series of overlapping, ordered deletions can be constructed according to standard procedures, e.g. utilizing the restriction site RIII producing 3' sticky ends inert towards exonuclease III digestion [*Methods in Enzymology*, Vol 152–155 (1987) and S. Henikoff, *Gene*, (1984), supra]. When required, the deletion mutants can be recircularized and used to transform host cells following standard procedures. Single colonies of the transformed host cells are selected, further proliferated, and the deletion mutant isolated and immobilized as single-stranded DNAs, similar to the process described above and subsequently analyzed by exonuclease mass spectrometric sequencing. Alternatively, the immobilized, full length, single-stranded DNA (Tr$^0$ss) can be treated in time-limited reactions with an exonuclease such as T4 DNA polymerase in the absence of NTPs, to create a set of immobilized, ordered deletions for subsequent exonuclease mass spectrometric sequencing. However, in case the 3' termini are too heterogeneous for direct mass spectrometric exonuclease sequencing, an intermediate cloning step can be included. In yet another embodiment, the exonuclease mediated sequencing can be performed by providing the single-stranded (ss) nucleic acid fragment in solution. This can be achieved by treating the solid support, e.g. Tr$^0$ss, with an oligonucleotide complementary to the unique Asc I site. After hybridization this site is now double-stranded (ds) and susceptible to Asc I endonuclease cleavage and release of the single-stranded fragment.

If a cloning vector such as one of the pGEM family (Promega Corp.) is used, both strands of the double-stranded target DNA can be transcribed separately, depending upon which of the specific promoters flanking the insertion site is used (located next to the A or B boundary of the insert, FIG. 2) and the corresponding specific DNA-dependent RNA polymerase (i.e. SP6 or T7 RNA polymerase). These RNA transcripts can be directly transferred to the sequencing reactor (FIG. 9) for mass spectrometric exonuclease sequencing using an immobilized or entrapped exonuclease.

In an alternate embodiment, the transcription process is initiated via initiator oligonucleotides with a 5' functionality, allowing the subsequent immobilization of the RNA transcripts to a solid support [H. Köster, U.S. Pat. No. 5,547,835, supra], in this case the mass spectrometric sequencing can be performed within the sequencing reactor using an exonuclease in solution. The stepwise liberated ribonucleotides, or modified ribonucleotides (i.e. ribonucleosides generated by passing through a reactor containing immobilized alkaline phosphatase), are fed to the mass spectrometer for sequence determination.

(ii) Introduction of Mass-modified Nucleotides for Multiplex Exonuclease Sequencing:

Since standard mass spectrometry is a serial process, the throughput can be limited. However, in the present invention, the throughput can be considerably increased by the introduction of mass-modified nucleotides into the DNA or RNA to be sequenced, allowing for a parallel analysis of several nucleic acid sequences simultaneously by mass spectrometry. [See H. Köster, U.S. Pat. No. 5,547,835, supra] Low molecular weight nucleic acid components, such as unmodified or mass-modified nucleotides/nucleosides, can be analyzed simultaneously by multiplex mass spectrometry.

Figure 3:
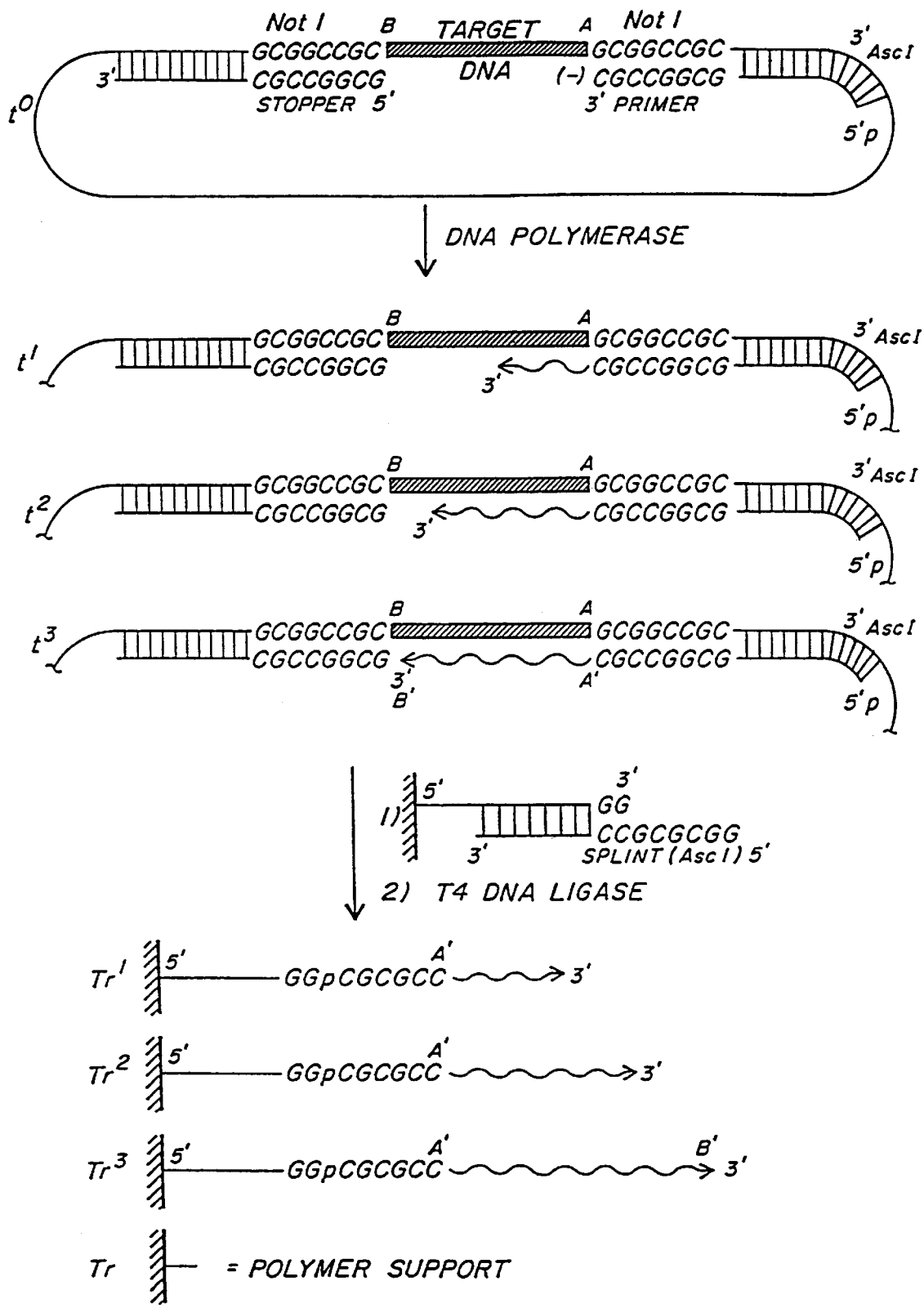
FIG. 3 illustrates a method for introducing mass-modified nucleotides into a target nucleic acid sequence (e.g. for multiplexing mass spectrometry).

Mass-modified nucleotides can be incorporated by way of mass-modified nucleoside triphosphate precursors using various methods. For example, one can begin with the insert of the target DNA sequence in a single-stranded cloning vector by having a "primer" and a "stopper" oligonucleotide bound to the complementary vector sequences located at the A and B boundary of the insert DNA respectively (FIG. 3) and a template-directed DNA polymerase, preferentially one lacking the 3'- 5' and 5'- 3' exonuclease activity, such as Sequenase, version 2.0 (U.S. Biochemicals, derived from T7 DNA polymerase), Taq DNA polymerase or AMV reverse transcriptase. In the illustrative embodiment, the unknown DNA sequence has been inserted in a restriction endonuclease site such as Not I. Adjacent to the A boundary, another restriction endonuclease site, such as the Asc I site, can be located within the primer binding site such that the partly double-stranded circular DNA can be cleaved at the unique Asc I site and the mass-modified (−) strand ($t^3$ in FIG. 3) isolated by standard procedures (i.e. membrane filtration, molecular sieving, PAGE or agarose gel electrophoresis) and, if desired, coupled to a solid support via a splint oligonucleotide restoring the Asc I site in double-stranded form for ligation by T4 DNA ligase (FIG. 3). After having removed the splint oligonucleotide, the immobilized, single-stranded DNA fragment with its B' boundary at the 3' end (i.e. $Tr^3$) is ready for exonuclease-mediated mass spectrometric sequencing. In another illustrative embodiment, the same primer can be used even when the vector has no complementary Asc1 site. Although the primer will not hybridize with its 5' terminal sequence to the vector as is shown in FIG. 3, it will nevertheless allow the covalent attachment of the single-stranded mass-modified DNA to the solid support using the same splint oligonucleotide as described above. In yet another embodiment, the primer can carry a non-restriction site sequence information at its 5' end, which may or may not be complementary to the opposite vector sequence, but is complementary to a specific splint oligodeoxynucleotide which allows the covalent attachment to the solid support. The latter two procedures do not require cleavage with a restriction endonuclease and separation of the strands.

The reaction mixture obtained after enzymatic synthesis of the mass-modified (−)strand can be directly joined to the solid support and the circular vector DNA, and the stopper oligonucleotide can be removed under denaturing conditions. In yet another embodiment, the generation of a set of ordered deletions of the target DNA sequence information and the incorporation of mass-modified nucleotides can be combined by terminating the DNA polymerase reaction at different time intervals (i.e. $t^0$, $t^1$, $t^2$, $t^3$, FIG. 3) to generate a ladder of mass-modified (−) strands. In case the 3' termini of each time point are too heterogeneous for mass spectrometric exonuclease sequencing, a circularization and cloning step as described above can be included.

Figure 14:
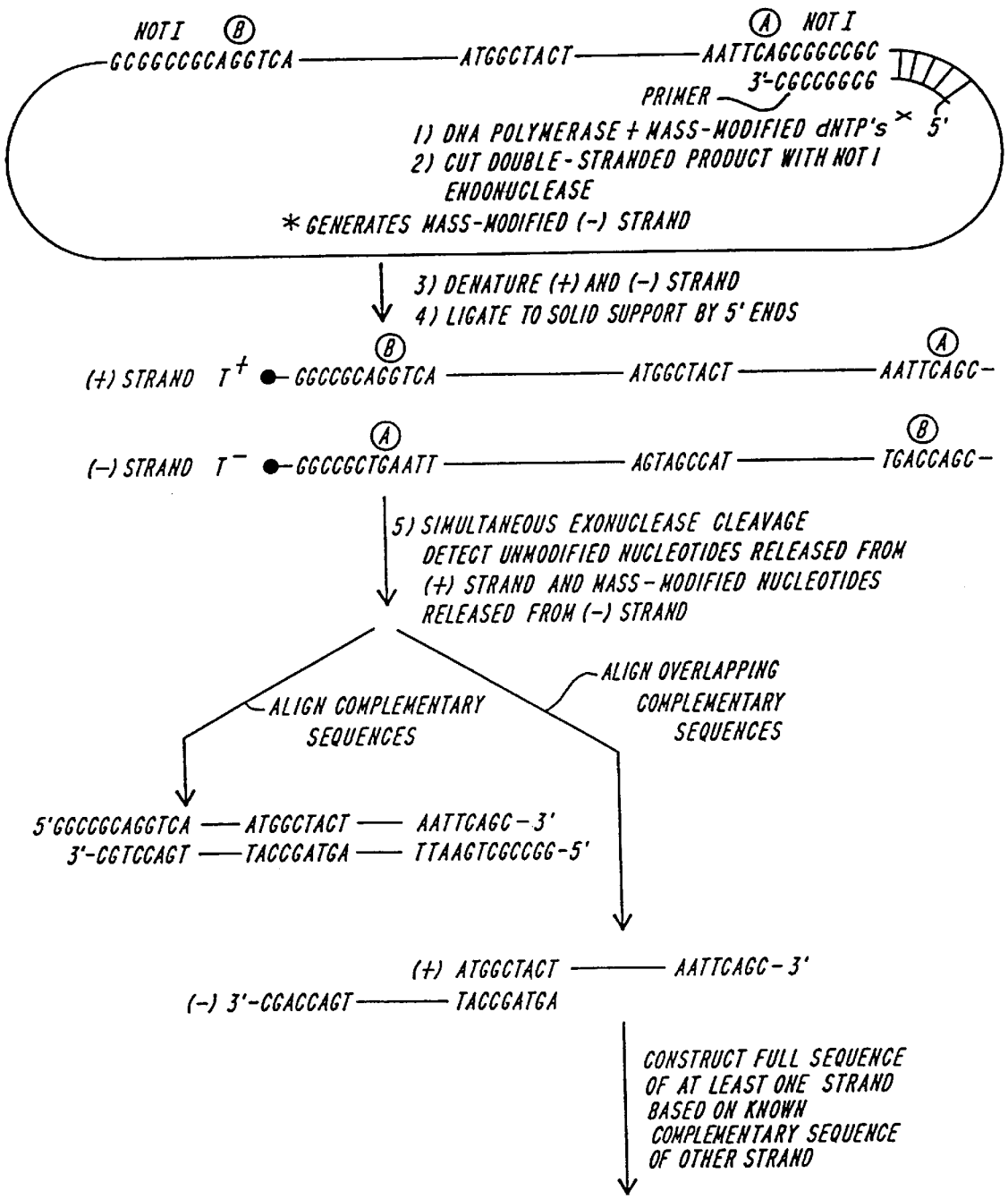
FIG. 14 illustrates a method for double-stranded exonuclease sequencing for mass spectrometric sequence determination.

As illustrated in FIG. 14, both the (+) and (−) strand can be exonuclease sequenced simultaneously. Incorporation of mass-modified nucleotides into one of the (+) or (−) strands can be carried out as described above. In the illustrative embodiment, both the (+) and (−) strands are ligated to solid supports and exonucleased simultaneously. The presence of the mass-modified nucleotides in the (−) strand can allow for differentiation of mass spectrometric signals arising from nucleotides released from both strands. Where exonuclease sequencing can proceed essentially between the A and B boundaries in one pass, the sequence of the (−) strand can be inverted and aligned with the complementary sequence. An advantage to this approach is the identification of ambiguous sequencing data (i.e. base pair mismatches arising from error of sequencing one of the strands). Alternatively, the full sequence can be obtained from partial exonuclease sequencing of both the (+) and (−) strands provided that sequencing proceeds to an overlapping point on each strand. By searching for the complementary overlapping region of each sequence fragment and aligning the two sequence fragments, the sequence of the remainder of one or both of the strands can be "reconstructed" based on the known sequence of the other. This latter example provides a means of sequencing in "one pass" a much larger DNA fragment than would be possible by exonuclease sequencing only one strand.

In using vectors of the phagemid type (e.g. pGEM family, Promega Corp.), both strands of the unknown DNA fragment can be mass-modified by using just the vector which carries the f1 origin of replication in the opposite direction as described in further embodiments of this invention and in analogy to the reactions described above; RNA transcripts of both strands can be obtained utilizing, for example, transcription promoter regions flanking the insertion site, restoring the double-stranded promoter site by complementary oligonucleotides [*Methods in Enzymology*, Vol. 185, (1990); Uhlenbeck et al., *Nucleic Acids Res.*, (1987), supra] and transcribing with appropriate RNA polymerases in the presence of mass-modified ribonucleoside triphosphates. As above, the mass-modified RNA can be directly transferred to the sequencing reactor for mass spectrometric sequencing using an immobilized or entrapped exonuclease. In another embodiment, the transcription can be initiated with initiator oligonucleotides [Krupp et al., *Gene*, (92), supra] carrying a 5' functionality for subsequent attachment of the mass-modified RNAs to a solid support. In the latter instance, the immobilized mass-modified RNAs can be contacted in the sequencing reactor (FIG. 9) with an exonuclease in solution for mass spectrometric sequencing.

Figure 4A:
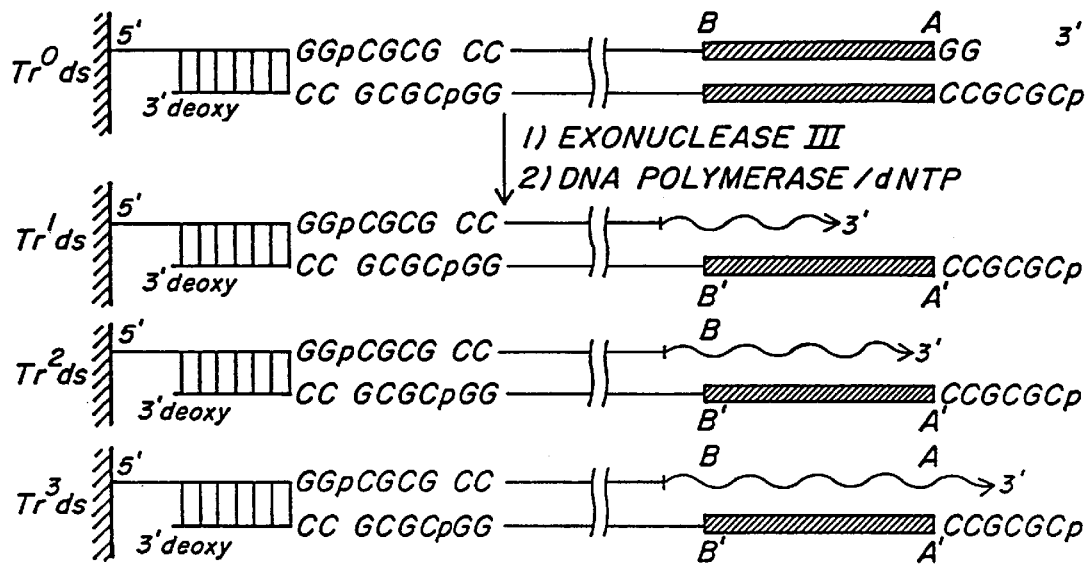
FIGS. 4A and 4B illustrate methods for introducing mass-modified nucleotides into a target nucleic acid sequence (e.g. for multiplexing mass spectrometry).
Figure 4B:
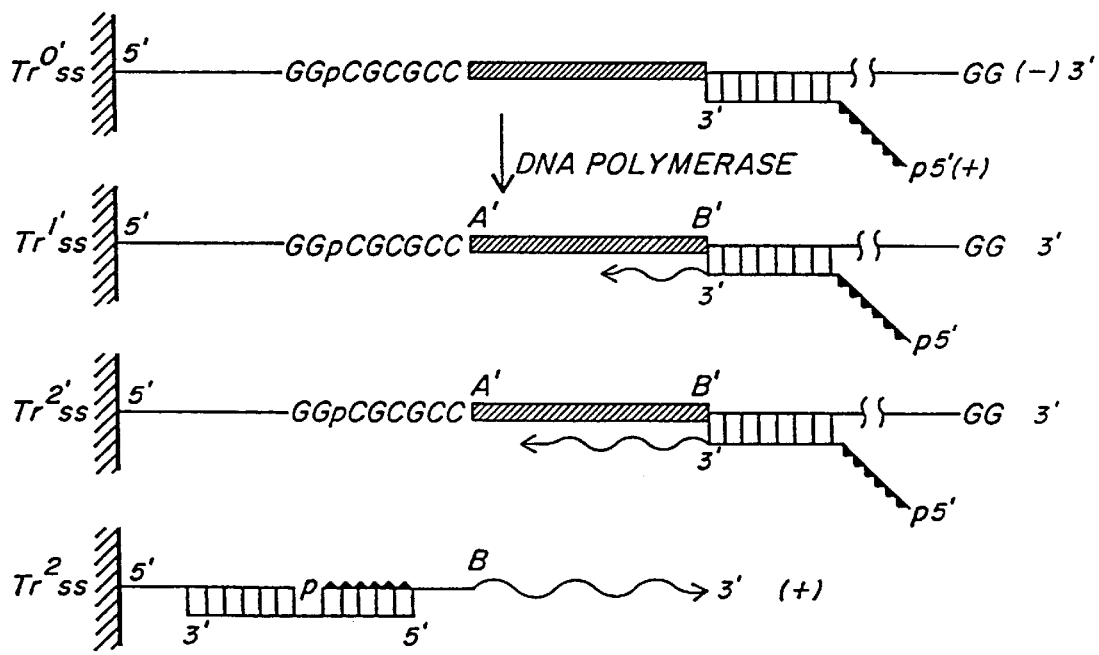

The mass-modification of the immobilized strand starting with the unknown DNA insert in a double-stranded vector (FIG. 4A) can be introduced starting with a situation similar to $Tr^0$ds in FIG. 2. However, a 5'-phosphorylated exonuclease III-resistant splint oligonucleotide (i.e. 2',3' dideoxy) is ligated to the (−) strand, allowing a unilateral digestion of the (+) strand with exonuclease III (FIG. 4A). The mass-modifications are then introduced by a filling-in reaction using template-dependent DNA polymerases such as Sequenase, version 2.0 (U.S. Biochemicals), Taq DNA polymerase or AMV reverse transcriptase and appropriate mass-modified dNTPs. In another embodiment, one can start with a situation similar to Tr⁰ss in FIG. 2 and, by using a (−) primer designed to bind outside the A boundary at the 3' end of the (+) strand, synthesize a mass-modified (−) strand employing mass-modified dNTPs and a DNA-dependent DNA polymerase as described above. In one embodiment, there can be a short stretch of sequence between the Not I and the Asc I site to allow this primer to hybridize effectively. This approach can also be carried out by generating a mass modified (+) strand starting with Tr⁰ss (FIG. 4B). The newly synthesized (+) strand can be isolated from the (−) strand solid support, such as by denaturation, and immobilized via the 5' sequence information of the primer and a splint oligonucleotide which is in part complementary to this and to an oligonucleotide sequence already attached to another solid support (FIG. 4B). After ligation (i.e. with T4 ligase) the splint oligonucleotide is removed and the immobilized mass-modified single-stranded (+) DNA is transferred to the sequencing reactor (FIG. 9) and contacted with an exonuclease, such as T4 DNA polymerase in solution, for mass spectrometric sequence determination via the released mass-modified nucleotides.

Figure 5:
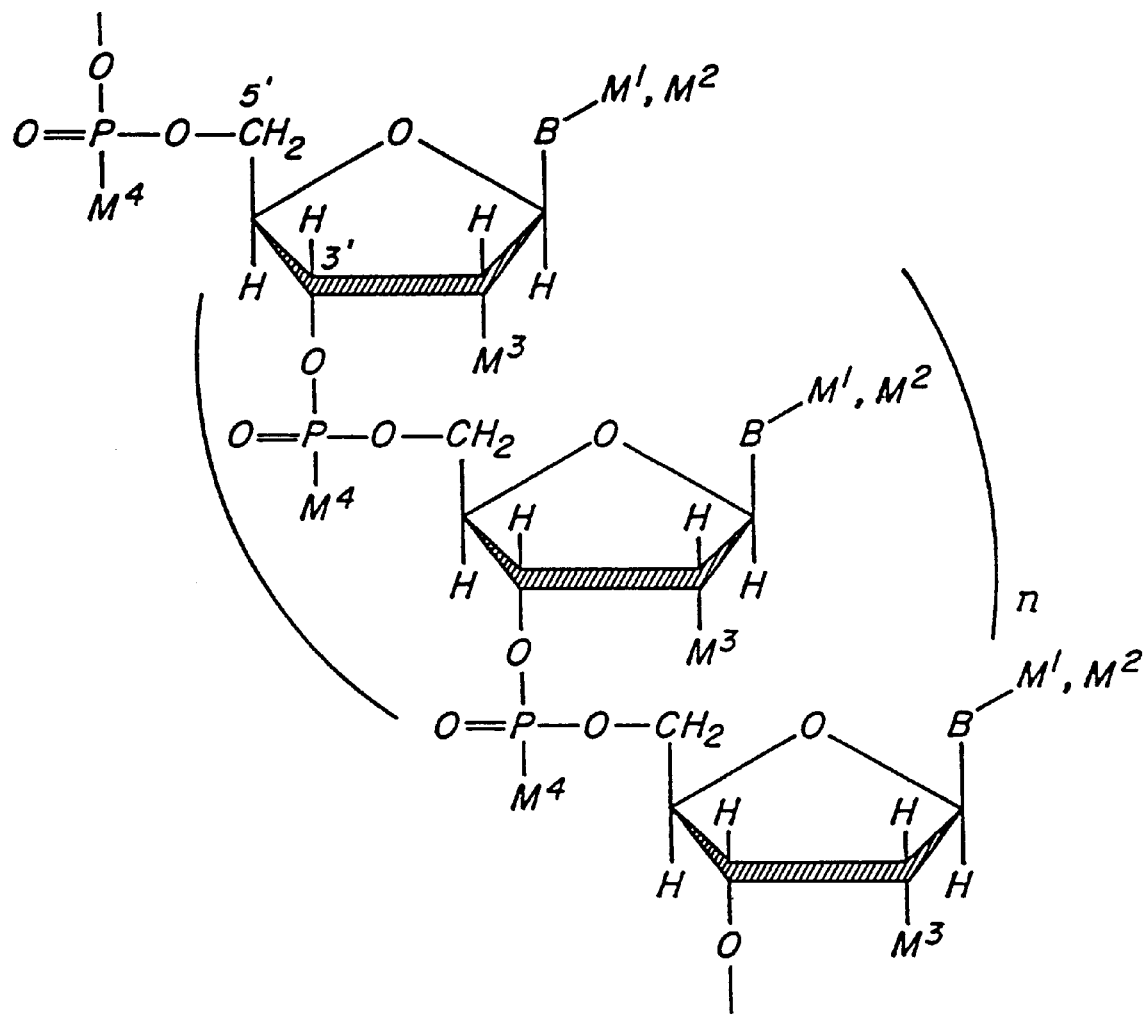
FIG. 5 shows positions within a nucleic acid molecule which can be modified for the introduction of discriminating mass increments or modulation of exonuclease activity.
Figure 6:
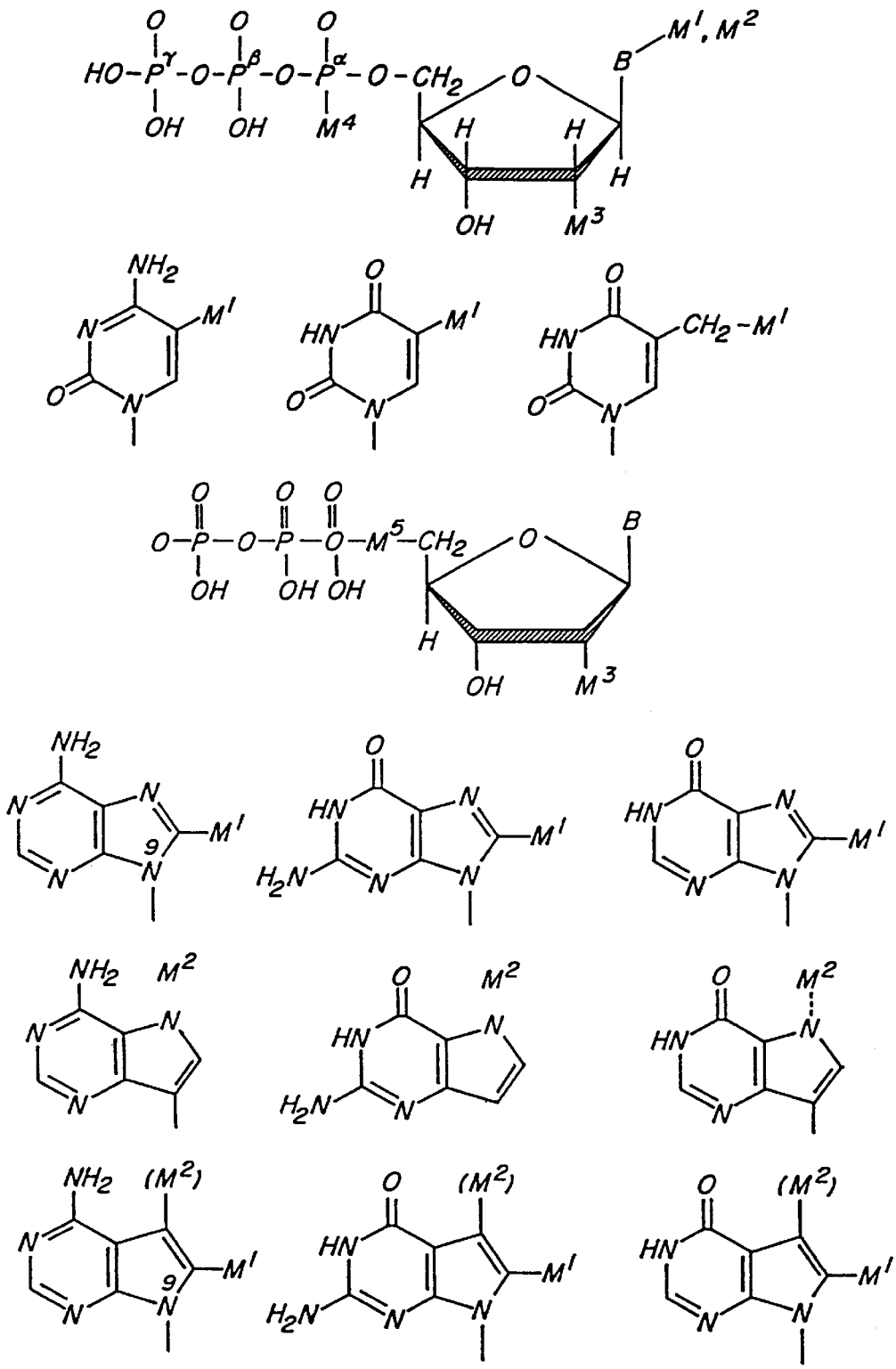
FIG. 6 illustrates various structures of modified nucleoside triphosphates useful for the enzymatic incorporation of mass-modified nucleotides into the DNA or RNA to be sequenced.

In accordance with this invention, the mass-modifying functionality can be located at different positions within the nucleotide moiety (FIGS. 5 and 6). See also H. Köster, U.S. Pat. No. 5,547,835, for further examples and synthesis chemistries. For instance, the mass-modifying functionality can be located at the heterocyclic base at position C-8 in purine nucleotides (M1) or C-8 and/or C7 (M2) in c7-deazapurine nucleotides and at C-5 in uracil and cytosine and at the C-5 methyl group at thymine residues (M1). Modifications in these positions do not interfere with Watson-Crick-specific base-pairing necessary for the enzymatic incorporation into the mass-modified nucleic acids (DNA/RNA) with high accuracy.

Modifications introduced at the phosphodiester bond (M4), such as with alpha-thio nucleoside triphosphates, have the advantage that these modification, do not interfere with accurate Watson-Crick base-pairing and, additionally allow for the one-step post-synthetic site-specific modification of the complete nucleic acid molecule e.g. via alkylation reactions [K. L. Nakarnaye, G. Gish, F. Eckstein and H.-P. Vossberg, *Nucleic Acids Res.*, 16, 9947–59 (1988)]. However, this modification is not applicable where the exonucleolytically released nucleotides are to be treated with immobilized alkaline phosphatase to intermediate release and mass spectrometric detection. Particularly preferred mass-modifying functionalities are boron-modified nucleic acids since they are better incorporated into nucleic acids by polymerases. (Porter, K. W. et al. (1995) Biochemistry 34: 11963–11969; Hasan, A. et al., (1996) *Nucleic Acids* Research 24: 2150–2157; Li, H. et al. (1995) *Nucleic Acids* Research 23: 4495–4501.

Mass modification can also occur at the sugar moiety, such as at the position C-2' (M3). Modifications at this position can be introduced with the purpose of modulating the rate of exonuclease activity in order to synchronize the degradation process from time to time. The modification (M4) can also serve this purpose. For example, it is known [Burgers and Eckstein, (1979), supra] that a phosphodiester bond carrying a monothio function is approximately 100 times less sensitive towards exonucleolytic degradation by exonuclease III.

Figure 8:
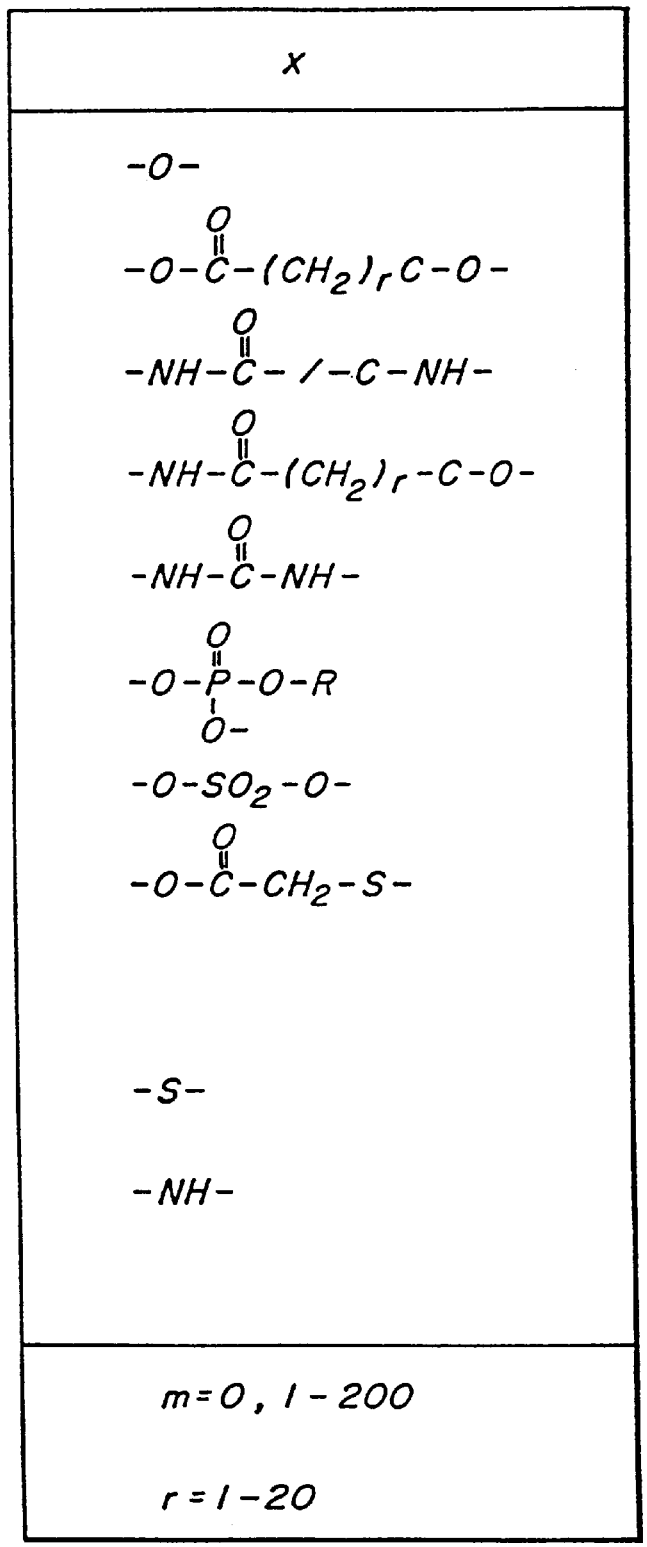
FIG. 8 illustrates some linking groups (X) for the attachment of the mass-modifying functionality (R) to nucleosides.

The tables in FIGS. 7 and 8 depict some examples of mass-modifying functionalites for nucleotides. This list is, however, not meant to be limiting, since numerous other combinations of mass-modifying functions and positions within the nucleotide molecule are possible and are deemed part of the invention. The mass-modifying functionality can be, for example, a halogen, an azido, or of the type XR, wherein X is a linking group and R is a mass-modifying functionality. The mass-modifying functionality can thus be used to introduce defined mass increments into the nucleotide molecule.

Without limiting the scope of the invention, the mass modification, M, can be introduced for X in XR as well as using oligo/polyethylene glycol derivatives for R. The mass-modifying increment in this case is 44, i.e. five different mass-modified species could be generated by just changing m from 0 to 4, thus adding mass units of 45 (m=0), 89 (m=1), 133 (m=2), 177 (m=3) and 221 (m=4). The oligo/polyethylene glycols can also be monoalkylated by a lower alkyl such as methyl, ethyl, propyl, isopropyl, t-butyl and the like. A selection of linking functionalities (X) are also illustrated in FIG. 8. Other chemistries can be used in the mass-modified compounds, as, for example, those described recently in Oligonucleotides and Analogues, A Practical Approach, F. Eckstein, editor, IRL Press, Oxford, 1991.

In yet another embodiment, various mass-modifying functionalities, R, other than oligo/polyethylene glycols, can be selected and attached via appropriate linking chemistries, X. A simple mass modification can be achieved by substituting H for halogens like F, Cl, Br and/or I; or pseudohalogens such as NCN, SCN or NCS; or by using different alkyl, aryl or aralkyl moieties such as methyl, ethyl, propyl, isopropyl, t-butyl, hexyl, phenyl, substituted phenyl, benzyl; or functional groups such as $CH_2F$, $CHF_2$, $CF_3$, $Si(CH_3)_3$, $Si(CH_3)_2(C_2H_5)$, $Si(CH_3)(C_2H_5)_2$, $Si(C_2H_5)_3$. Yet another can be obtained by attaching homo- or heteropeptides through X to the nucleotide. One example useful in generating mass-modified species with a mass increment of 57 is the attachment of oligoglycines, e.g. mass modifications of 74 (r=1, m=O), 131 (r=1, m=2), 188 (r=1, m=3), 245 (r=1, m=4) are achieved. Simple oligoamides also could be used, e.g. mass modifications of 74 (r=1, m=0), 88 (r=2, m=0), 102 (r=3, m=0), 116 (r=4, m=0) etc. are obtainable. For those skilled in the art it will be obvious that there are numerous possibilities, for introducing, in a predetermined manner, many different mass-modifying functionalities to the nucleotide.

In yet another embodiment of this invention, the mass-modifying functionality can be introduced by a two or multiple step process. In this case, the nucleotide is, in a first step, modified by a precursor functionality such as azido, $—N_3$, or modified with a functional group in which the R in XR is H, thus providing temporary functions e.g. but not limited to —OH, —NH2, —NHR, —SH, —NCS, —OCO $(CH_2)_r$COOH (r=1–20), —NHCO $(CH_2)_r$COOH (r=1–20), $—OSO_2OH$, $—OCO(CH_2)_r$I (r=1–20), —OP(O-Alkyl)N (Alkyl)$_2$. These less bulky functionalities result in better substrate properties for enzymatic DNA or RNA synthesis reactions. The appropriate mass-modifying functionality can then be introduced after the generation of the target nucleic acid prior to mass spectrometry and either prior to exonuclease degradation or after release by exonuclease action.

(iii) The Exonuclease Sequencer:

A schematic outlay of an exonuclease sequencer is shown in FIG. 9. The central part is the reactor S which has a cooling/heating mantle (2) and a frit or semipermeable membrane (4). Several flasks (R1–R5) can be dedicated to supplying reagents such as buffer solutions, enzymes, etc. through a cooling/heating coil, T. Beneath the reactor (S) there is a capillary tube (E) in which either the exonuclease or the nucleic acids can be immobilized. It is within the scope of this invention that there are at least two different modes by which the system can be operated. In one mode, the nucleic acids are immobilized on beads or flat membrane disks placed in the reactor (S), or alternatively, immobilized on the inner surface of the walls within the capillary (E). Exonuclease is added to the reactor in a controlled manner and the reaction mixture circulated through a loop maintained at a carefully controlled temperature. In a second mode, the exonuclease can be immobilized in, e.g. a capillary (E) beneath the reactor (S) or could be immobilized on beads or on a membrane or entrapped in a gel or kept in the reactor (S) by way of a semipermeable membrane. By varying the length and diameter of the capillary and the flow rate through a pumping device (P), the contact time of the nucleic acids with the exonuclease can be varied.

In both process modes, aliquots can be fed either continuously or in pulses to the mass spectrometer either directly or through a reactor (AP) which contains, for instance, immobilized alkaline phosphatase or other mass-modifying reagents. In case the liquid volume which is transferred to the mass spectrometer is too large, only a portion can be supplied while the remainder is separated from the flow stream by using a flow-splitting device (SP). Unused or excess solutions can be disposed of by the waste container, W. In case the reaction mixture of the exonuclease digestion is processed via a moving belt, the liquid flow can be directed through this module prior to entering the mass spectrometer.

(iv) The Exonuclease Sequencing Process:

Various 3' and/or 5' exonucleases can be used in the process of the invention, including: phosphodiesterase from snake venom, spleen phosphodiesterase, Exonuclease I or VII from E. coli, Bal 31 exonuclease, Mung Bean Nuclease, S1 Nuclease, E. coli DNA polymerase I, Klenow fragment of DNA polymerase I, T4 DNA polymerase, T7 DNA polymerase, Taq DNA polymerase, *Pyrococcus species* GB-D DNA polymerase, such as DEEP VENT$^R$ DNA Polymerase, *E. coli* exonuclease III, λ exonuclease and *Thermococcus litoralis* DNA polymerase, such as VENT$_R^R$ DNA Polymerase. The activity of these exonucleases can be modulated, for instance, by shifting off the optimal pH and/or temperature range or by adding poisoning agents to the reaction mixture. The exonuclease activity can also be modulated by way of functional groups, such as at the C-2' position of the sugar moiety of the nucleotide building block or at the phosphodiester bond (i.e. M3/M4 in FIGS. 5 and 6).

Figure 10:
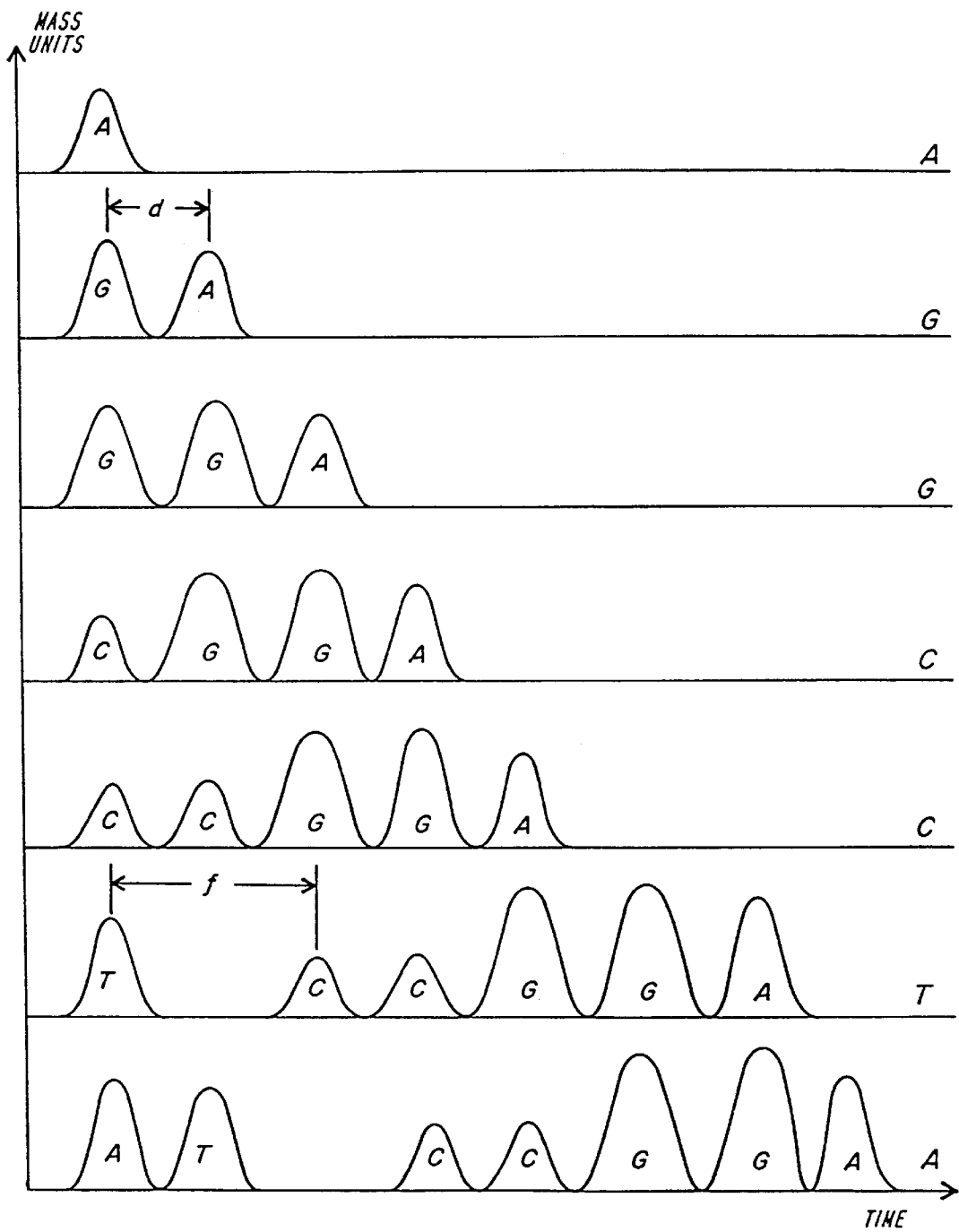
FIG. 10 is a graphical representation of idealized output signals following the time-course of the stepwise mass spectrometric detection of the exonucleolytically released nucleotides.

In the instance that unmodified nucleotides are detected, the masses for the phosphate dianion are 329.209 for pdG, 313.210 for pdA, 304.196 for pdT and 289.185 for pdC. In an ideal system, the enzymatic digestion would be initiated at all nucleic acid chains at the same time, and the nucleotides would be released in identical time intervals (d) and detected by their individual molecular weights, one after the other, by the mass spectrometer. FIG. 10 illustrates the signals versus time for the sequence 5' . . . A-T*-C-C-G-G-A 3'.

The influence of an activity-modulating functionality (M3/M4) on appropriately modified thymidine, T*, is also depicted. Due to the drastically reduced cleavage rate of the phosphodiester bond between dC and dT*, the molecular mass representing the T* signal appears after a longer time interval, f. The significant retardation of the cleavage rate of one type of nucleotide results in better overall synchronization of the enzymatic process. This retardative effect can be varied to a large extent by the bulkiness of the modifying functional group as well as by a possible interaction with the active site of the exonuclease. Additionally, partial overlap of signals can be resolved by computational methods.

Figure 11:
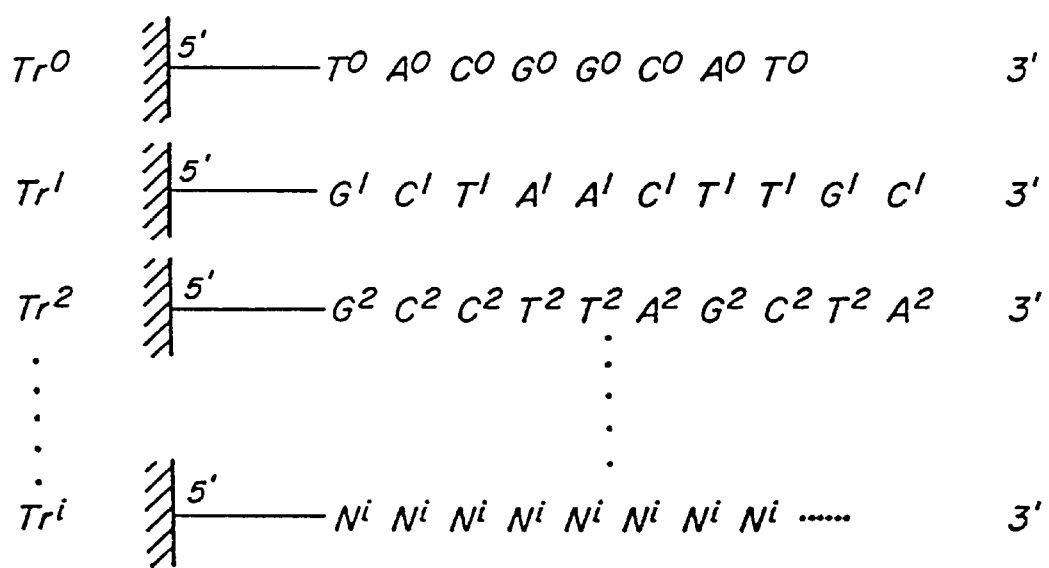
FIG. 11 illustrates specific labels introduced by mass modification to facilitate multiplex exonuclease mass spectrometric sequencing.

(v) Multiplex Exonuclease Sequencing:

A significant increase in throughput can be further obtained by employing the principle of multiplex exonuclease sequencing. The principle of this concept is illustrated in FIG. 11. For multiplex mass spectrometric exonuclease DNA sequencing, the DNA fragments to be processed in parallel can be identified by fragment-specific labels introduced by the mass-modifying functionality M. The target nucleic acid sequences can be mass-modified by using, for example, unmodified dNTP$^0$s or NTP$^0$s (Tr$^0$), nucleoside triphosphates mass-modified with the same functional group, such as an additional methyl group at the heterocyclic base, using either dNTP$^1$ or NTP$^1$ (Tr$^0$), with mass difference large enough to be discriminated from the nucleotides of Tr$^0$ or Tr$^1$, such as e.g. an ethyl group at the heterocyclic base, by employing either dNTP$^2$ or NTP$^2$ etc. Thus, i-modified DNA fragments can be simultaneously exonuclease sequenced. For example, the i different DNA fragments can be immobilized on different membranes and a stack of such membranes placed into the reactor, S (FIG. 9) for simultaneous exonuclease mass spectrometric sequencing. Since the individual molecular weights of the various mass-modified four nucleotides are known in advance, the mass spectrometrically detected nucleotide masses can be easily assigned to the parent nucleic acid fragments and thus several sequences can be detected simultaneously by the mass spectrometer. Even in the worst case when the same nucleotide, e.g. dT, is at the same position in all sequences, processed in parallel, the signal can be decoded due to the difference in mass between dT$^0$, dT$^1$, dT$^2$, dT$^3$, . . . , dT$^i$.

The synchronization of exonuclease action can be improved by incorporating modified nucleotides (modified at C-2' or at the phosphodiester bond) into the otherwise unmodified or mass-modified nucleic acid fragments as set out above. In particular, such a mass-modified nucleotide can also be introduced at the 3' end of the single-stranded nucleic acid fragment (i.e. C-2' or phosphodiester bond modifications) to achieve a more uniform initiation of the exonuclease reaction.

Figure 12:
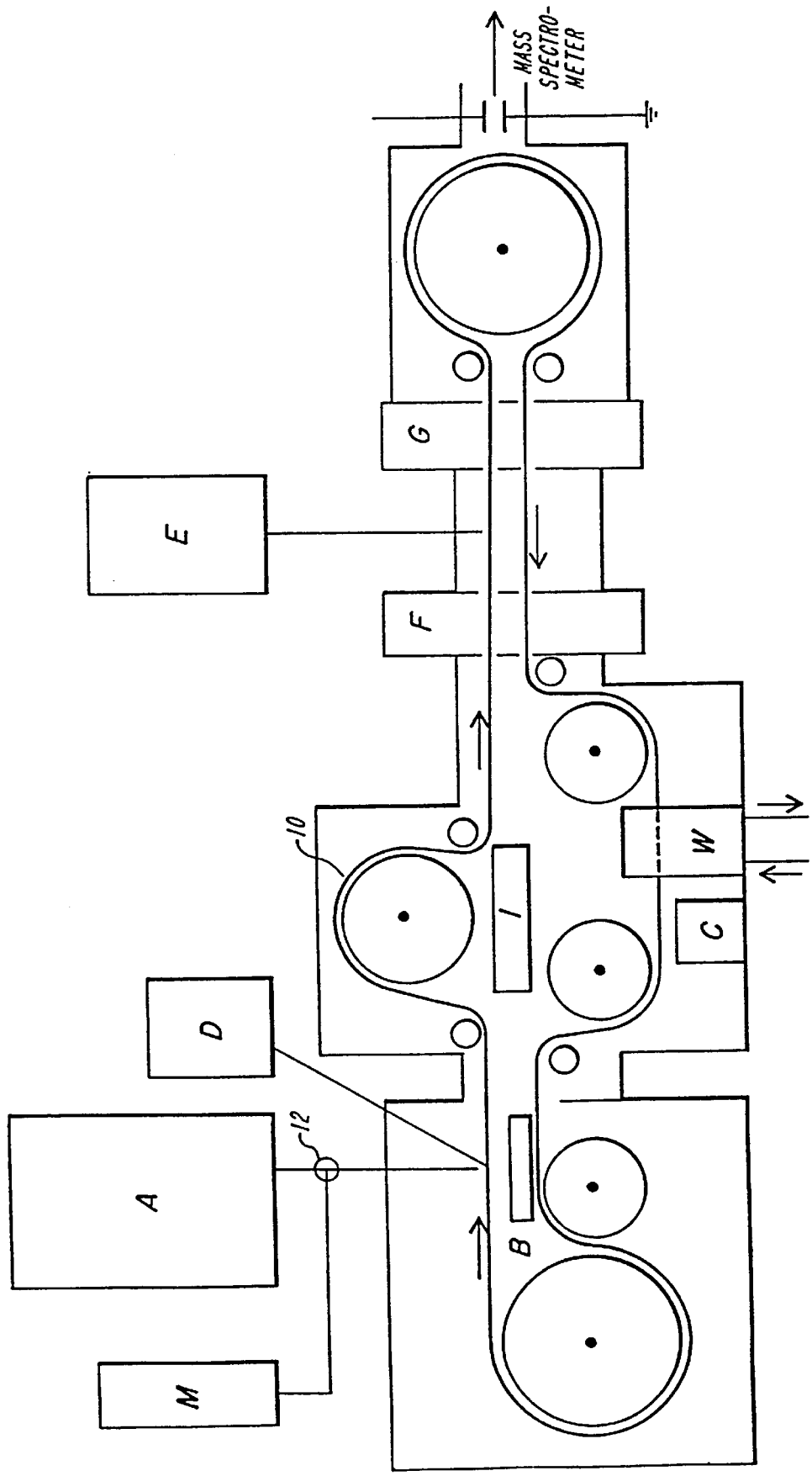
FIG. 12 is a schematic drawing of a moving belt apparatus for delivering single or multiple tracks of exonuclease samples for laser-induced mass spectrometric sequence determination in conjunction with the sequencing reactor of FIG. 9.
Figure 13:
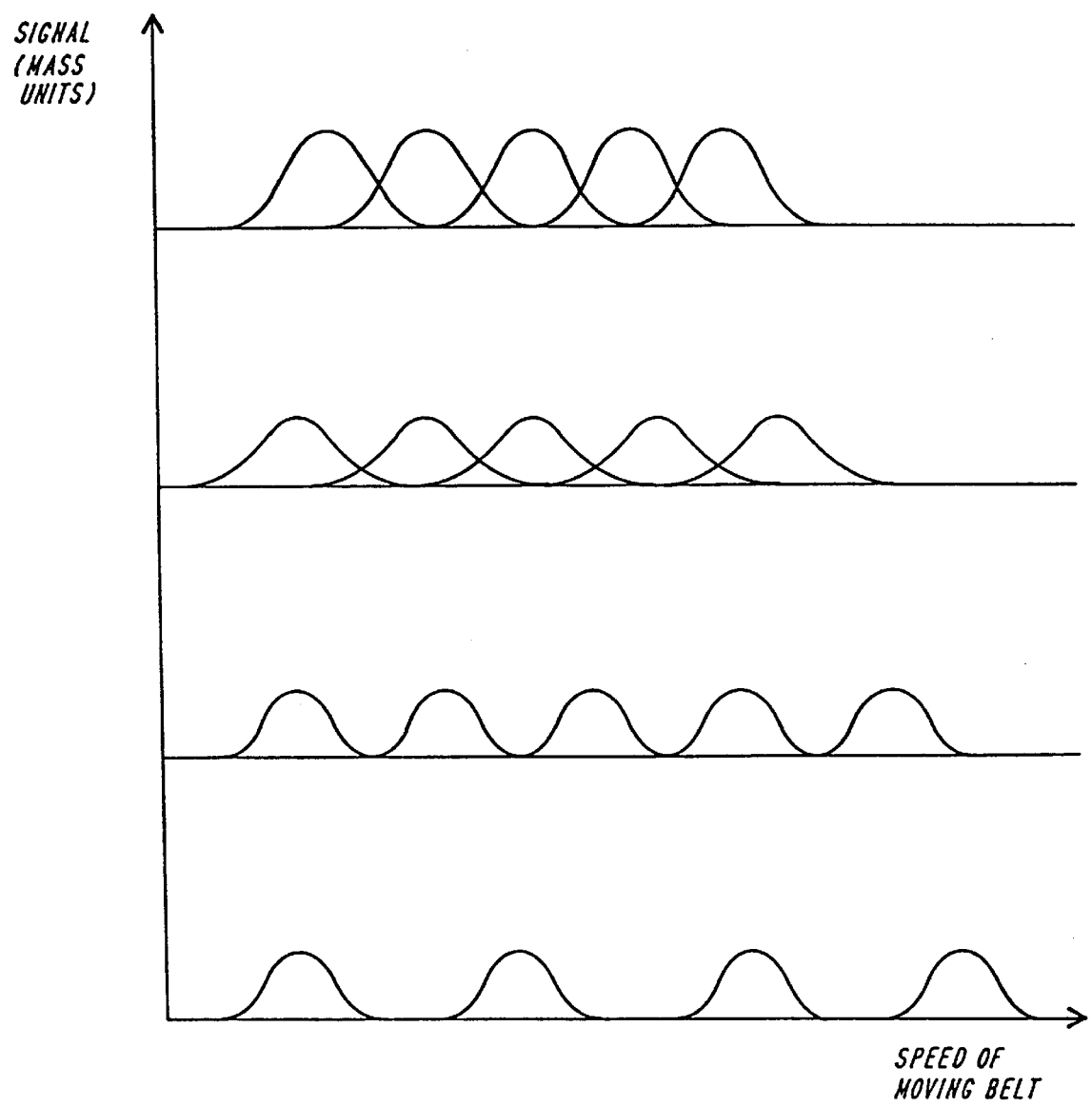
FIG. 13 is a schematic representation of individually labeled signal racks employed in multiplex exonuclease-mediated mass spectrometric sequencing.

In yet another embodiment of this invention, a reduction of overlap of neighboring signals can be achieved by using a moving belt device as schematically shown in FIG. 12. In a recent publication, a moving belt has been described, although in a completely unrelated application [M.Moini and F. P. Abramson, *Biological Mass Spectrometry*, 20, 308–12 (1991)]. The effect of the moving belt can be to help spread the appearance of sequentially released nucleotide/nucleoside signals as illustrated in FIG. 13. The width between consecutive, i.e. neighboring, signals can be increased with the speed of the moving belt.

Without limiting the scope of the invention, FIG. 12 illustrates a possible configuration of the moving belt module for exonuclease-mediated mass spectrometric sequencing. An endless metal ribbon (10) is driven with variable speed using a controllable stepping motor and appropriately positioned pulleys. Spring-loaded pulleys can be used to maintain a sufficiently high tension on the moving belt. The sample is applied to the belt from the reactor module (A) (FIG. 9), at a position which is in direct contact with a cooling/heating plate, B. In case matrix-assisted laser desorption/ionization mass spectrometry is employed, the sample can be mixed with a matrix solution (M) prior to loading onto the belt. Crystal formation can be observed with a viewing device (D) (CCD camera and optics). Alternatively, the container (M) can be used to mix the sample with a diluent or other reagent, enzyme, internal standard etc. at a mixing valve or vortex (12). In the instance of relatively small molecules such as the released nucleotides, matrix is not essential for the laser desorption/ionization process to take place. The belt, 10 moves the sample under a laser source (E) (with appropriate optics), for desorption and ionization.

A heating element, C, such as a microwave source, can be placed near the surface of the returning belt, separated from the forward moving belt by an insulating shield, I, to clean the surface of the metal ribbon belt (10) of any organic material prior to loading a new sample. Alternatively, a washing station (W) can be integrated before the heating element (C), in this case the function of the heating element C can be to completely dry the metal ribbon prior to reloading of sample. Before and after the laser targets the sample, two differential vacuum pumping stages F and G are positioned. An electric field is applied after the second vacuum stage to accelerate the ions into the mass spectrometer. As mass analyzer, a quadrupol can be used, though other mass analyzing configurations are known in the art and are within the scope of the invention. The design of the vacuum interface of the moving belt between the sample application compartment which is at atmospheric pressure, and the mass spectrometer can be important. In one approach, this vacuum seal can be provided by the use of tunnel seals in a two-stage vacuum lock as previously described [Moini et al, (1991), supra].

As described above, an increase of throughput can be obtained by multiplexing. In yet another embodiment of the invention, the moving belt device can be used for a second dimension in multiplexing by applying s samples from s sequencing reactors A (FIG. 9) simultaneously in different locations onto the moving belt. Desorption and ionization of these multiple samples is achieved by moving the laser beam with adjustable speed and frequency back and forth, perpendicular to the direction of the moving belt. Identification and assignment of the nucleotides/nucleosides detected to the various nucleic acid fragments can be achieved by second dimension multiplexing, i.e. by mass-labeling the nucleic acid fragments with for example —$CH_2$—, —$CH_2CH_2$—, —$CH_2CH_2CH_2$— and —$CH_2(CH_2)_rCH_2$—, and labeling the different reactors, for example, with individual halogen atoms, i.e. F for reactor 1 (thus having the different DNA fragments labeled with —$CH_2F$, —$CH_2CH_2F$, —$CH_2CH_2CH_2F$, —$CH_2(CH_2)_rCH_2F$), Cl for reactor 2 (thus having the different DNA fragments labeled with —$CH_2Cl$, —$CH_2CH_2Cl$, —$H_2CH_2CH_2Cl$, —$CH_2(CH_2)_rCH_2Cl$), Br for reactor 3 etc. This can increase the throughput dramatically. Two-dimensional multiplexing can be applied in different ways. For example, it can be used to simultaneously sequence the fragments forming one set of overlapping deletions of the same long DNA insert. In another embodiment, several subsets of ordered deletions of different DNA inserts can be analyzed in parallel.

Another aspect of this invention concerns kits for sequencing nucleic acids by exonuclease mass spectrometry, which include combinations of the above described sequencing reactants. For instance, in one embodiment, the kit comprises reagents for multiplex mass spectrometric sequencing of several different species of nucleic acid. The kit can include an exonuclease for cleaving the nucleic acids unilaterally from a first end to sequentially release individual nucleotides, a set of nucleotides for synthesizing the different species of nucleic acids, at least a portion of the nucleotides being mass-modified such that sequentially released nucleotides of each of the different species of nucleic acids are distinguishable, a polymerase for synthesizing the nucleic acids from complementary templates and the set of nucleotides, and a solid support for immobilizing one of the nucleic acids or the exonuclease. The kit can also include appropriate buffers, as well as instructions for performing multiplex mass spectrometry to concurrently sequence multiple species of nucleic acids. In another embodiment, the sequencing kit can include an exonuclease for cleaving a target nucleic acid unilaterally from a first end to sequentially release individual nucleotides, a set of nucleotides for synthesizing the different species of nucleic acids, at least a portion of the nucleotides being mass-modified to modulate the exonuclease activity, a polymerase for synthesizing the nucleic acid from a complementary template and the set of nucleotides, and a solid support for immobilizing one of the nucleic acids or the exonuclease.

The present invention is further illustrated by the following examples, which should not be construed as limiting in any way. The contents of all cited references (including literature references, issued patents, published patent applications (including international patent application Publication No. WO 94/16101, entitled *DNA Sequencing* by *Mass Spectrometry* by H. Koester; and international patent application Publication No. WO 94/21822 entitled "DNA Sequencing by Mass Spectrometry Via Exonuclease Degradation" by H. Koester), and co-pending patent applications, (including U.S patent application Ser. No. 08/406,199, entitled DNA *Diagnostics Based on Mass Spectrometry* by H. Koester), and continuations-in-part of co-pending patent applications (published or unpublished) are hereby expressly incorporated by reference.

EXAMPLE 1

Immobilization of Nucleic Acids to Solid Supports Via Disulfide Bonds

As a solid support, Sequelon membranes (Millipore Corp., Bedford, Mass.) with phenyl isothiocyanate groups were used as a starting material. The membrane disks, with a diameter of 8 mm, are wetted with a solution of N-methylmorpholine/water/2-propanol (NMM solution) (2/49/49;v/v/v), the excess liquid removed with filter paper and placed on a piece of plastic film or aluminium foil located on a heating block set to 55° C. A solution of 1 mM 2-mercaptoethylarnine (cysteamine) or 2,2'-dithio-bis (ethylamine) (cystamine) or S-(2-thiopyridyl)-2-thio-ethylamine (10 $\mu$l, 10 nmol) in NMM is added per disk and heated at 55° C. After 15 min, 10 $\mu$l of NMM solution are added per disk and heated for another 5 min. Excess of isothiocyanate groups may be removed by treatment with 10 $\mu$l of a 10 mM solution of glycine in NMM solution. In case of cystamine, the disks are treated with 10 $\mu$l of a solution of 1M aqueous dithiothreitol (DTT)/2-propanol (1:1, v/v) for 15 min at room temperature. Then the disks are thoroughly washed in a filtration manifold with 5 aliquots of 1 ml each of the NMM solution, then with 5 aliquots of 1 ml acetonitrile/water (1/1; v/v) and subsequently dried. If not used immediately, the disks are stored with free thiol groups in a solution of 1M aqueous dithiothreitol/2-propanol (1:1; v/v) and, before use, DTT is removed by three washings with 1 ml each of the NMM solution. Single-stranded nucleic acid fragments with 5'-SH functionality can be prepared by various methods [e.g. B. C. F Chu et al., *Nucleic Acids Res.*, 14, 5591–5603 (1986), Sproat et al., *Nucleic*

*Acids Res.*, 15, 4837–48 (1987) and Oligonucleotides and Analogues. A Practical Approach (F. Eckstein editor), IRL Press Oxford, 1991]. The single-stranded nucleic acid fragments with free 5'-thiol groups are now coupled to the thiolated membrane supports under mild oxidizing conditions. In general, it is sufficient to add the 5'-thiolated nucleic acid fragments dissolved in 10 μl 10 mM de-aerated triethylammonium acetate buffer (TEAA) pH 7.2 to the thiolated membrane supports; coupling is achieved by drying the samples onto the membrane disks with a cold fan. This process can be repeated by wetting the membrane with 10 μl of 10 mM TEAA buffer pH 7.2 and drying as before. When using the 2-thiopyridyl derivatized compounds, anchoring can be monitored by the release of pyridine-2-thione spectrophotometrically at 343 nm.

In another variation of this approach the single-stranded nucleic acid is functionalized with an amino group at the 5'-end by standard procedures. The primary amino group is reacted with 3-(2-pyridyldithio)propionic acid N-hydroxysuccinimide ester (SPDP) and subsequently coupled to the thiolated supports and monitored by the release of pyridyl-2-thione as described above. After denaturation of any remaining protein and, ethanol precipitation of the functionalized nucleic acid, the pellet is dissolved in 10 μl 10 mM TEAA buffer pH 7.2 and 10 μl of a 2 mM solution of SPDP in 10 mM TEAA are added. The reaction mixture is vortexed and incubated for 30 min at 25° C.; excess SPDP is then removed by three extractions (vortexing, centrifugation) with 50 μl each of ethanol and the resulting pellets dissolved in 10 μl 10 mM TEAA buffer pH 7.2 and coupled to the thiolated supports (see above).

The immobilized nucleic acids can be released by three successive treatments with 10 μl each of 10 mM 2-mercaptoethanol in 10 mM TEAA buffer pH 7.2.

EXAMPLE 2

Immobilization of Nucleic Acids on Solid Support Via a Levulinyl Group

5-Aminolevulinic acid is protected at the primary amino group with the Fmoc group using 9-fluorenylmethyl N-succinimidyl carbonate and then transformed into the N-hydroxysuccinimide ester (NHS ester) using N-hydroxysuccinimide and dicyclohexyl carbodiimide under standard conditions. Nucleic acids which are functionalized with primary amino acid at the 5' end are EtOH precipitated and resuspended in 10 μl of 10 mM TEAA buffer pH 7.2. 10 μl of a 2 mM solution of the Fmoc-5-aminolevulinyl-NHS ester in 10 mM TEAA buffer is added, vortexed and incubated at 25° C. for 30 min. The excess of reagents can be removed by ethanol precipitation and centrifugation. The Fmoc group is cleaved off by resuspending the pellets in 10 μl of a solution of 20% piperidine in N,N-dimethylformamide/water (1:1, v/v). After 15 min at 25° C., piperidine is thoroughly removed by three precipitations/centrifugations with 100 μl each of ethanol, the pellets resuspended in 10 μl of a solution of N-methylmorpholine, propanol-2 and water (2/10/88; v/v/v) and coupled to the solid support carrying an isothiocyanate group. In case of the DITC-Sequelon membrane (Millipore Corp., Bedford, Mass.), the membranes are prepared as described in EXAMPLE 1 and coupling is achieved on a heating block at 55° C. as described above. The procedure can be applied to other solid supports with isothiocyanate groups in a similar manner.

The immobilized nucleic acids can be released from the solid support by three successive treatments with 10 μl of 100 mM hydrazinium acetate buffer pH 6.5.

EXAMPLE 3

Immobilization of Nucleic Acids on Solid Supports Via a Trypsin Sensitive Linkage Sequelon DITC membrane disks of 8 mm diameter (Millipore Corp. Bedford, Mass.) are wetted with 10 μl of NMM solution (N-methylmorpholine/propanol-2/water; 2/49/49; v/v/v) and a linker arm introduced by reaction with 10 μl of a 10 mM solution of 1,6-diaminohexane in NMM. The excess of the diamine is removed by three washing steps with 100 μl of NMM solution. Using standard peptide synthesis protocols, two L-lysine residues are attached by two successive condensations with N-Fmoc-N-tBoc-L-lysine pentafluorophenylester, the terminal Fmoc group is removed with piperidine in NMM and the free E-amino group coupled to 1,4-phenylene diisothiocyanate (DITC). Excess DITC is removed by three washing steps with 100 μl propanol-2 each and the N-tBoc groups removed with trifluoroacetic acid according to standard peptide synthesis procedures. The nucleic acids are prepared from the above from a primary amino group at the 5'-terminus. The ethanol precipitated pellets are resuspended in 10 μl of a solution of N-methylmorpholine, propanol-2 and water (2/10/88; v/v/v) and transferred to the Lys-Lys-DITC membrane disks and coupled on a heating block set at 55° C. After drying 10 μl of NMM solution is added and the drying process repeated.

The immobilized nucleic acids can be cleaved from the solid support by treatment with trypsin.

EXAMPLE 4

Immobilization of Nucleic Acids on Solid Supports Via Pyrophosphate Linkage The DITC Sequelon membrane, (disks of 8 mm diameter) are prepared as described in EXAMPLE 3 and 10 μl of a 10 mM solution of 3-aminopyridine adenine dinucleotide (APAD) (Sigma) in NMM solution added. The excess of APAD is removed by a 10 μl wash of NMM solution and the disks are treated with 10 ul of 10 mM sodium periodate in NMM solution (15 min, 25° C.). Excess of periodate is removed and the nucleic acids having a primary amino group at the 5'-end are dissolved in 10 μl of a solution of N-methylmorpholine/propanol-2/water (2/10/88; v/v/v) and coupled to the 2',3'-dialdehydo functions of the immobilized NAD analog.

The immobilized nucleic acids can be released from the solid support by treatment with either NADase or pyrophosphatase in 10 mM TEAA buffer at pH 7.2 at 37° C. for 15 min.

EXAMPLE 5

Synthesis of Pyrimidine Nucleotides Mass-modified at C-5 of the Heterocyclic Base with Glycine Residues Starting material is 5-(3-aminopropynyl-1)-3',5'-di-p-tolyldeoxyuridine prepared and 3',5'-de-O-acylated according to literature procedures [Haralambidis et al., *Nucleic Acids Res.*, 15,4857–76 (1987)]. 0.281 g (1.0 mmole) 5-(3-aminopropynyl-1)-2'-deoxyuridine are reacted with 0.927 g (2.0 mmole) N-Fmoc-glycine pentafluorophenylester in 5 ml absolute N,N-dimethylformamide in the presence of 0.129 g (1 mmole; 174 μl) N,N-diisopropylethylamine for 60 min at room temperature. Solvents are removed by rotary evaporation and the product purified by silica gel chromatography (Kieselgel 60, Merck; column: 2.5×50 cm, elution with chloroform/methanol mixtures). Yield 0.44 g (0.78 mmole, 78%). In order to add another glycine residue, the Fmoc group is removed with a 20 min treatment with a 20% solution of piperidine in DMF, evaporated in vacuo and the remaining solid material extracted three times with 20 ml ethylacetate; after having removed the remaining ethylacetate N-Fmoc-glycine pentafluorophenylester is being coupled as described above. This glycine-modified thymidine analogue building block for chemical DNA synthesis can be used to substitute for thymidine or uridine nucleotides in the target nucleic acid.

EXAMPLE 6

Synthesis of Pyrimidine Nucleotides Mass-modified at C-5 of the Heterocyclic Base with β-alanine Residues Starting material is the same as in EXAMPLE 5. 0.281 g (1.0 mmole) 5-(3-Aminopropynyl-1)-2'-deoxyuridine is reacted with N-Fmoc-β-alanine pentafluorophenylester (0.955 g, 2.0 mmole) in 5 ml N,N-dimethylformamide (DMF) in the presence of 0.129 g (174 µl, 1.0 mmole) N,N-diisopropylethylamine for 60 min at room temperature. Solvents are removed and the product purified by silica gel chromatography as described in EXAMPLE 6. Yield: 0.425 g (0.74 mmole, 74%). Another β-alanine moiety could be added in exactly the same way after removal of the Fmoc group. This building block can be substitute for any of the thymidine or uridine residues in the target nucleic acid.

EXAMPLE 7

Synthesis of a Pyrimidine Nucleotide Mass-modified at C-5 of the Heterocyclic Base with Ethylene Glycol Monomethyl ether.

As nucleosidic component, 5-(3-aminopropynyl-1)-2'-deoxyuridine is used in this example (see EXAMPLE 5 and 6). The mass-modifying functionality is obtained as follows: 7.61 g (100.0 mmole) freshly distilled ethylene glycol monomethyl ether dissolved in 50 ml absolute pyridine is reacted with 10.01 g (100.0 numole) recrystallized succinic anhydride in the presence of 1.22 g (10.0 mmole) 4-N,N-dimethylaminopyridine overnight at room temperature. The reaction is terminated by the addition of water (5.0 ml), the reaction mixture evaporated in vacuo, co-evaporated twice with dry toluene (20 ml each) and the residue redissolved in 100 ml dichloromethane. The solution is extracted successively, twice with 10% aqueous citric acid (2×20 ml) and once with water (20 ml) and the organic phase dried over anhydrous sodium sulfate. The organic phase is evaporated in vacuo, the residue redissolved in 50 ml dichloromethane and precipitated into 500 ml pentane and the precipitate dried in vacuo. Yield: 13.12 g (74.0 mmole; 74%). 8.86 g (50.0 mmole) of succinylated ethylene glycol monomethyl ether is dissolved in 100 ml dioxane containing 5% dry pyridine (5 ml) and 6.96 g (50.0 mmole) 4-nitrophenol and 10.32 g (50.0 mmole) dicyclohexylcarbodiimide is added and the reaction run at room temperature for 4 hours. Dicyclohexylurea is removed by filtration, the filtrate evaporated in vacuo and the residue redissolved in 50 ml anhydrous DMF. 12.5 ml (about 12.5 mmole 4-nitrophenylester) of this solution is used to dissolve 2.81 g (10.0 imnole) 5-(3-aminopropynyl-1)-2'-deoxyuridine. The reaction is performed in the presence of 1.01 g (10.0 mmole; 1.4 ml) triethylamine at room temperature overnight. The reaction mixture is evaporated in vacuo, co-evaporated with toluene, redissolved in dichloromethane and chromatographed on silicagel (Si60, Merck; column 4×50 cm) with dichloromethane/methanol mixtures. The fractions containing the desired compound are collected, evaporated, redissolved in 25 ml dichloromethane and precipitated into 250 ml pentane.

EXAMPLE 8

Synthesis of Pyrimidine Nucleotides Mass-modified at C-5 of the Heterocyclic Base with Diethylene Glycol Monomethyl Ether Nucleosidic starting material is as in previous examples, 5-(3-aminopropynyl-1)-2'-deoxyuridine. The mass-modifying functionality is-obtained similar to EXAMPLE 7. 12.02 g (100.0 mmole) freshly distilled diethylene glycol monomethyl ether dissolved in 50 ml absolute pyridine is reacted with 10.01 g (100.0 mmole) recrystallized succinic anhydride in the presence of 1.22 g (10.0 mmole) 4-N,N-dimethylaminopyridine (DMAP) overnight at room temperature. The work-up is as described in EXAMPLE 7. Yield: 18.35 g (82.3 mmole, 82.3%). 11.06 g (50.0 mmole) of succinylated diethylene glycol monomethyl ether is transformed into the 4-nitrophenylester and subsequently 12.5 mmole reacted with 2.81 g (10.0 mmole) of 5-(3-aminopropynyl-1)-2'-deoxyuridine as described in EXAMPLE 7. Yield after silica gel column chromatography and precipitation into pentane: 3.34 g (6.9 mmole, 69%).

EXAMPLE 9

Synthesis of Deoxyadenosine Mass-modified at C-8 of the Heterocyclic Base with glycine Starting material is N6-benzoyl-8-bromo-5'-O-(4,4'-dimethoxytrityl)-2'-deoxyadenosine prepared according to literature [Singh et al., *Nucleic Acids Res.* 18, 3339–45 (1990)]. 632.5 mg (1.0 mmole) of this 8-bromo-deoxyadenosine derivative is suspended in 5 ml absolute ethanol and reacted with 251.2 mg (2.0 mmole) glycine methyl ester (hydrochloride) in the presence of 241.4 mg (2.1 mmole; 366 ul) N,N-diisopropylethylamine and refluxed until the starting nucleosidic material has disappeared (4–6 hours) as checked by thin layer chromatography (TLC). The solvent is evaporated and the residue purified by silica gel chromatography (column 2.5×50 cm) using solvent mixtures of chloroform/methanol containing 0.1% pyridine. The product fractions are combined, the solvent evaporated, dissolved in 5 ml dichloromethane and precipitated into 100 ml pentane. Yield: 487 mg (0.76 mmole, 76%).

EXAMPLE 10

Synthesis of Deoxyadenosine Mass-modified at C-8 of the Heterocyclic Base with Glycylglycine This derivative is prepared in analogy to the glycine derivative of EXAMPLE 9. 632.5 mg (1.0 mmole) N6-Benzoyl-8-bromo-5'-O-(4,4'-dimethoxytrityl)-2'-deoxyadenosine is suspended in 5 ml absolute ethanol and reacted with 324.3 mg (2.0 mmole) glycyl-glycine methyl ester in the presence of 241.4 mg (2.1 mmole, 366 µl) N,N-diisopropylethylamine. The mixture is refluxed and completeness of the reaction checked by TLC. Work-up and purification is similar to that described in EXAMPLE 9. Yield after silica gel column chromatography and precipitation into pentane: 464 mg (0.65 mmole, 65%).

EXAMPLE 11

Synthesis of Deoxythymidine Mass-modified at the C-2' of the Sugar Moiety with Ethylene Glycol Monomethyl Ether Residues Starting material is 5'-O-(4,4-dimethoxytrityl)-2'-amino-2'-deoxythymidine synthesized according to published procedures [e.g. Verheyden et al., J. Org. Chem., 36, 250–254 (1971); Sasaki et al., J. Org. Chem., 41, 3138–3143 (1976); Imazawa et al., J. Org. Chem., 44, 2039–2041 (1979); Hobbs et al., J. Org. Chem., 42, 714–719 (1976); Ikehara et al., Chem. Pharm. Bull. Japan, 26, 240–244 (1978); see also PCT Application WO 88/00201]. 5'-O-(4,4-dimethoxytrityl)-2'-amino-2'-deoxythymidine (559.62 mg; 1.0 mmole) is reacted with 2.0 mmole of the 4-nitrophenyl ester of succinylated ethylene glycol monomethyl ether (see EXAMPLE 7) in 10 ml dry DMF in the presence of 1.0 mmole (140 μl) triethylamine for 18 hours at room temperature. The reaction mixture is evaporated in vacuo, co-evaporated with toluene, redissolved in dichloromethane and purified by silica gel chromatography (Si60, Merck, column: 2.5×50 cm; eluent: chloroform/methanol mixtures containing 0.1% triethylamine). The product-containing fractions are combined, evaporated and precipitated into pentane. Yield: 524 mg (0.73 mmol; 73%).

In an analogous way, employing the 4-nitrophenyl ester of succinylated diethylene glycol monomethyl ether (see EXAMPLE 8) and triethylene glycol monomethyl ether, the corresponding mass-modified deoxythymidine is prepared. The mass difference between the ethylene, diethylene and triethylene glycol derivatives is 44.05, 88.1 and 132.15 dalton respectively.

EXAMPLE 12

Synthesis of Deoxyuridine-5'-Triphosphate Mass-modified at C-5 of the Heterocyclic Base with Glycine, Glycyl-glycine and β-alanine Residues 0.281 g (1.0 mmole) 5-(3-Aminopropynyl-1)-2'-deoxyuridine (see EXAMPLE 5) is reacted with either 0.927 g (2.0 mmole) N-Fmoc-glycine pentafluorophenylester or 0.955 g (2.0 mmole) N-Fmoc-β-alanine pentafluorophenyl ester in 5 ml dry DMF in the presence of 0.129 g N,N-diisopropylethylamine (174 μl, 1.0 mmole) overnight at room temperature. Solvents are removed by evaporation in vacuo and the condensation products purified by flash chromatography on silica gel [Still et al., J. Org. Chem., 43, 2923–2925 (1978)]. Yields: 476 mg (0.85 mmole: 85%) for the glycine and 436 mg (0.76 mmole; 76%) for the -alanine derivative. For the synthesis of the glycyl-glycine derivative, the Fmoc group of 1.0 mmole Fmoc-glycine-deoxyuridine derivative is removed by one-hour treatment with 20% piperidine in DMF at room temperature. Solvents are removed by evaporation in vacuo, the residue is co-evaporated twice with toluene and condensed with 0.927 g (2.0 mmole) N-Fmoc-glycine pentafluorophenyl ester and purified following standard protocol. Yield: 445 mg (0.72 mmole; 72%). The glycyl-, glycyl-glycyl- and β-alanyl-2'-deoxyuridine derivatives N-protected with the Fmoc group are now transformed to the 3'-O-acetyl derivatives by tritylation with 4,4-dimethoxytrityl chloride in pyridine and acetylation with acetic anhydride in pyridine in a one-pot reaction and subsequently detritylated by one-hour treatment with 80% aqueous acetic acid according to standard procedures. Solvents are removed, the residues dissolved in 100 ml chloroform and extracted twice with 50 ml 10% sodium bicarbonate and once with 50 ml water, dried with sodium sulfate, the solvent evaporated and the residues purified by flash chromatography on silica gel. Yields: 361 mg (0.60 mmole; 71%) for the glycyl-, 351 mg (0.57 mmole; 75%) for the alanyl- and 323 mg (0.49 mmole; 68%) for the glycyl-glycyl-3-O'-acetyl-2'-deoxyuridine derivatives respectively. Phosphorylation at the 5'-OH with $POC_{l3}$, transformation into the 5'-triphosphate by in-situ reaction with tetra(tri-n-butylammonium) pyrophosphate in DMF, 3'-de-O-acetylation and cleavage of the Fmoc group and final purification by anion-exchange chromatography on DEAE-Sephadex is performed. Yields according to UV-absorbance of the uracil moiety: 5-(3-(N-glycyl)-amidopropynyl- 1)-2'-deoxyuridine-5'-triphosphate 0.41 mmole (84%), 5-(3-(N-.alanyl)-amidopropynyl-1)-2'-deoxyuridine-5'-triphosphate 0.43 mmole (75%) and 5-(3-(N-glycyl-glycyl)-amidopropynyl-1)-2'-deoxyuridine-5'-triphosphate 0.38 mmole (78%).

EXAMPLE 13

Synthesis of 8-Glycyl- and 8-Glycyl-glycyl-2'-Deoxyadenosine-5'-Triphosphate.

727 mg (1.0 mmole) of N6-(4-tert.butylphenoxyacetyl)-8-glycyl-5'-(4,4-dimethoxytrityl)-2'-deoxyadenosine or 800 mg (1.0 mmole) N6-(4-tert.butylphenoxyacetyl)-8-glycyl-glycyl-5'-(4,4-dimethoxytrityl)-2'-deoxyadenosine prepared according to EXAMPLES 9 and 10 and literature [Köster et al., Tetrahedron, 37: 362 (1981)] are acetylated with acetic anhydride in pyridine at the 3'-OH, detritylated at the 5'-position with 80% acetic acid in a one-pot reaction and transformed into the 5'-triphosphates via phosphorylation with $POCl_3$ and reaction in-situ with tetra(tri-n-butylammonium) pyrophosphate. Deprotection of the N6-tert-butylphenoxyacetyl, the 3'-O-acetyl and the O-methyl group at the glycine residues is achieved with concentrated aqueous ammonia for three hours at room temperature. Ammonia is removed by lyophilization and the residue washed with dichloromethane, solvent removed by evaporation in vacuo and the remaining solid material purified by anion-exchange chromatography on DEAE-Sephadex using a linear gradient of triethylammonium bicarbonate from 0.1 to 1.0 M. The nucleoside triphosphate containing fractions (checked by TLC on polyethyleneimine cellulose plates) are combined and lyophilized. Yield of the 8-glycyl-2'-deoxyadenosine-5'-triphosphate (determined by the UV-absorbance of the adenine moiety) is 57% (0.57 mmole); the yield for the 8-glycyl-glycyl-2'-deoxyadenosine-5'-triphosphate is 51% (0.51 mmole).

EXAMPLE 14

Figure 22:
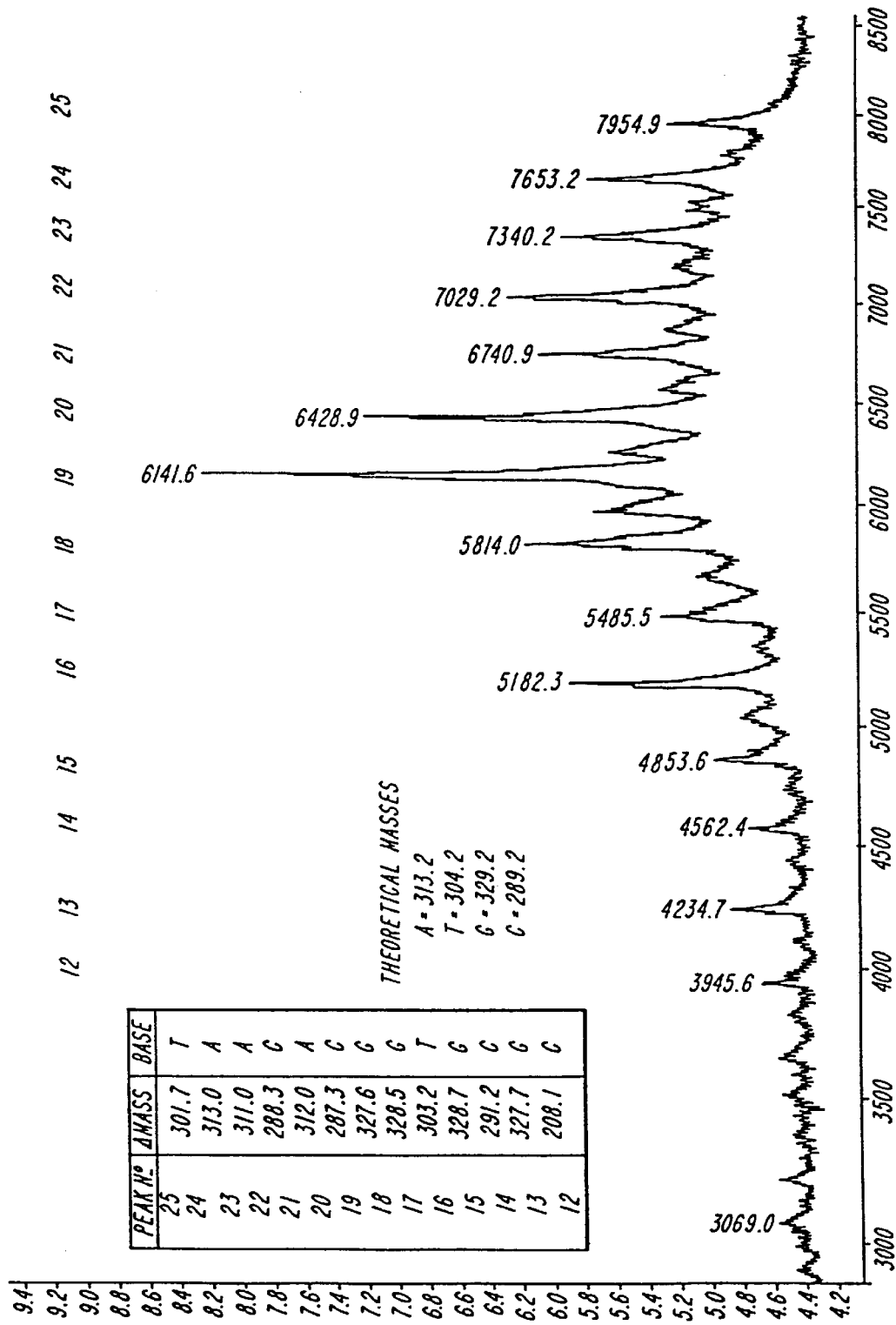
FIG. 22 shows the mass spectrum obtained based on exonuclease degradation of a 25-mer with a 3' exonuclease (snake venom phosphodiesterase).

Exonuclease Degradation of a 25-mer with a 3'-exonuclease (Snake Venom Phosphodiesterase)
Materials and Methods 400 pmol of the 5'-biotinylated 25-mer d(TACATTCCCACCGCGTGGCACAAT SEQ ID NO. 1) immobilized to streptavidin Dynabeads were suspended in 100 μl water and incubated for four minutes with 3 μl (6×10−3 units) of snake venom phosphodiesterase at room temperature. The beads were separated using a magnetic particle separator (MPS) and washed once each with 10mM Tris-HCL, pH 7.5, 1 mM EDTA, 2M NH$_4$Cl and water. The immobilized truncated sequences were cleaved from the support by a 10 min treatment with 25% NH40H at 60° C., the supernatant was lyophilized and dissolved in 3 μl of water. 0.4 μl of this solution were mixed with 0.5 μl of the matrix solution (3-hydroxypicolinic acid:ammonium citrate=10:1 in 50% aqueous acetonitrile) and introduced into the mass spectrometer (Finnegan Vison 2000 with reflectron in positive ion mode).
Results FIG. 22 shows the mass spectrum obtained.

EXAMPLE 15

Immobilization of Nucleic Acids on Solid Supports Via an Acid-labile Covalent Bifunctional Trityl Linker.

Aminolink DNA was prepared and purified according to standard methods. A portion (10eq) was evaporated to dryness on a speedvac and suspended in anhydrous DMF/ pyridine (9:1; 0.1 ml). To this was added the chlorotrityl chloride resin (1eq, 1.05 μmol/mg loading) and the mixture

```
                        SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

TACATTCCCA CCGCGTGGCA CAAT                                              24
``` was shaken for 24 hours. The loading was checked by taking a sample of the resin, detritylating this using 80% AcOH, and measuring the absorbance at 260 nm. Loading was ca. 150 pmol/mg resin.

In 80% acetic acid, the half-life of cleavage was found to be substantially less than 5 minutes—this compares with trityl ether-based approaches of half-lives of 105 and 39 minutes for para and meta substituted bifunctional dimethoxytrityl linkers respectively. Preliminary results have also indicated that the hydroxy picolinic acid matrix alone is sufficient to cleave the DNA from the chlorotrityl resin.

EXAMPLE 16

Immobilization of Nucleic Acids on Solid Supports Via Hydrophobic Trityl Linker.

The primer contained a 5'-dimethoxytrityl group attached using routine trityl-on DNA synthesis.

C18 beads from an oligo purification cartridge (0.2 mg) placed in a filter tip was washed with acetonitrile, then the solution of DNA (50 ng in 25,1) was flushed through. This was then washed with 5% acetonitrile in ammonium citrate buffer (70 mM, 250 μl). To remove the DNA from the C18, the beads were washed with 40% acetonitrile in water (10 μl) and concentrated to ca, 2 μl on the Speedvac. The sample was then submitted to MALDI.

The results showed that acetonitrile/water at levels of ca.>30% are enough to dissociate the hydrophobic interaction. Since the matrix used in MALDI contains 50% acetonitrile, the DNA can be released from the support and MALDIed successfully (with the trityl group removed during the MALDI process).

All of the above-cited references and publications are hereby incorporated by reference.

Equivalents

Those skilled in the art will recognize, or be able to ascertain using no more than routine experimentation, numerous equivalents to the specific procedures described herein. Such equivalents are considered to be within the scope of this invention and are covered by the following claims.

What is claimed is:

1. A method of determining a sequence of a nucleic acid, comprising the steps of:
   (i) obtaining the nucleic acid to be sequenced;
   (ii) cleaving the nucleic acid to be sequenced from a first end to a second end with an exonuclease to sequentially release individual nucleotides;
   (iii) identifying each of the sequentially released nucleotides by mass spectrometry; and
   (iv) determining the sequence of the nucleic acid from the identified nucleotides.

2. The method of claim 1, wherein the nucleic acid is a 2'-deoxyribonucleic acid (DNA).

3. The method of claim 1, wherein the nucleic acid is a ribonucleic acid (RNA).

4. The method of claim 1, wherein the exonuclease is selected from the group consisting of snake venom phosphodiesterase, spleen phosphodiesterase, Bal-31 nuclease, *E. coli* exonuclease I, *E. coli* exonuclease VII, Mung Bean Nuclease, S1 Nuclease, an exonuclease activity of *E. coli* DNA polymerase I, an exonuclease activity of the Klenow fragment of DNA polymerase I, an exonuclease activity of T4 DNA polymerase, an exonuclease activity of T7 DNA polymerase and an exonuclease activity of Taq DNA polymerase, *E. coli* exonuclease III, λ exonuclease an exonuclease activity of *Pyrococcus species* GB-D DNA polymerase and an exonuclease activity of *Thermococcus litoralis* DNA polymerase.

5. The method according to claim 1, wherein the exonuclease is immobilized by covalent attachment to a solid support, entrapment within a gel matrix, or contained in a reactor with a semipermeable membrane.

6. The method according to claim 5, wherein the solid support is a capillary and the exonuclease is covalently attached to an inner wall of the capillary.

7. The method of claim 5, wherein the solid support is selected from the group consisting of glass beads, cellulose beads, polystyrene beads, epichlorohydrin-cross-linked -dextran beads, polyacrylamide beads and agarose beads.

8. The method according to claim 5, wherein the solid support is a flat membrane.

9. The method according to claim 1, wherein the nucleic acid is immobilized by covalent attachment to a solid support and the exonuclease is in a solution and is contacted with the immobilized nucleic acid.

10. The method according to claim 9, wherein the solid support is a capillary and the nucleic acid is covalently attached to an inner wall of the capillary.

11. The method according to claim 9, wherein the solid support is selected from the group consisting of glass beads, cellulose beads, polystyrene beads, epichlorohydrin-cross-linked dextran beads, polyacrylamide beads and agarose beads.

12. The method according to claim 9, wherein the solid support is a flat membrane.

13. The method according to claim 1, wherein the nucleic acid comprises mass-modified nucleotides.

14. The method according to claim 13, wherein the mass-modified nucleotides modulate the rate of the exonuclease activity.

15. The method according to claim 1, wherein the sequentially released nucleotides are mass-modified subsequent to exonuclease release and prior to mass spectrometric identification.

16. The method according to claim 15, wherein the sequentially released nucleotides are mass-modified by contact with an alkaline phosphatase.

17. The method of claim 9, wherein the nucleic acid further comprises a linking group (L) for covalently attaching the nucleic acid to the solid support.

18. The method of claim 17, wherein the solid support further comprises a splint oligonucleotide and the linking group (L) comprises a nucleotide sequence able to anneal to the splint oligonucleotide and be covalently attached to the solid support by action of a ligase.

19. The method of claim 1, wherein the mass spectrometry format used in step (iii) is selected from the group consisting of fast atomic bombardment (FAB), plasma desorption (PD), thermospray (TS), electrospray (ES) and matrix assisted laser desorption (MALDI).

20. The method of claim 1, wherein the mass analyzer used in step (iii) is a time-of-flight (TOF) configuration or a quadrapole.

21. A method of determining a sequence of a nucleic acid, comprising the steps of:
(i) obtaining the nucleic acid to be sequenced;
(ii) cleaving the nucleic acid to be sequenced from a first end to a second end with an exonuclease to produce multiple sets of nested nucleic acid fragments;
(iii) determining the molecular weight value of each one of the sets of nucleic acid fragments by mass spectrometry; and
(iv) determining the sequence of the nucleic acid from the molecular weight values of the sets of nucleic acid fragments.

22. The method of claim 21, wherein the nucleic acid is a 2'-deoxyribonucleic acid (DNA).

23. The method of claim 21, wherein the nucleic acid is a ribonucleic acid (RNA).

24. The method of claim 21, wherein the exonuclease is selected from the group consisting of snake venom phosphodiesterase, spleen phosphodiesterase, Bal-31 nuclease, E. coli exonuclease I, E. coli exonuclease VII, Mung Bean Nuclease, S1 Nuclease, an exonuclease activity of E. coli DNA polymerase I, an exonuclease activity of the Klenow fragment of DNA polymerase I, an exonuclease activity of T4 DNA polymerase, an exonuclease activity of T7 DNA polymerase, an exonuclease activity of Taq DNA polymerase, E. coli exonuclease III, λ exonuclease, an exonuclease activity of Pyrococcus species GB-D DNA polymerase and an exonuclease activity of Thermococcus litoralis DNA polymerase.

25. The method of claim 21, wherein the exonuclease is immobilized by covalent attachment to a solid support, entrapment within a gel matrix, or contained in a reactor with a semipermeable membrane.

26. The method of claim 25, wherein the solid support is a capillary and the exonuclease activity is covalently attached to an inner wall of the capillary.

27. The method of claim 25, wherein the solid support is selected from the group consisting of glass beads, cellulose beads, polystyrene beads, epichlorohydrin-cross-linked dextran beads, polyacrylamide beads and agarose beads.

28. The method of claim 25, wherein the solid support is a flat membrane.

29. The method of claim 21, wherein the nucleic acid is immobilized by covalent attachment to a solid support and the exonuclease is in a solution and is contacted with the immobilized nucleic acid.

30. The method of claim 29, wherein the solid support is a capillary and the nucleic acid is covalently attached to an inner wall of the capillary.

31. The method of claim 29, wherein the solid support is selected from the group consisting of glass beads, cellulose beads, polystyrene beads, epichlorohydrin-cross-linked dextran beads, polyacrylamide beads and agarose beads.

32. The method of claim 29, wherein the solid support is a flat membrane.

33. The method of claim 21, wherein the nucleic acid comprises mass-modified nucleotides.

34. The method of claim 33, wherein the mass-modified nucleotides modulate the rate of the exonuclease activity.

35. The method of claim 21, wherein the multiple sets of nested nucleic acid fragments are mass-modified subsequent to exonuclease release and prior to mass spectrometric identification.

36. The method of claim 35, wherein the multiple sets of nested nucleic acid fragments are mass-modified by contact with an alkaline phosphatase.

37. The method of claim 29, wherein the nucleic acid further comprises a linking group (L) for covalently attaching the nucleic acid to the solid support.

38. The method of claim 37, wherein the solid support further comprises a splint oligonucleotide and the linking group (L) comprises a nucleotide sequence able to anneal to the splint oligonucleotide and be covalently attached to the solid support by action of a ligase.

39. The method of claim 21, wherein the mass spectrometry format used in step (iii) is selected from the group consisting of fast atomic bombardment (FAB), plasma desorption (PD), thermospray (TS), electrospray (ES) and matrix assisted laser desorption (MALDI).

40. The method of claim 21, wherein the mass analyzer used in step (iii) is a time-of-flight (TOF) configuration or a quadrapole.

41. A method of nucleic acid sequencing, comprising the steps of:
(a) obtaining a target nucleic acid to be sequenced wherein the target nucleic acid sequence is flanked by cleavable sites at both ends and wherein the plus and the minus strand of the target nucleic acid are distinguishable from each other by differential mass-modification;
(b) cleaving the target nucleic acid at the flanking cleavable sites;

(c) denaturing the cleaved target nucleic acid to generate single-stranded plus and minus strands;

(d) simultaneously cleaving the denatured plus and minus strands from a first end to a second end with an exonuclease to sequentially release individual nucleotides, wherein the individual nucleotides derived from the plus strand are mass-differentiated from the individual nucleotides derived from the minus strand;

(e) identifying each of the sequentially released nucleotides produced in step (d) by mass spectrometry; and (f) determining the sequence of the target nucleic acid from the identified nucleotides.

42. The method of claim 41, wherein prior to the exonuclease cleavage of step (d), the plus and the minus strands are immobilized to a solid support.

43. A method of nucleic acid sequencing, comprising the steps of:

(a) obtaining a target nucleic acid to be sequenced wherein the target nucleic acid sequence is flanked by cleavable sites at both ends and wherein the plus and the minus strand of the target nucleic acid are distinguishable from each other by differential mass-modification;

(b) cleaving the target nucleic acid at the flanking cleavable sites;

(c) denaturing the cleaved target nucleic acid to generate single-stranded plus and minus strands;

(d) simultaneously cleaving the denatured plus and minus strands from a first end to a second end with an exonuclease to produce multiple sets of nested nucleic acid fragments, wherein the nested nucleic acid fragments derived from the plus strand are mass-differentiated from the nested nucleic acid fragments derived from the minus strand;

(e) identifying each of the nested nucleic acid fragments produced in step (d) by mass spectrometry; and (f) determining the sequence of the target nucleic acid from the identified nested nucleic acid fragments.

44. The method of claim 43, wherein prior to the exonuclease cleavage of step (d), the plus and the minus strands are immobilized to a solid support.

* * * * *

UNITED STATES PATENT AND TRADEMARK OFFICE
CERTIFICATE OF CORRECTION

PATENT NO. : 6,140,053
DATED : October 31, 2000
INVENTOR(S) : Koster, H

It is certified that error appears in the above-identified patent and that said Letters Patent is hereby corrected as shown below:

On the title page,

In Item [75] Inventor, replace "Concord, Mass" with —La Jolla, Calif.—

In Item [63] Related U.S. Application Data, delete the entire section and insert the following in lieu thereof:

—Continuation of application No. 08/744,590, Nov. 6, 1996.—

In Item [56], References Cited, Other Publications, replace "Certified English translation of European patent 041288A1," with —Certified English translation of European patent 0412883A1,—

The following citations are to be added to Item [56] entitled Other Publications:

"Nordhoff et al. "Ion stability of nucleic acids in infrared matrix-assisted laser desorption/ionization mass spectrometry," Nuc. Acids Res. 21 (15):3347-3357 (1993)."

"Hasan, A. et al. "Base-boronated dinucleotides: synthesis and effect of $N^7$-cyanoborane substitution on the base protons," Nuc. Acids Res. 24:2150-2157 (1996)."

"Gruić-Sovulj, I. et al. "Matrix-assisted laser desorption/ionisation mass spectrometry of transfer ribonucleic acids isolated from yeast," Nuc. Acids Res. 25(9):1859-61 (1997)."

UNITED STATES PATENT AND TRADEMARK OFFICE
CERTIFICATE OF CORRECTION

PATENT NO. : 6,140,053
DATED : October 31, 2000
INVENTOR(S) : Koster, H

It is certified that error appears in the above-identified patent and that said Letters Patent is hereby corrected as shown below:

"Haglund *et al.* "Matrix-assisted laser-desorption mass spectrometry of DNA using an infrared free-electron laser," *SPIE* 1854:117-128, January 22, 1993."

"Schleitz *et al.* "Progress towards DNA sequence determination using laser ablation time-of-flight mass spectrometry," paper presented at 40th ASMS Conference on Mass Spectrometry and Allied topics, Washington, D.C., June 1992."

"Tang *et al.* "Improving mass resolution in MALDI-TOF analysis of DNA," American Society of Mass Spectrometrists Conference: May 21 to 26, 1995."

Figure 21A:
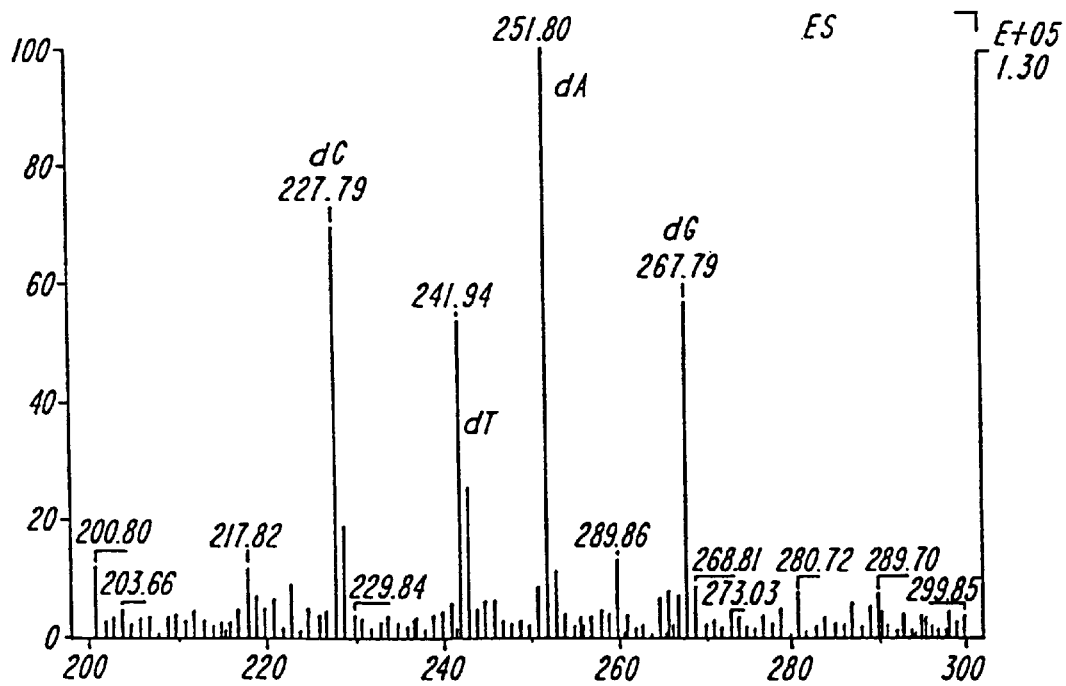
FIG. 21 A provides Electrospray (ES) spectra of three mixtures: (A) a 1:1:1:1 mixture of A:C:G:T; (B) a 1:1:1:0.5 mixture of A:C:G:T; and (C) a 1:1:1:0.2 mixture of A:C:G:T. All four nucleosides can be easily determined and discriminated by their molecular weights, even in a 1:1:1:1 mixture. Qualitatively, the three spectra also clearly reveal the different dT concentrations in the three mixtures.
FIG. 21B is an expanded version around the dT signal of FIG. 21A (panel 2).
Figure 21B:
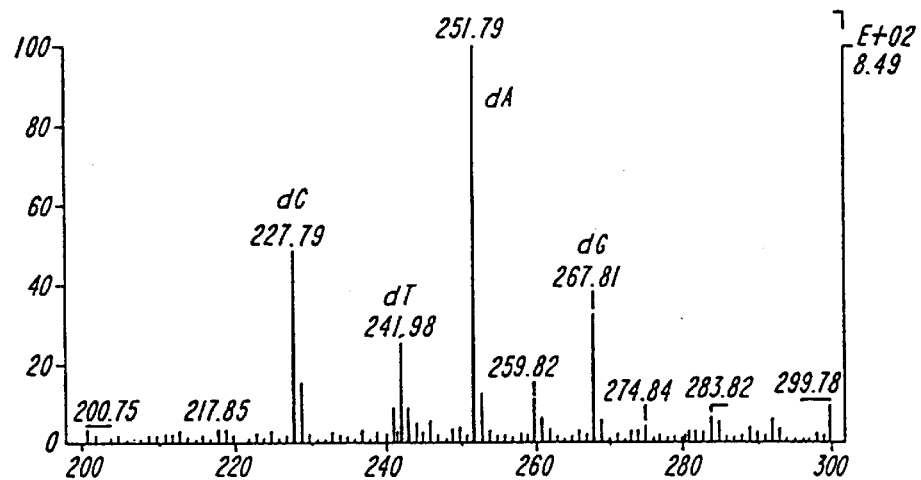
Figure 21C:
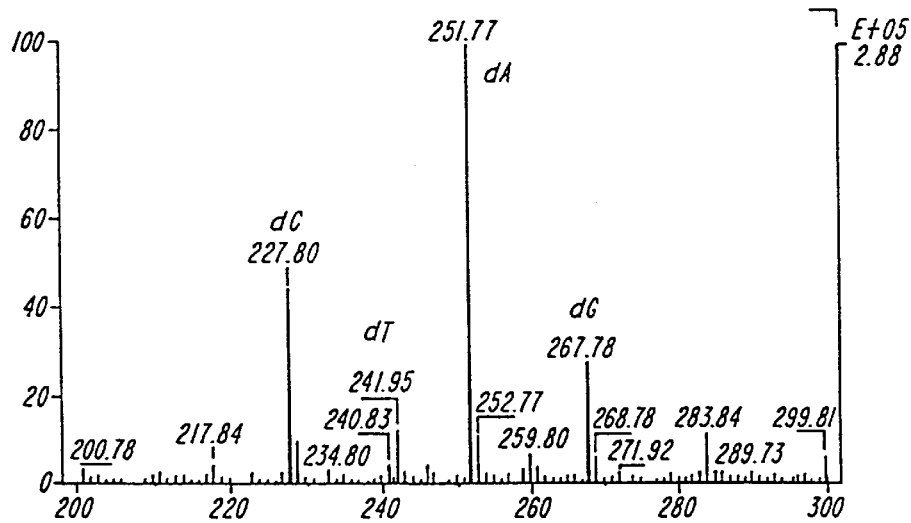
Figure 21D:
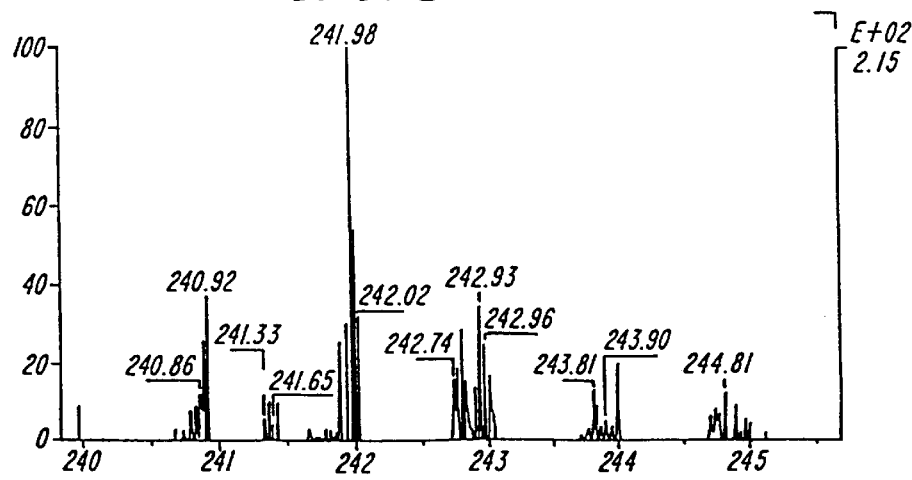

IN THE SPECIFICATION:

At Column 2, line 39 replace "sonification" with —sonication—
At Column 7, line 4 replace "FIG. 21B" with —FIG. 21D—
At Column 7, line 5 delete "(panel 2)"

Signed and Sealed this

Twenty-ninth Day of May, 2001

*Attest:*

NICHOLAS P. GODICI

*Attesting Officer*     *Acting Director of the United States Patent and Trademark Office*